United States Patent
Berk et al.

(10) Patent No.: US 10,913,701 B2
(45) Date of Patent: Feb. 9, 2021

(54) PROCESSES FOR PURIFICATION, RECOVERY, AND CONVERSION OF CHLOROPHENOL SALTS AND PREPARATION AND RECOVERY OF PRODUCTS PREPARED THEREFROM

(71) Applicant: Monsanto Technology LLC, St. Louis, MO (US)

(72) Inventors: Howard C. Berk, St. Louis, MO (US); Bruno de Kort, St. Louis, MO (US); John Joseph Parlow, Arnold, MO (US); Amy E. Stroman, Hazelwood, MO (US); Junqiu Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/467,622

(22) PCT Filed: Dec. 4, 2017

(86) PCT No.: PCT/US2017/064424
§ 371 (c)(1),
(2) Date: Jun. 7, 2019

(87) PCT Pub. No.: WO2018/106564
PCT Pub. Date: Jun. 14, 2018

(65) Prior Publication Data
US 2019/0322612 A1    Oct. 24, 2019

Related U.S. Application Data

(60) Provisional application No. 62/431,205, filed on Dec. 7, 2016.

(51) Int. Cl.
*C07C 63/10* (2006.01)
*C07C 37/68* (2006.01)

(52) U.S. Cl.
CPC ............ *C07C 63/10* (2013.01); *C07C 37/685* (2013.01)

(58) Field of Classification Search
None
See application file for complete search history.

(56) References Cited

U.S. PATENT DOCUMENTS

| 2,480,817 A | 8/1949 | Warren et al. |
| 2,651,659 A | 9/1953 | Warren et al. |

(Continued)

FOREIGN PATENT DOCUMENTS

| CN | 102838482 A | 12/2012 |
| CN | 102942474 A | 2/2013 |

(Continued)

OTHER PUBLICATIONS

International Preliminary Report on Patentability, PCT/US2017/064424, dated Jun. 20, 2019, 7 pages.

(Continued)

*Primary Examiner* — Sudhakar Katakam
*Assistant Examiner* — Jennifer C Sawyer
(74) *Attorney, Agent, or Firm* — Stinson LLP; James E. Davis

(57) ABSTRACT

The present invention generally relates to processes for purification, recovery, and conversion of chlorophenol salts (e.g., 2,5-dichlorophenol and salts thereof). In various aspects, the present invention is related to removing one or more impurities from chlorophenol salt-containing process streams and/or recovering chlorophenol salts from process streams for use of the recovered chlorophenol elsewhere in an integrated process. Process streams that may be treated in accordance with the present invention include those incorporating one or more chlorophenol salts in a feed mixture and also those where one or more chlorophenol salts are (Continued)

present in a product or by-product stream of an integrated process. For example, conversion processes of the present invention are suitable as one piece of an integrated process for producing 3,6-dichloro-2-methoxybenzoic acid (dicamba) or a salt or ester thereof or a process for producing 2,4-dichlorophenoxyacetic acid (2,4-D) or a salt or ester thereof. The present invention further relates to processes for preparation, purification, and recovery of intermediates formed in integrated processes utilizing chlorophenol salts such as 2,5-dichlorophenol as starting material, including the intermediate 3,6-dichlorosalicylic acid (3,6-DCSA) formed during preparation of dicamba from 2,5-dichlorophenol.

31 Claims, 10 Drawing Sheets

(56) References Cited

U.S. PATENT DOCUMENTS 3,013,054 A   12/1961   Richter
3,726,929 A   4/1973    Payne et al.
4,001,341 A   1/1977    Welch et al.
4,067,913 A   1/1978    Michniak
4,559,109 A   12/1985   Lee et al.
5,648,562 A   7/1997    Henrick
2009/0137848 A1   5/2009   Fetsko et al.
2018/0179132 A1*  6/2018   Ahn .................. C07C 51/09

FOREIGN PATENT DOCUMENTS

CN   103012124 B   3/2015
PL   85546 B2      1/1976
WO   2015177093 A1  11/2015

OTHER PUBLICATIONS

International Search Report and Written Opinion, PCT/US2017/064424, dated Feb. 20, 2018, 9 pages.
Extended European Search Report issued in 17878493.0, dated Jul. 7, 2020, 6 pages.

* cited by examiner

PROCESSES FOR PURIFICATION, RECOVERY, AND CONVERSION OF CHLOROPHENOL SALTS AND PREPARATION AND RECOVERY OF PRODUCTS PREPARED THEREFROM

REFERENCE TO RELATED APPLICATIONS

The present application is the 371 National Stage Application of International Patent Application Serial No. PCT/US2017/064424, filed Dec. 4, 2017, which claims the benefit of U.S. Provisional Application Ser. No. 62/431,205, filed Dec. 7, 2016, the entire contents of which are incorporated herein by reference.

FIELD OF THE INVENTION

The present invention generally relates to processes for purification, recovery, and conversion of chlorophenol salts (e.g., 2,5-dichlorophenol and/or salts thereof). In various aspects, the present invention is related to removing one or more impurities from chlorophenol salt-containing process streams and/or recovering chlorophenol salts from process streams for use of the recovered chlorophenol elsewhere in an integrated process. Process streams that may be treated in accordance with the present invention include those incorporating one or more chlorophenol salts in a feed mixture and also those where one or more chlorophenol salts are present in a product or by-product stream of an integrated process. For example, conversion processes of the present invention are suitable as one piece of an integrated process for producing 3,6-dichloro-2-methoxybenzoic acid (dicamba) or a salt or ester thereof or a process for producing 2,4-dichlorophenoxyacetic acid (2,4-D) or a salt or ester thereof. The present invention further relates to processes for preparation, purification, and recovery of intermediates formed in integrated processes utilizing chlorophenol salts such as 2,5-dichlorophenol and/or a salt thereof as starting material, including the intermediate 3,6-dichlorosalicylic acid (3,6-DCSA) formed during preparation of dicamba from 2,5-dichlorophenol.

BACKGROUND OF THE INVENTION

Dichlorophenols are useful intermediates in the preparation of a variety of chemical products, including certain herbicides. For example, 2,4-D can be prepared from 2,4-dichlorophenol (2,4-DCP). See, for example, U.S. Pat. Nos. 2,480,817 and 2,651,659. Also, dicamba can be prepared from 2,5-dichlorophenol (2,5-DCP). See, for example, U.S. Pat. Nos. 3,013,054 and 5,648,562.

Difficulties remain in processes for efficiently producing dicamba, including high raw material cost, low process conversions and selectivities, and large amounts of waste are problems that can exist in these processes. The 2,5-dichlorophenol (2,5-DCP) starting material is expected to significantly contribute to high raw material costs. Accordingly, there remains a need for improved processes in the production and separation of critical starting material and intermediates to dicamba, including 2,5-DCP and/or a salt thereof and/or 3,6-DCSA and/or a salt thereof to improve process economics.

Also, starting materials and/or intermediate process streams may include 2,5-DCP and/or a salt thereof in a mixture of dichlorophenols and other impurities. Purifying 2,5-DCP feed mixtures provides a relatively pure stream suitable for the production of dicamba. Also, recovery of unreacted 2,5-DCP and/or a salt thereof from intermediate product mixtures for preparing the dicamba intermediate 3,6-dichlorosalicylic acid (3,6-DCSA) is also important to improve process economics.

BRIEF SUMMARY OF THE INVENTION

In certain aspects, the present invention is directed to processes for dehydrating a chlorophenol salt feed mixture. In certain embodiments, the process comprises providing a feed mixture comprising a chlorophenol salt, water, and an organic solvent; distilling the feed mixture within a distillation zone, thereby forming an overheads fraction comprising water and a portion of the organic solvent and a bottoms fraction comprising the chlorophenol salt and a portion of the organic solvent, the bottoms fraction being enriched in chlorophenol salt as compared to the overheads fraction; condensing the overheads fraction to form a recycle stream comprising recovered organic solvent and water; removing water from the recycle stream; and feeding the recycle stream comprising recovered organic solvent to the distillation zone.

The present invention is also directed to processes for preparation and recovery of 3,6-dichlorosalicylic acid (3,6-DCSA) and/or a salt thereof. In certain embodiments, the process comprises carboxylating 2,5-dichlorophenol (2,5-DCP) and/or a salt thereof in an organic reaction medium comprising an organic solvent, thereby forming a carboxylation product slurry comprising the organic solvent, 3,6-DCSA and/or one or more salts thereof, unreacted 2,5-DCP and/or a salt thereof, and one or more impurities; feeding the carboxylation product slurry to a fractional liquid-liquid extraction (FLLE) zone; feeding an organic solvent to the FLLE zone; feeding an aqueous medium to the FLLE zone; contacting the carboxylation product slurry with the organic solvent and the aqueous medium in the FLLE zone, wherein at least a portion of the unreacted 2,5-DCP and/or a salt thereof and the one or more impurities are transferred to an organic phase comprising the organic solvent and at least a portion of the 3,6-DCSA or a salt thereof is transferred to an aqueous phase; recovering an aqueous phase extract comprising one or more salts of 3,6-DCSA from the FLLE zone, wherein the weight ratio of salts of 3,6-DCSA to 2,5-DCP in the aqueous phase extract is greater than the weight ratio of salts of 3,6-DCSA to 2,5-DCP in the carboxylation feed mixture; recovering an organic phase extract comprising 2,5-DCP, the organic solvent and one or more impurities from the FLLE zone; and neutralizing the salts of 3,6-DCSA in the aqueous phase extract to form a product mixture comprising 3,6-DCSA.

The present invention is also directed to processes for recovery of 2,5-dichlorophenol (2,5-DCP) and/or a salt thereof. In certain embodiments, the process comprises carboxylating 2,5-DCP and/or a salt thereof in an organic reaction medium comprising an organic solvent, thereby forming a product mixture in the organic solvent comprising 3,6-dichlorosalicylic acid and one or more salts thereof, unreacted 2,5-DCP and/or salts thereof, one or more salts of 2,5-DCP, and one or more dimers of 2,5-DCP; feeding the product mixture to an extraction zone; feeding an organic solvent to the extraction zone; feeding an aqueous medium to the extraction zone; contacting the product mixture with the organic solvent and the aqueous medium in the extraction zone, wherein at least a portion of the unreacted 2,5-DCP and dimers of 2,5-DCP are transferred to an organic phase comprising the organic solvent and one or more salts of 2,5-DCP are transferred to an aqueous phase, wherein the aqueous phase is enriched in 3,6-dichlorosalicylic acid and salts of 2,5-DCP relative to the product mixture and the organic phase is enriched in unreacted 2,5-DCP as compared to the product mixture; removing an organic extract comprising the organic phase from the extraction zone; recovering 2,5-dichlorophenol from the organic phase, and wherein recovered 2,5-DCP is fed to an extraction zone for recovery of impurities therefrom and/or fed to a carboxylation reactor for production of 3,6-dichlorosalicylic acid.

The present invention is further directed to processes for purifying chlorophenol salt-containing feed mixtures. In certain embodiments, the present invention is directed to processes for removing impurities from a feed mixture comprising 2,5-dichlorophenol (2,5-DCP) and/or a salt thereof, the processes comprising heating the 2,5-DCP feed mixture to a temperature of at least about 25° C., the 2,5-DCP feed mixture comprising an organic solvent, 2,5-DCP, 2,5-dichloro-4-nitrophenol (2,5-DCNP), and a plurality of chlorophenol dimers; feeding the 2,5-DCP feed mixture into a first extraction zone; contacting the feed mixture within the first extraction zone with a first aqueous solution comprising a base, thereby forming a first organic phase extract comprising the organic solvent, 2,5-DCP and the plurality of chlorophenol dimers and forming a first aqueous phase extract comprising 2,5-DCNP and/or salts thereof, the first aqueous phase extract being enriched in 2,5-DCNP and/or salts thereof as compared to the first organic phase extract and the 2,5-DCP feed mixture; feeding the first organic phase extract into a second extraction zone and contacting the first organic phase extract with a second aqueous solution comprising a base, thereby forming a second organic phase extract comprising the chlorophenol dimers and forming a second aqueous phase extract comprising 2,5-DCP and/or salts thereof, the second organic phase extract enriched in the chlorophenol dimers as compared to the first organic phase extract and the second aqueous phase extract enriched in 2,5-DCP as compared to the first organic phase extract.

The present invention is further directed to processes for preparation of dicamba and/or a salt thereof incorporating one or more of the processes described above and detailed herein.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE INVENTION

Figure 1:
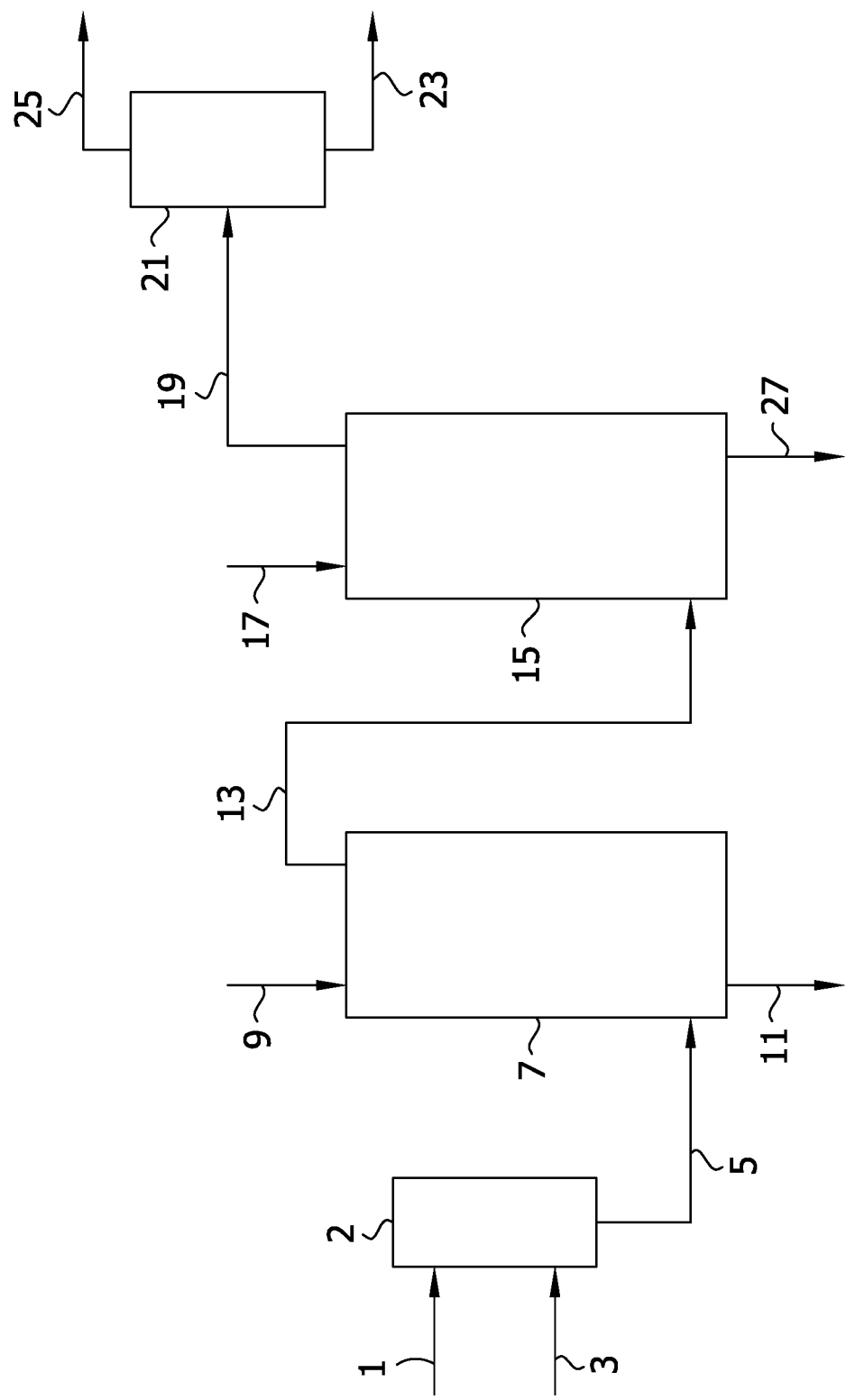
FIG. 1 provides a schematic for a process for purifying a 2,5-DCP feed mixture in accordance with the present invention.

The present invention involves processes and unit operations useful in the preparation of dicamba from 2,5-DCP. The present invention includes processes for purification, recovery, and conversion of chlorophenol salts (e.g., 2,5-dichlorophenol, including the potassium salt thereof). The conversion of chlorophenol salts includes preparation of dicamba from 2,5-DCP starting material. The present invention further relates to processes for preparation, purification, and recovery of intermediates formed in integrated processes utilizing chlorophenol salts such as 2,5-dichlorophenol as starting material, including the intermediate 3,6-dichlorosalicylic acid (3,6-DCSA) formed during preparation of dicamba from 2,5-DCP.

2,5-DCP Feed Mixtures

The present invention involves processes and unit operations for treatment of a variety of feed mixtures comprising 2,5-DCP and/or a salt thereof.

Certain 2,5-DCP feed mixtures include one or more impurities or components that may interfere with or lower yield of processes using the 2,5-DCP as starting material including, for example, 2,5-DCNP, and one or more chlorophenol dimers. Such a feed mixture may be referred to as "crude" and may be treated by certain processes detailed herein (e.g., the purification and dehydration processes detailed herein).

Exemplary feed mixture compositions include: (i) 2,5-DCP in a proportion of from about 15 wt % to about 40 wt %, from about 15 wt % to about 35 wt %, or from about 15 wt % to about 25 wt %, (ii) 2,5-dichloronitrophenol (2,5-DCNP) in a proportion of up to about 1 wt %, (iii) 3-chlorophenol (3-CP) in a proportion of up to about 2 wt %, (iv) 1,4-dichlorobenzene (1,4-DCB) in a proportion of up to about 1 wt %, and/or (v) 1,2,4-trichlorobenzene (1,2,4-TCB) in a proportion of up to about 1 wt %.

2,5-DCP feed mixtures either as-provided or recovered from other unit operations (e.g., the carboxylation to 3,6-DCSA as discussed elsewhere herein) also may include one or more dimers of 2,5-DCP. These dimers may include meta-(chloro-(2,5dichlorophenoxy)phenol) (meta-CDPP) and ortho-(chloro-(2,5dichlorophenoxy)phenol) (ortho-CDPP).

Further exemplary compositions of DCP feed streams recovered from elsewhere in an integrated process may include 2,5-DCP in a proportion of from about 5 to about 20 wt %, and one or more of the following impurities at differing concentrations, but generally at a concentration of no more than about 1 wt %, or no more than about 0.5 wt %: 3-CP, 1,4-DCB, 1,2,4-TCB, meta-CDPP, and/or ortho-CDPP Additionally or alternatively, the feed mixture or a portion thereof can be obtained from an isomerization process where 2,4-dichlorophenol is isomerized to 2,5-dichlorophenol. In such instances, the feed mixture or a portion thereof may be a 2,5-DCP and/or salt thereof-containing stream that has been treated in accordance with any of the processes described in U.S. Provisional Application Ser. No. 62/170, 300; and International Application No. PCT/US2016/034954, which describe processes for the separation of dichlorophenols and are hereby incorporated by reference for all relevant purposes.

Purifying 2,5-DCP Mixtures

The following discussion concerns purification of a 2,5-DCP-containing process stream with details of at least one embodiment depicted in FIG. 1. As used herein, when referring to "2,5-DCP" or a "2,5-DCP-containing stream" it is to be understood that this contemplates 2,5-DCP and/or one or more salts thereof. It is to be further understood that while the following discussion focuses on 2,5-DCP and/or salts thereof, the processes of the present invention are likewise suitable for use in connection with other chlorophenol salts (e.g., 2,4-DCP and/or salts thereof).

2,5-DCP-containing process streams treated in accordance with the following description generally include the DCP starting material (e.g., 2,5-DCP or a salt thereof prepared or provided for use in a carboxylation reaction to produce 3,6-DCSA), or recovered from one or more points in an integrated process that includes carboxylation of 2,5-DCP and/or a salt thereof to produce 3,6-DCSA, which may further include preparation of dicamba. For example, a chlorophenol salt-containing feed stream as recovered from the process described in connection with FIG. 3 detailed elsewhere herein may be treated by the following method described with reference to FIG. 1 to remove one or more impurities. The purification methods detailed herein are also suitable for purification of 2,5-DCP feed streams as-supplied.

Generally, with reference to FIG. 1 a 2,5-DCP feed mixture 1 is first treated in a carbon dioxide ($CO_2$) stripper 2 by contact with a nitrogen-containing gas stream 3 to provide a 2,5-DCP feed mixture 5 that is introduced into extraction zone 7. Generally, the target $CO_2$ content of the feed mixture is less than about 1000 ppm or less than about 100 ppm. Where the feed stream provided or recovered meets this limit, use of the carbon dioxide stripper is not required and the 2,5-DCP feed mixture 5 is introduced directly into extraction zone 7.

Generally, feed mixture 5 includes certain phenolic compounds, including 2,5-DCP, 2,5-DCNP, and 3-CP. Other impurities present in the crude feed mixture to be removed include the following chlorophenol dimers: meta-(chloro-(2,5dichlorophenoxy)phenol) (meta-CDPP) and ortho-(chloro-(2,5dichlorophenoxy)phenol) (ortho-CDPP).

As shown in FIG. 1, 2,5-DCP feed mixture 5 is introduced into extraction zone 7 where it is contacted with an aqueous basic solution 9. The purpose of this first extraction is removal of the phenolic impurities. Generally, the phenolic compounds are partitioned to an aqueous phase 11 that is removed from the extraction zone as a waste stream and the 2,5-DCP (and dimers thereof) are partitioned to the organic extract 13 that is removed from the extraction zone.

Generally, the aqueous basic solution comprises an alkali or alkaline earth hydroxide, carbonate, or bicarbonate. For example, the base may be selected from the group consisting of potassium hydroxide, sodium hydroxide, and mixtures thereof.

Extraction zone 7 is typically in the form of an apparatus suitable for countercurrent liquid-liquid extraction including, for example, KARR columns and SCHEIBEL columns. Typically, the extraction zone comprises at least 10 stages, at least 15 stages, at least 20 stages, or at least 25 stages.

Without being bound by theory, it has been discovered for this first basic extraction method that where the molar ratio of base (e.g., KOH) to 2,5-DCP exceeds 1.0:1 that, all the phenolic compounds (e.g., 2,5-DCP, 2,5-DCNP, and 3-CP) are sufficiently, and typically completely extracted to the aqueous layer; while the non-phenolic compounds (e.g., 1,4-DCB and 1,2,4-TCB) remain in the organic layer. Typically, the molar ratio of base to 2,5-DCP is at least about 0.5:1, at least about 0.6:1, at least about 0.7:1, at least about 0.8:1, or at least about 0.9:1. Additionally or alternatively, in certain embodiments, the molar ratio of base to 2,5-DCNP present in the feed mixture is from about 0.5:1 to about 5:1, from about 0.5:1 to about 3:1, from about 0.5:1 to about 2:1, or from about 0.5:1 to about 1.5:1.

Suitable base concentrations for this extraction step include from about 0.01 wt % to about 2 wt %, from about 0.05 wt % to about 1 wt %, from about 0.1 wt % to about 1 wt %, or from about 0.2 wt % to about 1 wt %.

Generally, the organic phase extract contains at least about 90 wt %, at least about 95 wt %, or at least about 99 wt % of the 2,5-DCP present in the feed mixture.

Typically at least about 50 wt %, at least about 75 wt %, or at least about 95 wt % of the phenolic compounds present in the feed mixture are removed by partitioning to the aqueous phase that is removed from the extraction zone.

Again with reference to FIG. 1, organic phase extract 13 recovered from the first extraction zone is introduced into a second extraction zone 15. This extract includes the following impurities present in the feed mixture to be removed, in particular the following chlorophenol dimers: meta-(chloro-(2,5dichlorophenoxy)phenol) (meta-CDPP) and ortho-(chloro-(2,5dichlorophenoxy)phenol) (ortho-CDPP). Removal of these impurities improves efficiency and yield of downstream processes for converting 2,5-DCP.

Extraction of the dimers using a second basic solution 17 introduced into the second extraction zone generally proceeds in accordance with the extraction of the phenolic compounds described above also utilizing a suitable column for countercurrent liquid-liquid extraction and the one of the bases listed above. However, it has been observed that a more concentrated basic solution provides more effective partitioning of the dimers to the organic phase and recovery of the 2,5-DCP in an aqueous extract. Therefore, generally the concentration of the base in the aqueous solution for the second extraction is from about 1 wt % to about 45 wt %, from about 5 wt % to about 40 wt %, or from about 5 wt % to about 30 wt %. In certain embodiments, the concentration of the base in the aqueous solution for this second extraction step is from about 5 wt % to about 20 wt %, from about 7 wt % to about 15 wt %, from about 7 wt % to about 12 wt %, or from about 10 wt % to about 12 wt %.

Generally, the pH of the second aqueous phase extract is at least about 7.1, at least about 8, at least about 9, at least about 10, at least about 11. Typically, the pH of the second aqueous phase extract is from about 7.1 to about 13, from about 8 to about 12, from about 10 to about 12 (e.g., about 11).

Generally, the molar ratio of base to 2,5-DCP and/or a salt thereof is at least about 0.5:1, at least about 0.6:1, at least about 0.7:1, at least about 0.8:1, at least about 0.9:1, at least about 1.0:1, or at least about 1.1:1 for this second extraction step. Typically for this second extraction step, the molar ratio of base to 2,5-DCP and/or a salt thereof is from about 0.5:1 to about 1.5:1, from about 0.7:1 to about 1.1:1, from about 0.7:1 to about 1.0:1, or from about 0.7:1 to about 0.9:1. In certain embodiments, the molar ratio is near 1:1 (e.g., about 0.8:1, about 0.9:1, or about 1.0:1).

This second extraction results in organic extract 19 containing at least about 50 wt %, at least about 60 wt %, at least about 70 wt %, or even higher, of the dimers from the organic extract introduced into the second extraction zone. This organic extract 19 may be introduced into distillation zone 21 that produces a bottoms 23 and overheads fraction 25 comprising xylene and having the higher-boiling 2,5-DCP dimers removed therefrom.

Also produced is aqueous extract 27 having the 2,5-DCP dimers removed therefrom and containing at least about 90 wt % of the 2,5-DCP introduced in the second extraction zone. Overall, the aqueous phase extract contains at least about 95 wt % 2,5-DCP and a minor portion of phenolic and/or dimer impurities (e.g., no more than about 0.5 wt % or no more than about 0.1 wt %).

FIG. 1 shows two extraction steps with the purpose of the first extraction step being removal of the phenolic impurities. In certain embodiments, the 2,5-DCP feed mixture may not contain a fraction of phenolic impurities requiring removal. In such instances, the first extraction step is optional and feed mixture 5 would be fed directly to second extraction zone 17 for the lone extraction step.

Overall, the extraction process depicted in FIG. 1 provides a 2,5-DCP feed mixture having undesired phenolic impurities removed therefrom and also having one or more 2,5-DCP dimers removed therefrom. Contact of the 2,5-DCP with the basic solution forms an aqueous extract comprising a salt of 2,5-DCP formed by neutralizing the 2,5-DCP with the base in the countercurrent liquid-liquid extraction. Typically, therefore, aqueous phase extract from the liquid-liquid extraction contains at least about 20 wt %, at least about 25 wt %, or at least about 30 wt % of 2,5-DCP and/or a salt thereof. The other major component of the aqueous extract is water.

Dehydrating 2,5-DCP Feed Mixtures

As detailed elsewhere herein, the potassium salt of 2,5-DCP is carboxylated to form 3,6-DCSA, which is a an intermediate in the preparation of dicamba. Generally, the 2,5-DCP feed mixture (either provided as-is or subjected to the method of FIG. 1) is contacted with a basic solution to neutralize any remaining 2,5-DCP and form the 2,5-DCP salt feed mixture.

A negative correlation between increasing water content of the 2,5-DCP carboxylation feed and 3,6-DCSA intermediate yield has been observed. Therefore, water content of the 2,5-DCP carboxylation feed is an important feature. Detailed herein are strategies to reduce the water content of these 2,5-DCP salt feed streams.

Figure 2:
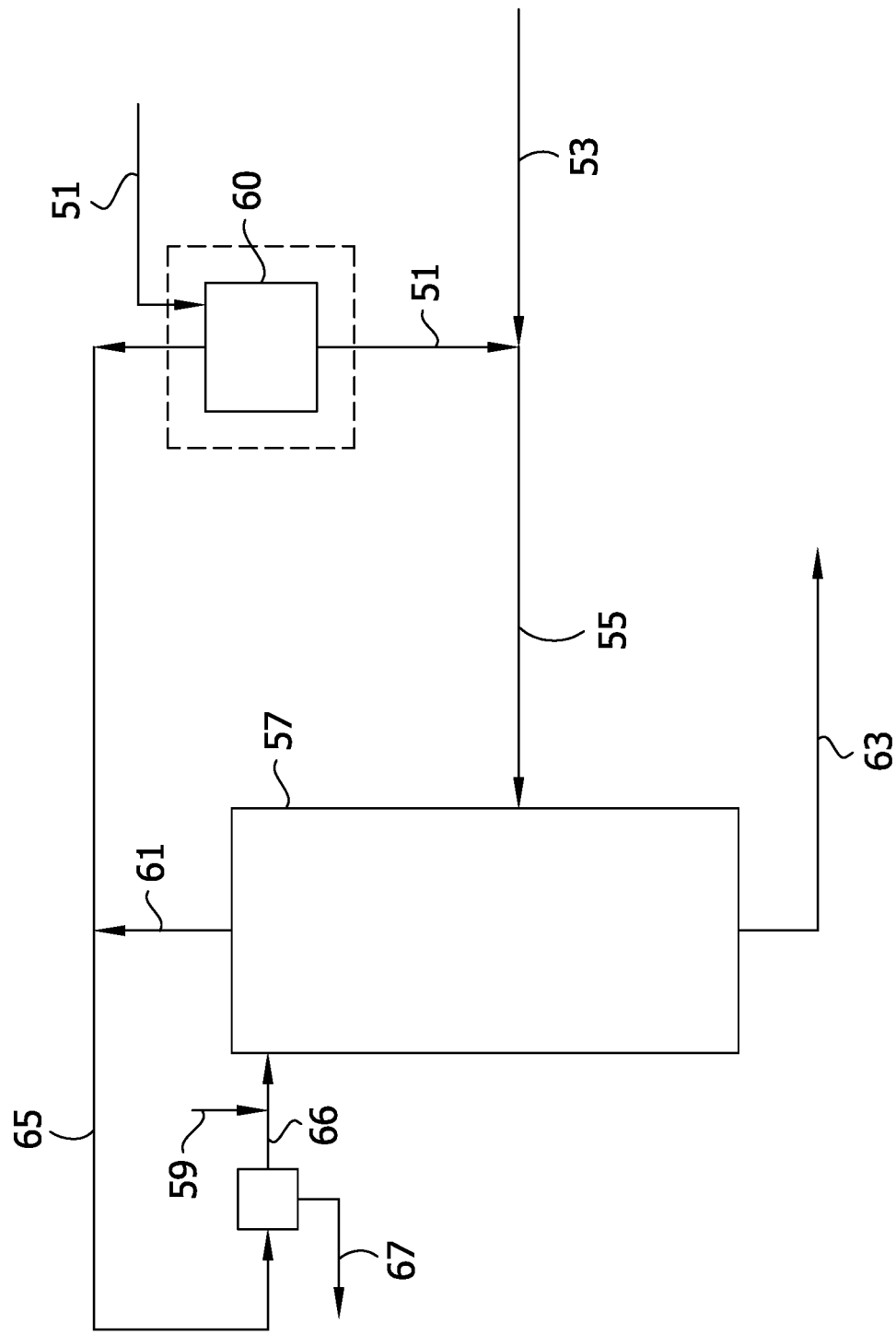
FIG. 2 provides a schematic for a process for dehydrating a feed mixture in accordance with the processes of the present invention.

With reference to FIG. 2, generally a 2,5-DCP salt feed stream 51 is combined with an organic solvent 53 to form a stream 55 that is introduced into the distillation zone 57.

Figure 5:
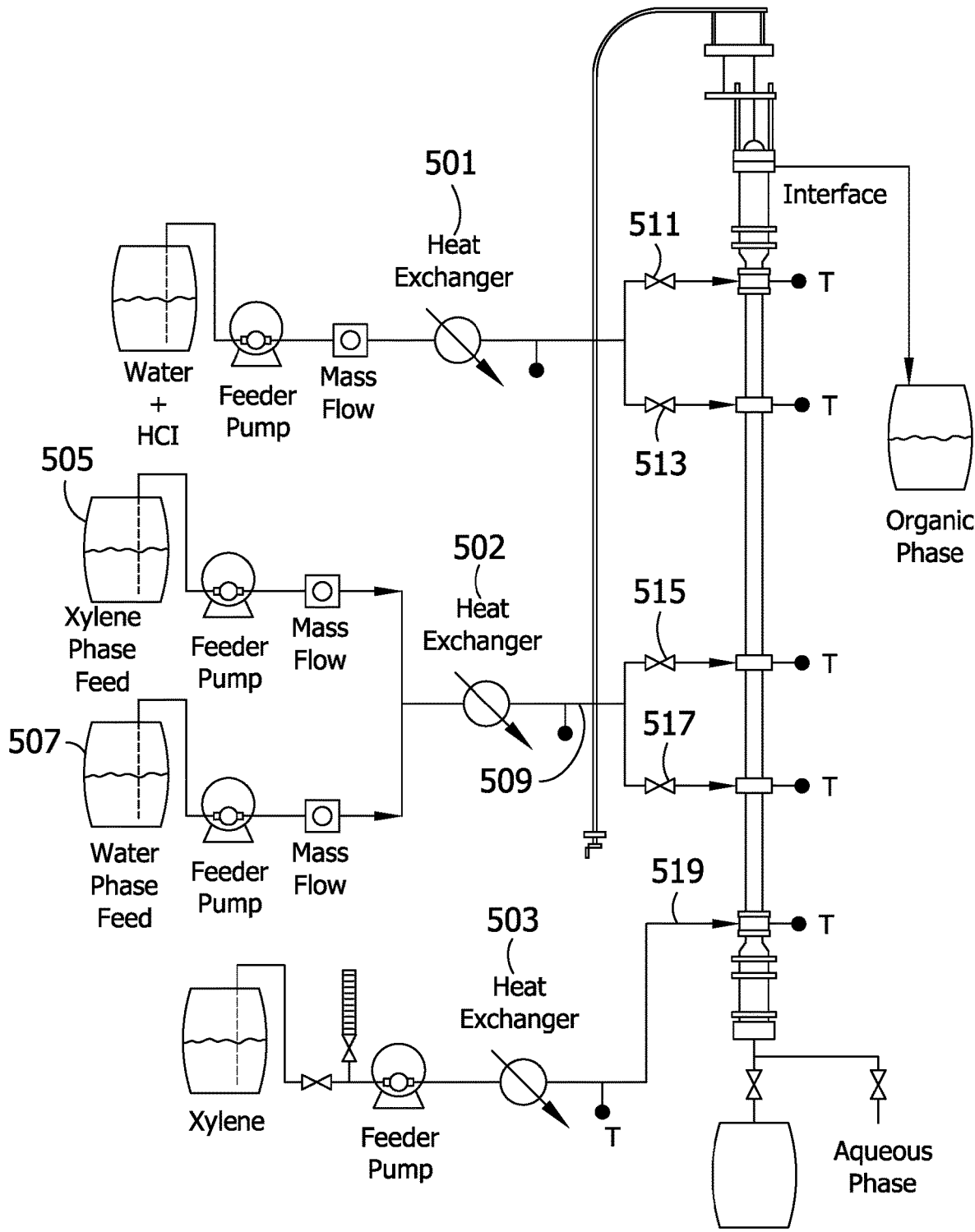
FIG. 5 provides details of a system used in the processes described in Examples 11-15.

In certain embodiments, excess water is removed from the 2,5-DCP feed mixture 51 prior to its combination with the organic solvent and introduction into the distillation zone. For example, as shown in FIG. 5 water may be removed from the 2,5-DCP feed mixture in flash evaporator 60 (shown as optional in FIG. 2).

Generally, the feed mixture 55 to be distilled is introduced into a section of the distillation zone and contacted with organic solvent 59 that has also been introduced into a section of the distillation zone.

In certain embodiments, distillation zone 57 comprises a plurality of actual or theoretical stages and includes a rectifying section and a stripping section, with an intermediate section between these two sections. For example, the distillation zone may comprise a plurality of actual or theoretical stages that may be referred to as intermediate stages where the rectifying zone comprises one or more stages above the intermediate stages of the distillation zone and the stripping section comprises one or more stages below the distillation zone. In such embodiments, the feed mixture may be introduced into the intermediate section of the distillation zone.

FIG. 2 depicts a vertical column. In such instances the rectifying zone would generally exist above the feed location while the stripping zone would generally exist below the feed location. However, it is to be understood that reference to a rectifying zone or stripping zone does not necessarily indicate a physical location within a column or other apparatus, but more generally describes the mass transfer phenomena occurring within a particular portion or region of the column or other apparatus.

Figure 10:
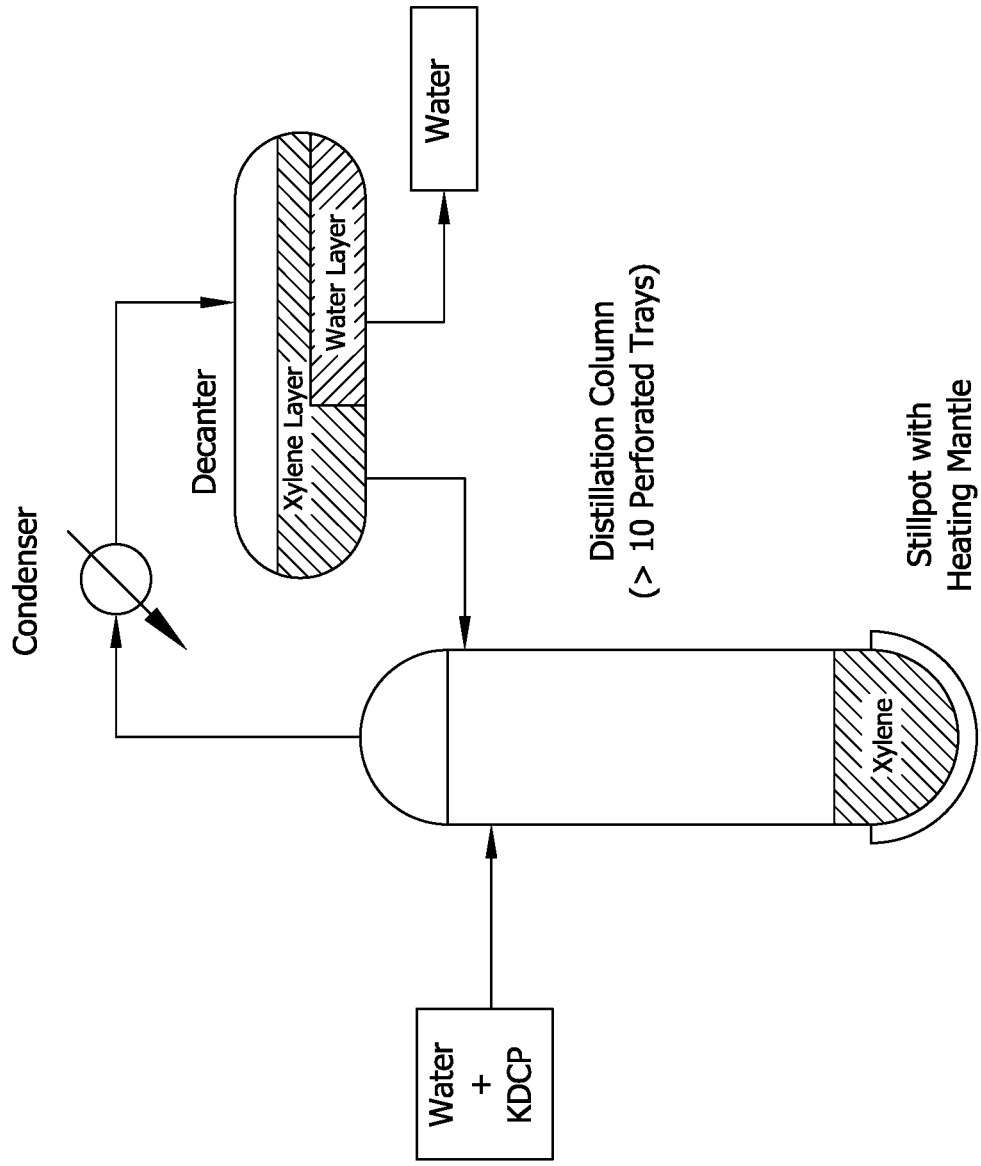
FIG. 10 depicts a dehydration column and associated equipment for use in the process described in Example 20.

Generally in accordance the present methods a mixture comprising the chlorophenol salt, water, and organic solvent is present within the distillation zone. This may be achieved by feeding, or providing to the distillation zone a mixture comprising these three components generally as depicted in FIG. 2. Alternatively, the feed mixture of the distillation zone may be provided by first introducing the organic solvent into the distillation zone and then combining a mixture of the chlorophenol salt and water (i.e., an intermediate feed mixture) with the organic solvent within the distillation zone. Typically in accordance with such embodiments, the organic solvent within the distillation zone is heated to a temperature of at least about 60° C., at least about 70° C., at least about 80° C., or at least about 90° C. Such a process is generally depicted in FIG. 10 and described in Example 20. Generally, therefore, it is to be understood that providing the feed mixture for the distillation zone involves combining the organic solvent with a water/DCP salt-containing mixture outside and/or within the distillation zone.

In certain embodiments, the temperature of an intermediate feed mixture combined with the organic solvent is at least about 30° C., at least about 60° C., at least about 90° C., at least about 120° C., or at least about 150° C. The temperature of an intermediate feed mixture can also be from about 30° C. to about 200° C., from about 60° C. to about 200° C., from about 90° C. to about 200° C., from about 120° C. to about 200° C., or from about 150° C. to about 200° C.

Typically, the mass ratio of organic solvent to chlorophenol salt in the feed mixture is from about 0.2:1 to about 3:1, from about 0.5:1 to about 2.5:1, or from about 1:1 to about 2:1.

Typically, the mass ratio of water to chlorophenol salt in the feed mixture is from about 0.2:1 to about 2:1, from about 0.2:1 to about 1:1, or about 0.5:1.

Non-limiting examples of organic solvents suitable for use in connection with the process described herein include $C_5$-$C_{10}$ alkane solvents, $C_1$-$C_{10}$ halogenated alkane solvents, $C_0$-$C_{10}$ alkylbenzenes, halogenated aromatic solvents, dialkyl ether solvents of the general formula R—O—R', wherein R and R' are each independently selected from $C_2$-$C_6$ alkyl, and ester solvents of the formula R—C(O)O—R' wherein R and R' are each independently selected from $C_2$-$C_6$ alkyl.

In some embodiments, the organic solvent comprises a $C_5$-$C_{10}$ alkane compound. The compound may comprise one or more $C_5$-$C_{10}$ linear, branched or cyclic alkyl groups. By way of non-limiting example, the organic solvent may comprise hexane, 2-methylhexane, or cyclohexane.

In some embodiments, the organic solvent comprises a $C_1$-$C_{10}$ halogenated alkane solvent. The compound may comprise one or more $C_1$-$C_{10}$ linear, branched or cyclic alkyl groups. In some embodiments, the compound may comprise one or more halogen substituents independently selected from F, Cl, and Br. For example, the compound may comprise from one to six halogen substituents. By way of non-limiting example, the organic solvent may comprise dichloromethane, dichloroethane, chloroform, or carbon tetrachloride.

In some embodiments, the organic solvent comprises a $C_0$-$C_{10}$ alkylbenzene compound. The compound may comprise one or more $C_1$-$C_{10}$ linear, branched or cyclic alkyl groups, each of which may be optionally independently substituted with one or more halogen substituents independently selected from F, Cl, and Br. For example, the compound may comprise from one to six halogen substituents. In some embodiments, the alkyl groups are saturated alkyl groups. By way of non-limiting example, the organic solvent may comprise toluene, o-xylene, p-xylene, m-xylene, xylenes, trimethylbenzene, or trifluorotoluene. In certain embodiments, the solvent is selected from the group consisting of xylene, toluene, benzene, and combinations thereof.

In some embodiments, the organic solvent comprises a halogenated aromatic compound comprising one or more halogen substituents independently selected from F, Cl, and Br. For example, the compound may comprise from one to six halogen substituents. By way of non-limiting example, the organic solvent may comprise chlorobenzene, dichlorobenzene, chlorotoluene, or hexafluorobenzene.

In some embodiments, the organic solvent comprises a compound of the formula R—O—R' wherein R is selected from $C_4$-$C_6$ cycloalkyl and R' is methyl. For example, the organic solvent may comprise cyclopentyl methyl ether.

In other embodiments, the organic solvent comprises a compound of the formula R—O—R' wherein R and R' are each $C_3$-$C_6$ alkyl. For example, the organic solvent may comprise dibutyl ether. In such embodiments, dibutyl ether forms peroxides at a much slower rate as compared to other ethereal solvents.

In further embodiments, the organic solvent may comprise an ester compound of the formula R—C(O)O—R' wherein R and R' are each independently selected from $C_1$-$C_6$ alkyl. For example, the organic solvent may comprise ethyl acetate, isopropyl acetate, butyl acetate, or isobutyl acetate.

In certain embodiments, the organic solvent and water of the feed mixture form an azeotropic feed mixture and produces an overheads fraction 61 that comprises a minimum boiling azeotrope comprising the organic solvent and water. In such instances the overheads fraction therefore boils at a temperature lower than any ratio of the constituents of the overheads fraction.

In certain embodiments, the distillation zone may be operated under reduced pressure (e.g., below atmospheric pressure) in order to promote boiling at lower temperatures and recovery of the overheads fraction comprising the organic solvent that is then returned to the distillation zone. Operation under reduced pressure may be advantageous where the distillation zone is not heated or is not heated to any significant degree.

Along with the overheads fraction (e.g., the minimum boiling azeotrope of the organic solvent and water) removed from the distillation zone, a 2,5-DCP salt bottoms stream 63 is removed from the distillation zone as well.

As noted, the goal of the dehydration process is to provide a 2,5-DCP containing stream useful for the carboxylation reaction to form 3,6-DCSA. The product of the dehydration as the bottoms product recovered from the distillation typically contains less than about 0.1 wt % water, less than about 0.05 wt % water, less than about 0.02 wt % water, less than about 0.01 wt % water, less than about 0.005 wt % water, or less than about 0.001 wt % water.

Generally, the bottoms fraction contains a chlorophenol salt-organic solvent mixture. The chlorophenol salt typically contains at least about 10 wt %, at least about 20 wt %, or at least about 30 wt % of the bottoms fraction with the remainder constituted by the organic solvent.

Various features of operation of the distillation zone and/or the compositions of the streams within the distillation zone conduce removal of a significant fraction of water from the 2,5-DCP salt feed mixture and forming the desired dehydrated feed mixture.

For example, as shown in FIG. 2, overheads fraction 61 is condensed to form an aqueous recycle stream 65 and water 67 is removed from the condensed overheads fraction in a suitable vessel and recovered organic solvent 66 is combined with organic solvent 59 and introduced into the rectifying section. Water is typically removed from the recycle stream by a liquid-liquid separation method selected from the group consisting of decanting, extraction, mixing/settling, and centrifugation. After a phase-in period, the distillation zone (i.e., column) is preferably operated such that the overheads fraction is removed from the distillation zone while at the same time the recycle stream is fed to the rectifying zone and in this manner the column is operated under reflux conditions.

Preparation of 3,6-DCSA

As noted, 2,5-DCP and/or a salt thereof may be supplied for use in preparation of dicamba or may be prepared by a method known in the art and therefore may be considered as the starting material for the preparation of dicamba. In another aspect, 2,5-DCP and/or a salt thereof is prepared in an integrated process (e.g., by a process as noted above) for the preparation of dicamba and therefore may be considered as an intermediate. In any case, 2,5-DCP and/or a salt thereof is generally used to prepare the dicamba intermediate 3,6-dichlorosalicyclic acid (3,6-DCSA) and/or a salt thereof.

Along with the 3,6-DCSA product, the carboxylation product mixture typically contains unreacted 2,5-DCP and/or salts thereof and one or more impurities. Purification of this product mixture is desired both in terms of providing a 3,6-DCSA product of the desired purity and also recovering unreacted 2,5-DCP and/or salts thereof that can be recycled to improve process economics. Accordingly, the processes described herein are properly referred to as processes for preparation and recovery of 3,6-DCSA and/or processes for recovery of 2,5-DCP. One embodiment of such a process of the present invention is shown in FIG. 3.

Carboxylation product slurry 100 typically includes the 3,6-DCSA product, unreacted 2,5-DCP and other impurities, including salts of 2,5-DCP (e.g., the potassium salt of DCP) and various dimers of 2,5-DCP. Generally, the water content of the carboxylation product slurry is less than about 1 wt %, less than about 0.7 wt %, less than about 0.5 wt %, less than about 0.2 wt %, less than about 0.1 wt %, less than about 0.05 wt %, less than about 0.02 wt %, or less than about 0.01 wt %. In certain embodiments, to aid in downstream processing a small portion of water may be added to the product slurry to provide a water content of the slurry of, for example, of up to about 10 wt % (e.g., from 5 to about 10 wt %). However, it is to be understood that addition of water to the product slurry is not required in accordance with the present invention, including processes such as the process depicted in FIG. 3.

Generally, the 2,5-DCP containing feed stream contains a minor portion of carbon dioxide ($CO_2$) that is neutralized to form potassium carbonate ($K_2CO_3$) and/or potassium bicarbonate ($KHCO_3$).

Figure 3:
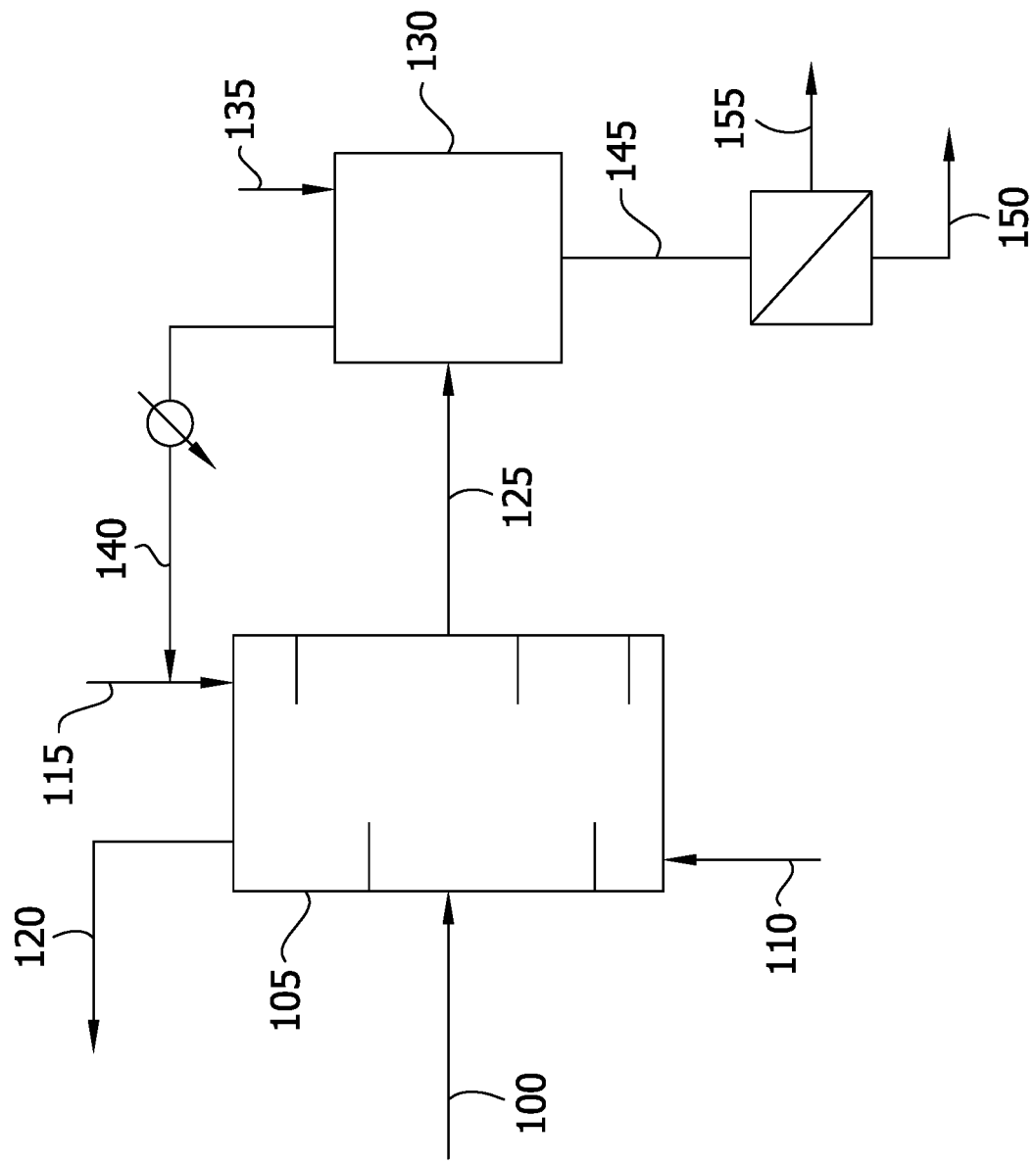
FIG. 3 provides a schematic for a process for extraction of 3,6-DCSA in accordance with the processes of the present invention.

As shown in FIG. 3, the product slurry is fed to a fractional liquid-liquid extraction (FLLE) zone. The FLLE zone may be in the form of a column, a mixer or a settler. As shown in FIG. 3, the FLLE zone comprises a column into which the product slurry is introduced at a feed location. Also introduced in the FLLE zone is an organic solvent 110 and aqueous phase 115.

FIG. 3 generally depicts a vertical column, but it is to be understood that a vertical column is not required. For example, one or more mixers or settlers may be utilized for recovery of the desired organic and aqueous phases. In such instances a plurality of mixers/settlers may be arranged in a serial arrangement to provide the desired organic phase extract and aqueous phase extract. In particular, it is to be understood that such methods that do not involve a column for the FLLE zone may be combined with the other methods detailed herein (e.g., the purifying and dehydration processes described herein).

In certain embodiments, the FLLE zone includes a stripping zone, or section and a rectifying zone, or section. Generally, a rectifying zone would be above (in a vertical direction along the length of the column) the feed location for the product slurry while the stripping section generally would be below (also in a vertical direction along the length of the column) the feed location for the product slurry. However, it is to be understood that reference to a rectifying section or stripping section does not necessarily require a particular location within the FLLE zone (e.g., above or below the feed location). Rather, reference to such a section or zone most generally denotes the mass transfer phenomenon occurring within that portion of the apparatus utilized for the extraction.

In various embodiments, including the embodiment depicted in FIG. 3, the FLLE zone comprises at least one vertical column having a feed location for the carboxylation product slurry with the stripping section present in the portion of the column situated beneath the feed location and the rectifying section present in the portion of the column situated above the feed location.

Generally, when present, the stripping section and rectifying section each comprise a plurality of stages. It has been observed that the feed locations of the organic solvent and aqueous phase may impact column efficiency. Generally, the organic solvent 110 is introduced at the bottom of the column (as shown in FIG. 3), but this stream may also be introduced at point near the bottom of the column and below the feed location. As shown in FIG. 3, the aqueous phase is introduced at the top of the column, and can also be introduced at a point near the top of the column, but nonetheless above the feed location.

In certain embodiments, the organic solvent is introduced into an intermediate stage of the stripping section such that there is at least one stage between the intermediate stripping stage and the feed location and at least one stage of the stripping section between the intermediate stripping stage and the bottom of the column. Likewise, the aqueous solvent may be introduced into an intermediate stage of the rectifying section such that there is at least one stage between the intermediate rectifying stage and the feed location and at least one stage between the intermediate rectifying stage and the top of the column.

In accordance with these and other embodiments, there is at least one stage of the stripping section between the bottom of the column and the feed location of the organic solvent and/or at least one stage of the rectifying section between the top of the column and the feed location of the aqueous medium.

Initially, extraction zone 105 is operated by filling with the aqueous phase, therefore when the organic phase and slurry feed mixture are introduced into the extraction zone, the primary interface between the organic phase and the aqueous phase will at least be above the feed location, and typically near the top of the column.

In certain embodiments, the organic solvent and aqueous medium are introduced into the FLLE zone and contacted to form an FLLE zone having the organic solvent dispersed throughout the aqueous medium, and the carboxylation product slurry is introduced into the FLLE zone having the organic solvent dispersed throughout the aqueous medium.

Generally, contact of the feed mixture with the organic solvent produces an organic phase extract 120 that is removed from the rectifying section and an aqueous phase extract 125 that is recovered from the FLLE zone.

The organic phase is enriched in unreacted 2,5-DCP and one or more impurities while salts of 3,6-DCSA preferentially partition to the aqueous phase. Recovery of the 3,6-DCSA salts in the aqueous phase may be defined in terms of the weight ratio of salts of 3,6-DCSA to 2,5-DCP in the aqueous phase extract being greater than the weight ratio of salts of 3,6-DCSA to 2,5-DCP in the carboxylation feed mixture.

The organic phase extract comprising 2,5-DCP may be treated in accordance with other processes detailed herein (e.g., the 2,5-DCP purification process depicted in FIG. 1).

To provide a product slurry (i.e., the feed mixture to the extraction zone) that does not settle within the column without dispersing throughout the organic and aqueous phases, the carboxylation product slurry may be agitated prior to and/or during introduction into the FLLE zone. This agitation may be conducted by any method generally known in the art. Additionally or alternatively, in certain embodiments it may be advantageous to agitate the FLLE zone to promote contact between the slurry, organic solvent, and aqueous phase. Under certain conditions, extraction of 3,6-DCSA salts to the aqueous phase may increase with agitation of the contents of the FLLE zone, and more particularly may increase as the degree of agitation increases.

Generally, the flow rates for the product slurry, organic solvent, and aqueous phase are selected to provide an extraction zone that provides sufficient interfacial contact between the phases and separation and recovery of the 3,6-DCSA as solids present in the aqueous extract 125 recovered from the extraction zone.

The flow rates, in particular the relative flow rates of the process streams introduced into the extraction zone may also affect partitioning of the components to the aqueous and organic phases within the extraction zone.

Generally, the ratio of the mass flow rates for the aqueous medium to the carboxylation product slurry fed to the FLLE extraction is at least about 1:1, at least about 3:1, at least about 5:1, at least about 7:1, at least about 9:1, or at least about 11:1. Typically, the ratio of the mass flow rates for the aqueous medium to the carboxylation product slurry fed to the FLLE extraction zone is from about 1:1 to about 15:1, from about 3:1 to about 12:1, or from about 5:1 to about 12:1.

Generally, the ratio of the mass flow rates for the organic solvent to the carboxylation product slurry fed to the FLLE extraction is less than about 1:1, less than about 0.9:1, less than about 0.8:1, less than about 0.7:1, less than about 0.6:1, less than about 0.5:1, less than about 0.4:1, less than about 0.3:1, less than about 0.2:1, less than about 0.1:1, or less than about 0.05:1. Typically, the ratio of the mass flow rates for the organic solvent to the carboxylation product slurry fed to the FLLE extraction zone is from about 0.05:1 to about 1:1, from about 0.1:1 to about 0.8:1, or from about 0.2:1 to about 0.5:1.

As noted, within the FLLE zone contact of the organic solvent and aqueous phase results in the organic solvent being dispersed throughout the organic solvent. Typically, in accordance with certain embodiments, the carboxylation product is introduced into the FLLE zone where the organic solvent and aqueous phase have already been in contact in a manner sufficient to form a "dispersed FLLE zone."

In certain embodiments, the combination of temperature within the extraction zone and proportion of aqueous phase introduced into the extraction zone may be important to ensure that 3,6-DCSA solids of the product slurry are dispersed throughout the aqueous phase and then collected in the bottom of the column and recovered in the aqueous phase extract. Generally, the temperature of the carboxylation product mixture introduced into the extraction zone can range from ambient conditions, or room temperature up to approximately 100° C. Overall, therefore, the temperature of the carboxylation product slurry can range from about 25° C. to about 100° C., from about 35° C. to about 100° C., from about 45° C. to about 100° C., or from about 55° C. to about 100° C.

Generally, the organic solvent introduced into the extraction zone is selected from the options listed above. In certain embodiments, the organic solvent comprises xylene, toluene, benzene, or a combination thereof. In certain preferred embodiments, the solvent comprises xylene.

If the organic solvent has a boiling point below 100° C. the extraction zone may be operated under increased pressure conditions in order to suppress boiling without recovery of the 2,5-DCP and/or a salt thereof in the organic phase.

Figure 4:
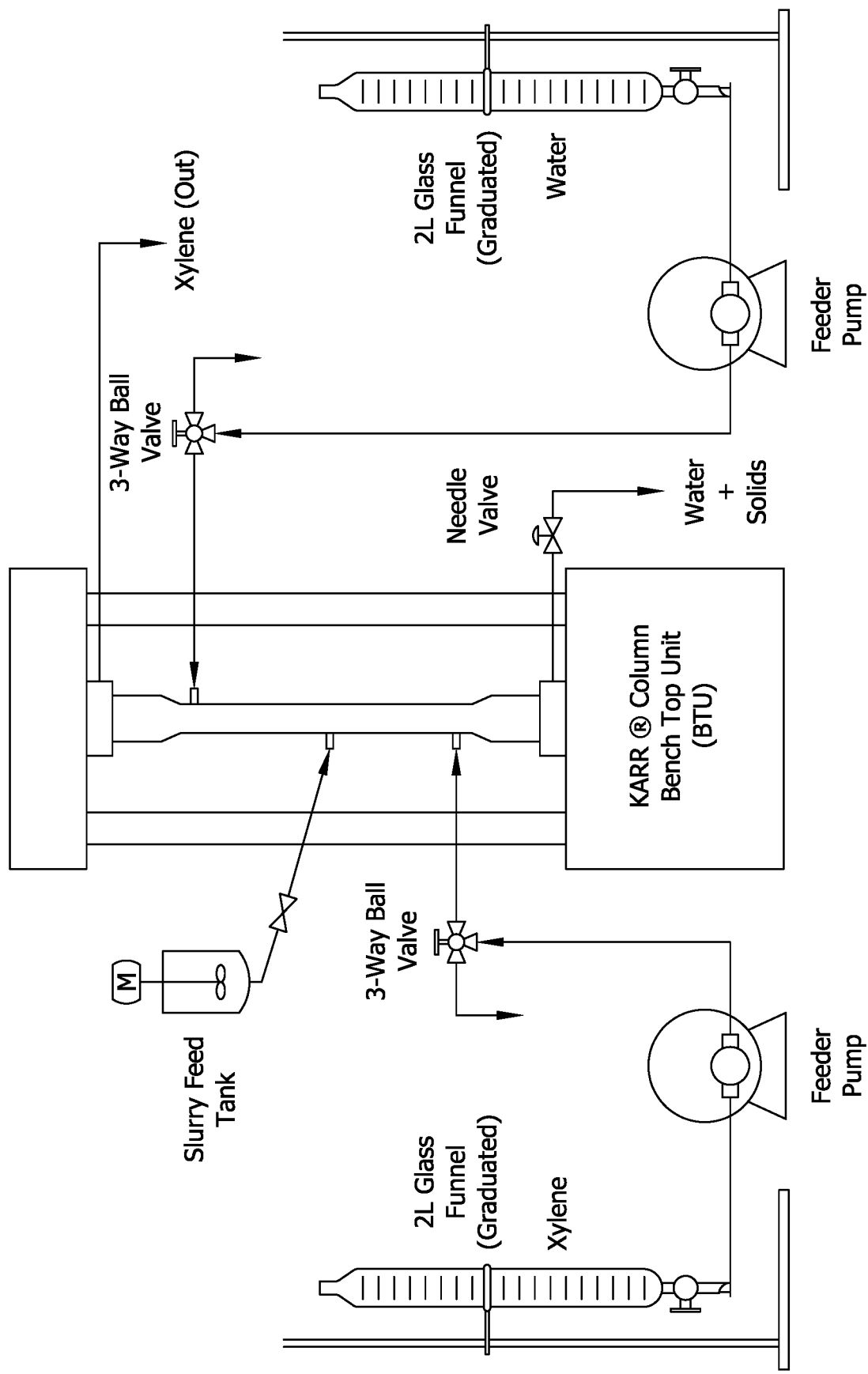
FIG. 4 provides details of a system used in the processes described in Examples 8-10.

FIG. 4 provides details for one apparatus where the organic solvent is introduced at the bottom of the column while the aqueous phase is introduced at the top of the column.

FIG. 5 provides a schematic for a suitable extraction zone generally operated in accordance with the description of FIG. 3 above along with additional apparatus.

As shown in FIG. 5, the system includes heat exchangers 501, 502, and 503 for heating of the process streams prior to introduction into the extraction zone. In certain embodiments, each of the product slurry, organic solvent and aqueous phase are introduced into the extraction zone at an elevated temperature that may be provided and controlled by such means. To achieve a desired temperature within the extraction zone, any or all of the streams introduced into the extraction zone may be heated and/or the contents of the extraction zone itself may be heated.

Also shown in FIG. 5 are organic slurry feed mixture 505 and aqueous slurry feed mixture 507 that are combined to form the feed mixture 509 introduced into the extraction zone. The relative flow rates of these two streams may be controlled to provide a feed mixture introduced into the extraction zone of the desired consistency.

Also shown in FIG. 5 are feed locations 511 and 513 for the aqueous phase and feed locations 515 and 517 for the feed mixture. In accordance with the present invention, a manifold system can be used to control entry of these streams into the extraction zone from the various feed locations to provide desired flow rates and/or promote the interface between the organic phase and aqueous phase in a desired location within the extraction zone.

It has been observed that acidic conditions within the extraction zone facilitate greater partitioning of the 3,6-DCSA to the acidic phase and also partitioning of the 2,5-DCP into the organic phase. Therefore, generally in accordance with the present invention, a separate acidic component is introduced into the extraction zone. This acid addition may occur by incorporation of an acid into aqueous stream 115 shown in FIG. 3 that is introduced into the extraction zone. Generally, suitable acids include organic and inorganic acids (e.g., hydrochloric acid, sulfuric acid, and acetic acid).

In certain other embodiments, a separate acid stream is introduced into the FLLE zone (not shown in FIG. 3). Generally, the acid is introduced into the FLLE zone at a location between the inlet for the aqueous medium and the organic solvent. In this manner the acid may be introduced at a point between the slurry feed location and the inlet for the aqueous medium or at a point between the slurry feed location and the inlet for the organic solvent. In certain embodiments, the acid is introduced at an inlet approximate the feed location for the carboxylation product slurry and on the opposite side of the column. The amount of separate acid to be added to provide the desired pH conditions within the extraction zone may be selected by one skilled in the art based on, for example, the actual and/or relative flow rates of the aqueous medium, organic solvent, and/or carboxylation product slurry.

Figure 6:
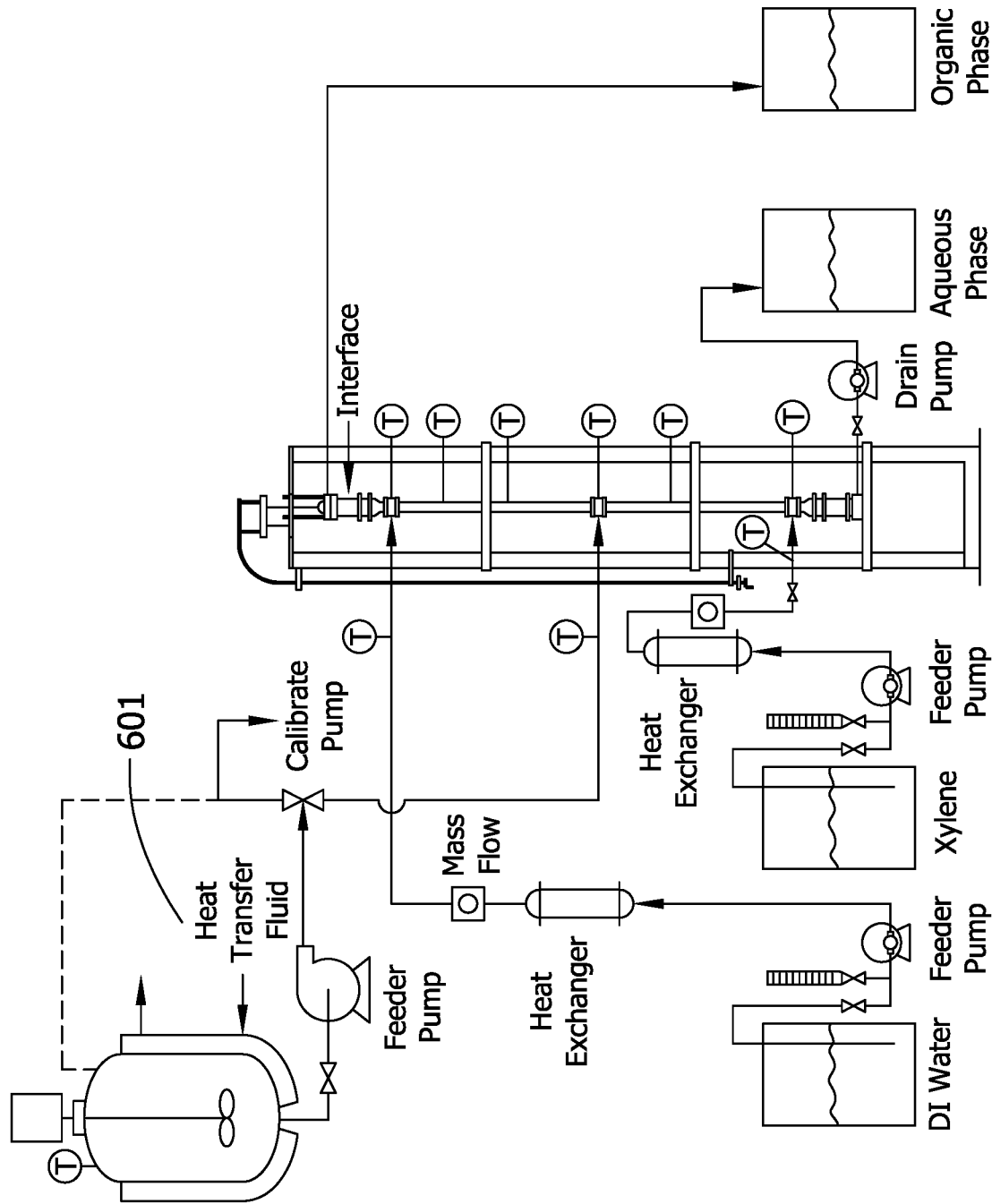
FIG. 6 provides details of a system used in the processes described in Examples 16-18.

FIG. 6 provides a schematic for another apparatus suitable for use in accordance with the present invention. First, the apparatus includes heating means 601 (shown in FIG. 6 as a heat exchanger). In these and certain other embodiments, the target temperature within the extraction zone is in excess of 70° C. (e.g., about 75° C.).

Overall, the goal of the extraction zone is recovery of 3,6-DCSA in the aqueous phase and recovery of 2,5-DCP in the organic phase. Generally in accordance with the processes of the present invention, the aqueous phase contains at least about 2 wt % 3,6-DCSA, at least about 3 wt % DCSA, or at least about 4 wt % 3,6-DCSA. Typically, the aqueous phase contains no more than about 1 wt % 2,5-DCP. Also present in the aqueous extract are 3,6-DCSA solids. Overall, the composition of the aqueous extract indicates partitioning to the aqueous extract of at least about 90 wt %, at least about 95 wt %, or at least about 99 wt % of the 3,6-DCSA initially introduced into the extraction zone. Likewise, the processes of the present invention are characterized by partitioning of less than 10 wt % of the 2,5-DCP introduced into the extraction zone into the aqueous phase.

Generally, pH of the aqueous phase extract is from about 4 to about 9, from about 5 to about 9, or from about 7 to about 9.

Again with reference to FIG. 3, stream 125, which may be referred to as an intermediate 3,6-DCSA product mixture includes the 3,6-DCSA along with salts of 2,5-DCP (e.g., the potassium salt of 2,5-DCP) and salts of DCSA (e.g., the potassium salt of 3,6-DCSA). This stream typically contains at least about 90 wt %, at least about 95 wt %, or at least about 99 wt % of the 3,6-DCSA present in the carboxylation product slurry introduced into the FLLE zone is present in the aqueous phase extract. The salts of 3,6-DCSA in the aqueous phase extract are recovered, neutralized and may be used in a process for preparation of dicamba.

Aqueous phase 125 is recovered from the FLLE zone and fed to mixing vessel 130. The precise configuration of the mixing vessel is not narrowly critical and may be selected from those known in the art.

Into this mixing vessel is introduced an acidic liquid medium 135 (e.g., concentrated hydrochloric acid). Contact of the acid and aqueous phase extract neutralizes the one or more salts of 3,6-DCSA and one or more salts of 2,5-DCP. This results in an aqueous mixture comprising water, 3,6-DCSA solids, and 2,5-DCP dissolved in the aqueous phase. To promote separation of the desired 3,6-DCSA product the contents of the mixing vessel are heated to provide a vapor phase enriched in 2,5-DCP over the aqueous mixture, which is then enriched in 3,6-DCSA as compared to prior to heating.

A vapor phase enriched in 2,5-DCP relative to the aqueous mixture is recovered from the mixing vessel. Overall this vapor phase contains a minor portion of 2,5-DCP with the major portion constituting water. This vapor phase can therefore be condensed to form a recycled aqueous phase 140 that may be introduced into the FLLE zone for use in recovery of 3,6-DCSA. Additionally or alternatively, the recovered aqueous phase can be combined with stream 120 in FIG. 3 and subjected to one or more additional unit operations (e.g., 2,5-DCP purification as shown in FIG. 1.)

From the mixing vessel is recovered a product slurry 145 containing 3,6-DCSA solids and water. The 3,6-DCSA solids are recovered as product 150, which also generates mother liquor 155.

Products 2,5-dichlorophenol and/or a salt thereof present in and/or obtained from a process stream or feed mixture of the present invention can be further converted to 3,6-dichloro-2-methoxybenzoic acid (dicamba) or salt or ester thereof. In particular, certain processes of the present invention further comprise carboxylating 2,5-dichlorophenol or a salt or ester thereof to form 3,6-dichlorosalicylic acid or salt or ester thereof. Subsequently, the 3,6-dichlorosalicylic acid or salt thereof is methylated with a methylating agent to form 3,6-dichloro-2-methoxybenzoic acid or salt thereof and/or methyl 3,6-dichloro-2-methyoxybenzoate. One example of a methylating agent includes dimethyl sulfate. See, for example U.S. Pat. No. 3,013,054, which is incorporated herein by reference. Further, methyl 3,6-dichloro-2-methyoxybenzoate can be saponified with a base to from a salt of 3,6-dichloro-2-methoxybenzoic acid. Acidification of the salt of 3,6-dichloro-2-methoxybenzoic acid (e.g., with HCl) yields 3,6-dichloro-2-methoxybenzoic acid (i.e., dicamba acid).

2,4-DCP present in or recovered from a process stream in accordance with the present invention can be fed to a process for producing 2,4-D. Processes for preparing 2,4-D from 2,4-dichlorophenol include those described in U.S. Pat. Nos. 2,480,817 and 2,651,659.

Having described the invention in detail, it will be apparent that modifications and variations are possible without departing from the scope of the invention defined in the appended claims.

EXAMPLES

The following non-limiting examples are provided to further illustrate the present invention.

Example 1: Reverse-Phase High-Performance Liquid Chromatography ("RP-HPLC") Analytical Method for Determination of Chlorinated Phenols RP-HPLC analysis is used to monitor the compositions of chlorinated phenols or 3,6-dichlorosalicylic acid in both organic phase and aqueous phase of extractions. The analysis was conducted on an Agilent 1260 Infinity Analytical HPLC System equipped with a diode array UV detector and monitored at 220 nm.

Example 2: KARR Columns

Figure 8:
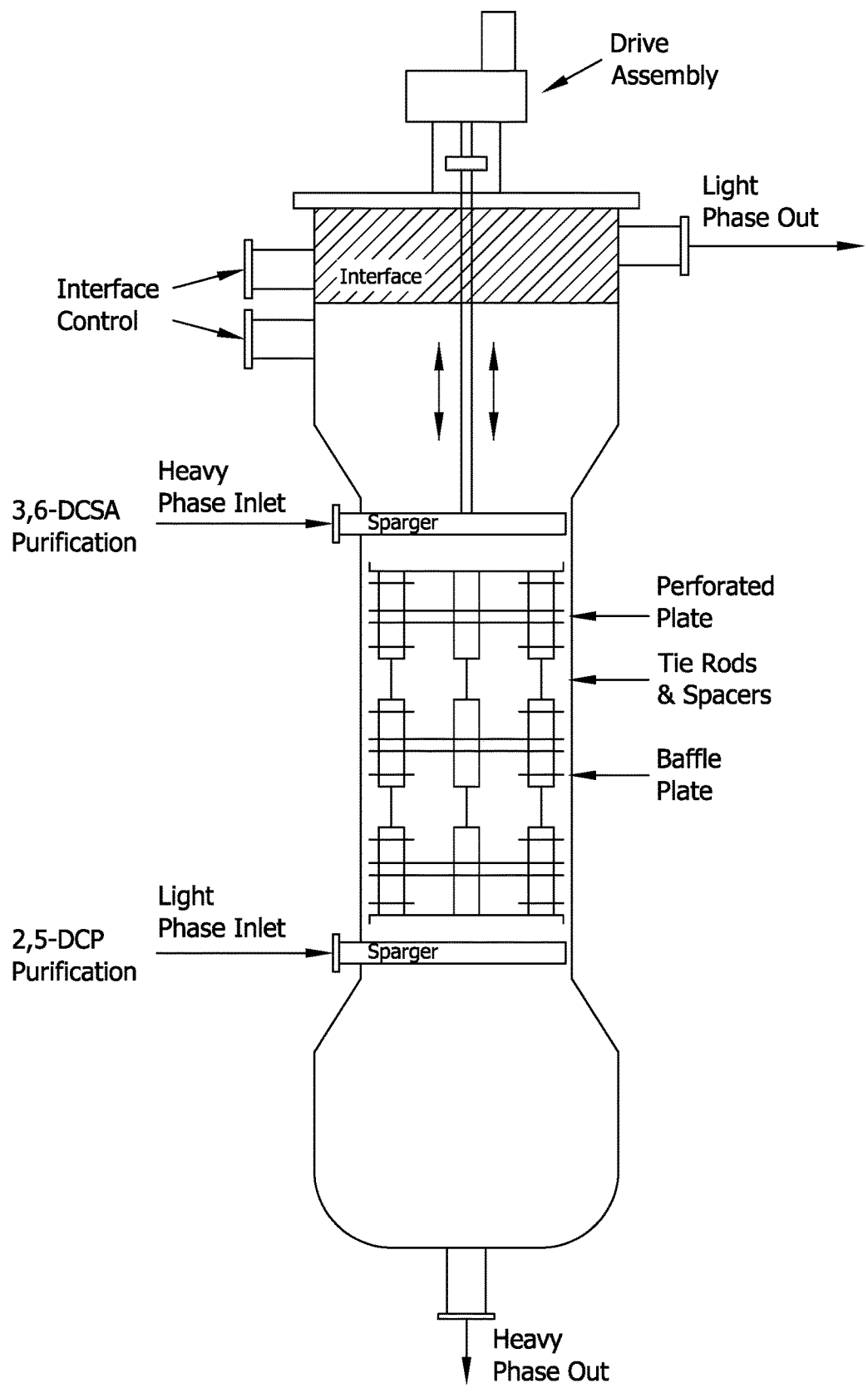
FIG. 8 depicts the KARR column described in Example 2 and used in the processes described in Examples 6, 8, 9, 10, 11, 12, 13, 14, 15, 16, 17, and 18.

The diagram of a typical KARR column is shown in FIG. 8.

The KARR Column BTU (Bench Top Unit) consisted of a ⅝-inch diameter glass column with a 24-inch plate stack height. Two plate assemblies were included (316SS and Teflon perforated plates and spacers) with ½" plate spacing. The heavy phase (e.g., an aqueous solution) inlet was located at the top of the column just above the top plate; and the light phase (e.g., an organic solvent) inlet was located at the bottom of the column just below the bottom plate. The feed mixture inlet was located at the mid-point of the column. FMI pumps were used for metering the organic and aqueous feeds into the column. An air motor was provided to regulate the agitation in the column.

The KARR Column consisted of a 1-inch diameter glass column with a 10-feet plate stack height (316SS and Teflon perforated plates and spacers). Variable plate spacing was used in the column for extraction experiments. A manifold system of the glass column allowed to select locations of the inlets. In general, the heavy phase (e.g., an aqueous solution) inlet was located at the top of the column just above the top plate; and the light phase (e.g., an organic solvent) inlet was located at the bottom of the column just below the bottom plate. The feed mixture inlet location varied either at four (4) feet, five (5) feet, or six (6) feet above the bottom of the column. An air motor was provided to regulate the agitation in the column.

For purification of 2,5-dichlorophenol by extraction, the interface was set at the bottom of the column. For isolation of 3,6-dichlorosalicylic acid, the interface was set at the top of the column.

Example 3: SCHEIBEL Columns

Figure 9:
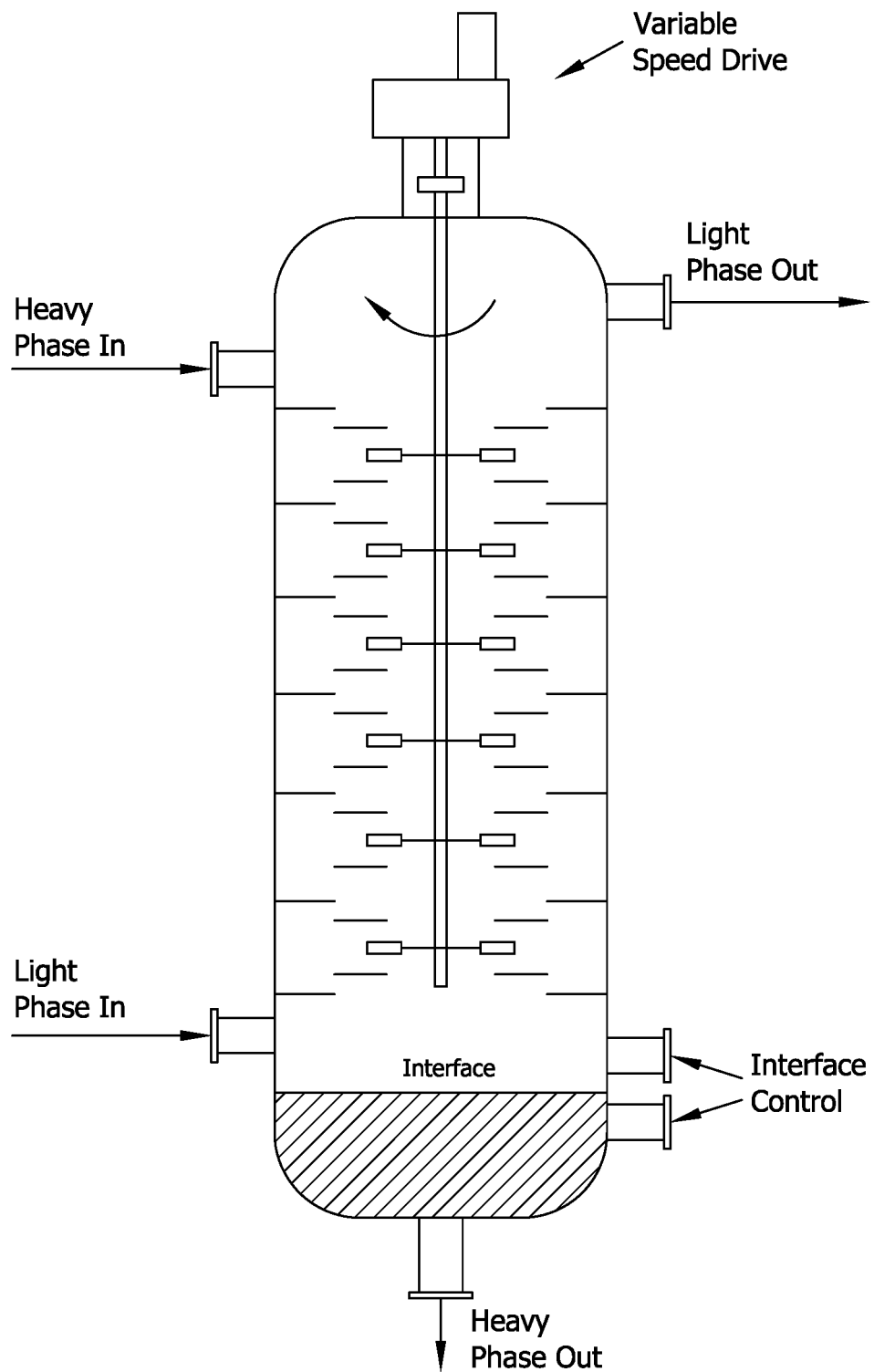
FIG. 9 depicts the SCHEIBEL column described in Example 3 and used in the processes described in Example 7.

The diagram of a typical SCHEIBEL column is shown in FIG. 9. For purification of 2,5-dichlorophenol by extraction, the interface was set at the bottom of the column.

Example 4: Purification of 2,5-Dichlorophenol by KOH Extraction (Stage-1 Purification)

A feed mixture comprising 2,5-dichlorophenol in xylene was prepared as following: a) obtaining a product mixture that was generated from diazotization and hydrolysis of 2,5-dichloroaniline; b) rotary evaporating to increase the 2,5-dichlorophenol concentration in xylene to approximately 20-25 wt %; and c) spiking with two additional impurities of 2,5-dichloro-4-nitrophenol (DCNP) and 1,2,4-trichlorobenzene (124-TCB). The feed mixture composition of is presented in Table 1.

TABLE 1

| Feed Mixture Composition-1 in Xylene | |
|---|---|
| Components | Wt. % |
| 2,5-Dichlorophenol (2,5-DCP) | 20 |
| 2,5-dichloro-4-nitrophenol (2,5-DCNP) | 0.30 |
| 3-chlorophenol (3-CP) | 1.7 |

TABLE 1-continued

Feed Mixture Composition-1 in Xylene

| Components | Wt. % |
|---|---|
| 1,4-dichlorobenzene (1,4-DCB) | 0.2 |
| 1,2,4-trichlorobenzene (1,2,4-TCB) | 0.08 |

A separatory funnel based extraction system was used to illustrate the proof-of-process of purification of 2,5-dichlorophenol from the feed mixture by potassium hydroxide solution extraction. The above-mentioned prepared feed mixture (10 g) was mixed with either 1 N or 3 N aq. KOH solution, and the molar ratio of KOH to 2,5-dichlorophenol varied from 0.006:1 to 1.144:1. The concentrations of each compound in both organic (e.g., xylene) and aqueous layers were measured by the RP-HPLC analytical method. The distribution of each compound in xylene and aqueous layers, affected by the molar ratio of KOH to 2,5-dichlorophenol, is presented in Tables 2a to 2f

TABLE 2a

Distribution of 2,5-DCP in the Xylene/KOH Extraction system

| | KOH Solution Conc. | KOH Addition Volume | KOH Addition | KOH:2,5-DCP | 2,5-DCP wt. % | | 2,5-DCP Distribution[a] | |
|---|---|---|---|---|---|---|---|---|
| Exp. No. | (mol/L) | (mL) | (mmol) | Molar Ratio | Organic | Aqueous | Organic | Aqueous |
| 4.1 | 1 | 0.072 | 0.072 | 0.006 | 24.78 | ND[b] | 100% | 0% |
| 4.2 | 1 | 0.144 | 0.144 | 0.012 | 19.31 | ND[b] | 100% | 0% |
| 4.3 | 1 | 0.216 | 0.216 | 0.018 | 22.04 | ND[b] | 100% | 0% |
| 4.4 | 1 | 0.368 | 0.368 | 0.030 | 19.23 | ND[b] | 100% | 0% |
| 4.5 | 1 | 1.23 | 1.23 | 0.100 | 18.20 | 3.43 | 84% | 16% |
| 4.6 | 1 | 3.69 | 3.69 | 0.301 | 17.66 | 12.68 | 58% | 42% |
| 4.7 | 3 | 4.09 | 12.27 | 1.000 | ND[b] | 19.56 | 0% | 100% |
| 4.8 | 3 | 4.29 | 12.87 | 1.049 | ND[b] | 17.88 | 0% | 100% |
| 4.9 | 3 | 4.5 | 13.5 | 1.100 | ND[b] | 19.82 | 0% | 100% |
| 4.10 | 3 | 4.68 | 14.04 | 1.144 | ND[b] | 16.66 | 0% | 100% |

[a]Distribution was calculated using wt. % in organic layer (or aqueous layer)/total wt. % in both organic and aqueous layers.
[b]Not detected by the RP-HPLC analytical method.

TABLE 2b

Distribution of 2,5-DC-4-NP in the Xylene/KOH Extraction system

| | KOH Solution Conc. | KOH Addition Volume | KOH Addition | KOH:2,5-DCP | 2,5-DCNP wt. % | | 2,5-DCNP Distribution[a] | |
|---|---|---|---|---|---|---|---|---|
| Exp. No. | (mol/L) | (mL) | (mmol) | Molar Ratio | Organic | Aqueous | Organic | Aqueous |
| 4.1 | 1 | 0.072 | 0.072 | 0.006 | 0.11 | 0.10 | 52% | 48% |
| 4.2 | 1 | 0.144 | 0.144 | 0.012 | 0.05 | 0.21 | 19% | 81% |
| 4.3 | 1 | 0.216 | 0.216 | 0.018 | 0.02 | 0.27 | 7% | 93% |
| 4.4 | 1 | 0.368 | 0.368 | 0.030 | 0.00 | 0.28 | 0% | 100% |
| 4.5 | 1 | 1.23 | 1.23 | 0.100 | ND[b] | 0.31 | 0% | 100% |
| 4.6 | 1 | 3.69 | 3.69 | 0.301 | ND[b] | 0.27 | 0% | 100% |
| 4.7 | 3 | 4.09 | 12.27 | 1.000 | ND[b] | 0.23 | 0% | 100% |
| 4.8 | 3 | 4.29 | 12.87 | 1.049 | ND[b] | 0.21 | 0% | 100% |
| 4.9 | 3 | 4.5 | 13.5 | 1.100 | ND[b] | 0.22 | 0% | 100% |
| 4.10 | 3 | 4.68 | 14.04 | 1.144 | ND[b] | 0.21 | 0% | 100% |

[a]Distribution was calculated using wt. % in organic layer (or aqueous layer)/total wt. % in both organic and aqueous layers.
[b]Not detected by the RP-HPLC analytical method.

TABLE 2c

Distribution of 3-CP in the Xylene/KOH Extraction system

| Exp. No. | Solution Conc. (mol/L) | KOH Addition Volume (mL) | KOH (mmol) | KOH:2,5-DCP Molar Ratio | 3-CP wt. % Organic | 3-CP wt. % Aqueous | Distribution[a] Organic | Distribution[a] Aqueous |
|---|---|---|---|---|---|---|---|---|
| 4.1 | 1 | 0.072 | 0.072 | 0.006 | 1.72 | ND[b] | 100% | 0% |
| 4.2 | 1 | 0.144 | 0.144 | 0.012 | 1.32 | ND[b] | 100% | 0% |
| 4.3 | 1 | 0.216 | 0.216 | 0.018 | 1.51 | ND[b] | 100% | 0% |
| 4.4 | 1 | 0.368 | 0.368 | 0.030 | 1.33 | ND[b] | 100% | 0% |
| 4.5 | 1 | 1.23 | 1.23 | 0.100 | 1.33 | ND[b] | 100% | 0% |
| 4.6 | 1 | 3.69 | 3.69 | 0.301 | 1.47 | ND[b] | 100% | 0% |
| 4.7 | 3 | 4.09 | 12.27 | 1.000 | ND[b] | 2.01 | 0% | 100% |
| 4.8 | 3 | 4.29 | 12.87 | 1.049 | ND[b] | 1.84 | 0% | 100% |
| 4.9 | 3 | 4.5 | 13.5 | 1.100 | ND[b] | 2.58 | 0% | 100% |
| 4.10 | 3 | 4.68 | 14.04 | 1.144 | ND[b] | 1.95 | 0% | 100% |

[a]Distribution was calculated using wt. % in organic layer (or aqueous layer)/total wt. % in both organic and aqueous layers.
[b]Not detected by the RP-HPLC analytical method.

TABLE 2d

Distribution of 1,4-DCB in the Xylene/KOH Extraction system

| Exp. No. | Solution Conc. (mol/L) | KOH Addition Volume (mL) | KOH (mmol) | KOH:2,5-DCP Molar Ratio | 1,4-DCB wt. % Organic | 1,4-DCB wt. % Aqueous | Distribution[a] Organic | Distribution[a] Aqueous |
|---|---|---|---|---|---|---|---|---|
| 4.1 | 1 | 0.072 | 0.072 | 0.006 | 0.19 | ND[b] | 100% | 0% |
| 4.2 | 1 | 0.144 | 0.144 | 0.012 | 0.20 | ND[b] | 100% | 0% |
| 4.3 | 1 | 0.216 | 0.216 | 0.018 | 0.19 | ND[b] | 100% | 0% |
| 4.4 | 1 | 0.368 | 0.368 | 0.030 | 0.20 | ND[b] | 100% | 0% |
| 4.5 | 1 | 1.23 | 1.23 | 0.100 | 0.20 | ND[b] | 100% | 0% |
| 4.6 | 1 | 3.69 | 3.69 | 0.301 | 0.20 | ND[b] | 100% | 0% |
| 4.7 | 3 | 4.09 | 12.27 | 1.000 | 0.22 | ND[b] | 100% | 0% |
| 4.8 | 3 | 4.29 | 12.87 | 1.049 | 0.22 | ND[b] | 100% | 0% |
| 4.9 | 3 | 4.5 | 13.5 | 1.100 | 0.23 | ND[b] | 100% | 0% |
| 4.10 | 3 | 4.68 | 14.04 | 1.144 | 0.23 | ND[b] | 100% | 0% |

[a]Distribution was calculated using wt. % in organic layer (or aqueous layer)/total wt. % in both organic and aqueous layers.
[b]Not detected by the RP-HPLC analytical method.

TABLE 2e

Distribution of 1,2,4-TCB in the Xylene/KOH Extraction system

| Exp. No. | Solution Conc. (mol/L) | KOH Addition Volume (mL) | KOH (mmol) | KOH:2,5-DCP Molar Ratio | 1,2,4-TCB wt. % Organic | 1,2,4-TCB wt. % Aqueous | Distribution[a] Organic | Distribution[a] Aqueous |
|---|---|---|---|---|---|---|---|---|
| 4.1 | 1 | 0.072 | 0.072 | 0.006 | 0.07 | ND[b] | 100% | 0% |
| 4.2 | 1 | 0.144 | 0.144 | 0.012 | 0.07 | ND[b] | 100% | 0% |
| 4.3 | 1 | 0.216 | 0.216 | 0.018 | 0.07 | ND[b] | 100% | 0% |
| 4.4 | 1 | 0.368 | 0.368 | 0.030 | 0.07 | ND[b] | 100% | 0% |
| 4.5 | 1 | 1.23 | 1.23 | 0.100 | 0.07 | ND[b] | 100% | 0% |
| 4.6 | 1 | 3.69 | 3.69 | 0.301 | 0.08 | ND[b] | 100% | 0% |
| 4.7 | 3 | 4.09 | 12.27 | 1.000 | 0.08 | ND[b] | 100% | 0% |

TABLE 2e-continued

Distribution of 1,2,4-TCB in the Xylene/KOH Extraction system

| | KOH Solution | KOH Addition | KOH | KOH:2,5-DCP | 1,2,4-TCB wt. % | | 1,2,4-TCB Distribution[a] | |
|---|---|---|---|---|---|---|---|---|
| Exp. No. | Conc. (mol/L) | Volume (mL) | (mmol) | Molar Ratio | Organic | Aqueous | Organic | Aqueous |
| 4.8 | 3 | 4.29 | 12.87 | 1.049 | 0.08 | ND[b] | 100% | 0% |
| 4.9 | 3 | 4.5 | 13.5 | 1.100 | 0.08 | ND[b] | 100% | 0% |
| 4.10 | 3 | 4.68 | 14.04 | 1.144 | 0.08 | ND[b] | 100% | 0% |

[a]Distribution was calculated using wt. % in organic layer (or aqueous layer)/total wt. % in both organic and aqueous layers.
[b]Not detected by the RP-HPLC analytical method.

TABLE 2f

Distribution Comparisons of all species in the Xylene/KOH Extraction system

| Exp. No. | Zone | KOH:2,5-DCP Molar Ratio | 2,5-DCP | 2,5-DCNP | 3-CP | 1,4-DCB | 1,2,4-TCB | 2,5-DCP | 2,5-DCNP | 3-CP | 1,4-DCB | 1,2,4-TCB |
|---|---|---|---|---|---|---|---|---|---|---|---|---|
| | | | Distribution in Organic Layer (%) | | | | | Distribution in Aqueous Layer (%) | | | | |
| 4.1 | 1 | 0.006 | 100 | 52 | 100 | 100 | 100 | 0 | 48 | 0 | 0 | 0 |
| 4.2 | | 0.012 | 100 | 19 | 100 | 100 | 100 | 0 | 81 | 0 | 0 | 0 |
| 4.3 | | 0.018 | 100 | 7 | 100 | 100 | 100 | 0 | 93 | 0 | 0 | 0 |
| 4.4 | | 0.030 | 100 | 0 | 100 | 100 | 100 | 0 | 100 | 0 | 0 | 0 |
| 4.5 | 2 | 0.100 | 84 | 0 | 100 | 100 | 100 | 16 | 100 | 0 | 0 | 0 |
| 4.6 | | 0.301 | 58 | 0 | 100 | 100 | 100 | 42 | 100 | 0 | 0 | 0 |
| 4.7 | 3 | 1.000 | 0 | 0 | 0 | 100 | 100 | 100 | 100 | 100 | 0 | 0 |
| 4.8 | | 1.049 | 0 | 0 | 0 | 100 | 100 | 100 | 100 | 100 | 0 | 0 |
| 4.9 | | 1.100 | 0 | 0 | 0 | 100 | 100 | 100 | 100 | 100 | 0 | 0 |
| 4.10 | | 1.144 | 0 | 0 | 0 | 100 | 100 | 100 | 100 | 100 | 0 | 0 |

In Zone 1, the impurity 2,5-DCNP was extracted out of the organic layer with increasing dose of KOH. When the molar ratio of KOH to 2,5-DCP reached 0.030:1, it was observed that 2,5-DCNP was fully extracted into the aqueous layer while 2,5-DCP remained in the organic layer. In zone 2, 2,5-DCP started partitioning in the aqueous layer. In Zone 3 where abundant KOH is present and the molar ratio of KOH to 2,5-DCP was 1.0:1 or higher, all the phenolic compounds, 2,5-DCP, 2,5-DCNP, and 3-CP, were completely extracted to the aqueous layer; while the non-phenolic compounds (i.e., 1,4-DCB and 1,2,4-TCB) remained in the organic layer. Therefore, the separatory funnel based extraction system demonstrated the extraction selectivity of the above-mentioned compounds related to the amount of KOH in the system.

Example 5: Purification of 2,5-Dichlorophenol by KOH Extraction (Stage-2 Purification)

Meta- and Ortho-CDPP's (chloro-(2,5-dichlorophenoxy) phenol) are dimer compounds which may be formed during the carboxylation reaction of 2,5-dichlorophenol. They may be recycled back to the purification process for the recovery of the unreacted 2,5-DCP. Considering both dimers are phenolic compounds, they might be partitioning together with the key intermediate 2,5-DCP. Using a synthetic feed mixture, the extraction selectivity was tested for removal of these two impurities over 2,5-DCP. The composition of a representative synthetic mixture is presented in Table 3.

TABLE 3

Synthetic Feed Mixture Composition-2 in Xylene

| Components | Wt. % |
|---|---|
| Xylene | 89.0205 |
| 2,5-Dichlorophenol (2,5-DCP) | 10.9137 |
| 3-chlorophenol (3-CP) | 0.0030 |
| 1,4-dichlorobenzene (1,4-DCB) | 0.0324 |
| 1,2,4-trichlorobenzene (1,2,4-TCB) | 0.0070 |
| Meta-(chloro-(2,5-dichlorophenoxy)phenol) (Meta-CDPP) | 0.0073 |
| Ortho-(chloro-(2,5-dichlorophenoxy)phenol) (Ortho-CDPP) | 0.0161 |

The separatory funnel extraction system was initially used to test the selectivity for removal of dimer impurities. Aliquots of the synthetic mixture (10 g) were mixed with various concentrations of aq. KOH solutions at different molar ratio of KOH to 2,5-DCP. The extraction selectivity vs. the molar ratio of KOH to 2,5-DCP was tested for the feasibility of removing two impurity dimer. In addition, the selectivity was also tested with various concentrations of aq. KOH solution. The results for 2,5-DCP, Meta- and Ortho-CDPP partitions are presented in Table 4a.

TABLE 4a

Selectivity for Removal of dimer Impurities by Separatory Funnels

| Experiment No. and Set | | Aq. KOH wt. % | KOH:2,5-DCP Molar ratio | 2,5-DCP | | Meta-CDPP | | Ortho-CDPP | |
|---|---|---|---|---|---|---|---|---|---|
| | | | | wt. % (organic) | Recovery % (aqueous) | wt. % (organic) | Removal % (organic) | wt. % (organic) | Removal % (organic) |
| Control | — | — | — | 10.9000 | — | 0.0068 | — | 0.0156 | — |
| 5.1.1 | 1 | 45.0 | 1.09 | 0.0138 | 99.9 | 0.0000 | 0.0 | 0.0000 | 0.00 |
| 5.1.2 | | 45.0 | 1.01 | 0.0273 | 99.8 | 0.0000 | 0.0 | 0.0002 | 1.3 |
| 5.1.3 | | 45.0 | 0.90 | 0.9361 | 91.4 | 0.0024 | 35.7 | 0.0094 | 60.1 |
| 5.1.4 | | 45.0 | 0.80 | 1.7215 | 84.2 | 0.0038 | 55.7 | 0.0120 | 77.1 |
| 5.1.5 | | 45.0 | 0.64 | 3.2149 | 70.5 | 0.0051 | 74.8 | 0.0140 | 89.9 |
| 5.2.1 | 2 | 22.5 | 1.10 | 0.0083 | 99.9 | 0.0000 | 0.0 | 0.0001 | 0.9 |
| 5.2.2 | | 22.5 | 1.01 | 0.0441 | 99.6 | 0.0002 | 3.0 | 0.0019 | 11.4 |
| 5.2.3 | | 22.5 | 0.91 | 0.9308 | 91.5 | 0.0042 | 62.1 | 0.0135 | 81.0 |
| 5.2.4 | | 22.5 | 0.81 | 1.5451 | 85.8 | 0.0056 | 82.3 | 0.0156 | 93.5 |
| 5.2.5 | | 22.5 | 0.62 | 3.1798 | 70.8 | 0.0067 | 97.5 | 0.0166 | 100.0 |
| 5.3.1 | 3 | 11.25 | 1.10 | 0.0147 | 99.9 | 0.0004 | 4.3 | 0.0017 | 9.0 |
| 5.3.2 | | 11.25 | 1.01 | 0.0577 | 99.5 | 0.0013 | 16.1 | 0.0054 | 29.0 |
| 5.3.3 | | 11.25 | 0.91 | 0.9402 | 91.4 | 0.0067 | 79.8 | 0.0163 | 87.1 |
| 5.3.4 | | 11.25 | 0.81 | 1.8090 | 83.4 | 0.0074 | 88.5 | 0.0171 | 91.3 |
| 5.3.5 | | 11.25 | 0.61 | 4.3195 | 60.4 | 0.0084 | 100.0 | 0.0187 | 100.0 |
| 5.4.1 | 4 | 5.625 | 1.10 | 0.0220 | 99.8 | 0.0019 | 23.8 | 0.0063 | 35.7 |
| 5.4.2 | | 5.625 | 1.00 | 0.1867 | 98.3 | 0.0059 | 73.7 | 0.0152 | 85.9 |
| 5.4.3 | | 5.625 | 0.90 | 1.1046 | 89.9 | 0.0075 | 94.0 | 0.0174 | 98.8 |
| 5.4.4 | | 5.625 | 0.80 | 1.7833 | 83.6 | 0.0076 | 95.4 | 0.0174 | 98.7 |
| 5.4.5 | | 5.625 | 0.60 | 3.7723 | 65.4 | 0.0080 | 100.0 | 0.0177 | 100.0 |
| 5.5.1 | 5 | 2.8125 | 1.10 | 0.0357 | 99.7 | 0.0038 | 46.4 | 0.0100 | 54.3 |
| 5.5.2 | | 2.8125 | 1.00 | 0.2092 | 98.1 | 0.0073 | 88.3 | 0.0170 | 92.2 |
| 5.5.3 | | 2.8125 | 0.90 | 1.2035 | 89.0 | 0.0083 | 100.0 | 0.0184 | 99.6 |
| 5.5.4 | | 2.8125 | 0.80 | 1.7516 | 83.9 | 0.0083 | 99.9 | 0.0185 | 100.0 |
| 5.5.5 | | 2.8125 | 0.60 | 4.2190 | 61.3 | 0.0081 | 97.8 | 0.0181 | 98.1 |

The same correlation was observed between the aqueous recovery percentage of 2,5-DCP that was extracted to the aqueous phase and the molar ratio of KOH to 2,5-DCP. The 2,5-DCP was fully partitioned in the aqueous phase when the molar ratio of KOH to 2,5-DCP was 1.0:1 or higher. The partition of 2,5-DCP was not impacted significantly by the concentration of aq. KOH solution. However, the removal of meta- and ortho-CDPP was highly sensitive to the concentration of aq. KOH solution. Table 4b shows the effect of the concentration of aq. KOH solution on the aqueous recovery of 2,5-DCP and the removal of meta- and ortho-CDPP at the molar ratio of KOH to 2,5-DCP being 0.9:1.

It was observed that a diluted KOH solution favored to achieve higher removals of both meta- and ortho-CDPP while remaining an excellent aqueous recovery of 2,5-DCP (i.e., in about 90%). Higher water usage may increase capital and operating cost, therefore, the concentration of 11.25 wt. % for aq. KOH was chosen for further studies.

A KARR column BTU was used for further studies for selectivity. The feed mixture as a control, listed in Table 4c, was used for extraction. The KOH concentration was 11.25 wt % and the molar ratio of KOH to 2,5-DCP varied from 1:1 to 0.6:1. The results for 2,5-DCP recovery in the aqueous phase and removal of ortho-CDPP are presented in Table 5.

TABLE 4b

Selectivity vs. aq. KOH Concentrations by Separatory Funnels

| Exp. No. | Aq. KOH wt. % | KOH:2,5-DCP Molar ratio | 2,5-DCP | | Meta-CDPP | | Ortho-CDPP | |
|---|---|---|---|---|---|---|---|---|
| | | | wt. % (organic) | Recovery % (aqueous) | wt. % (organic) | Removal % (organic) | wt. % (organic) | Removal % (organic) |
| 5.1.3 | 45.0 | 0.90 | 0.9361 | 91.4 | 0.0024 | 35.7 | 0.0094 | 60.1 |
| 5.2.3 | 22.5 | 0.91 | 0.9308 | 91.5 | 0.0042 | 62.1 | 0.0135 | 81.0 |
| 5.3.3 | 11.25 | 0.91 | 0.9402 | 91.4 | 0.0067 | 79.8 | 0.0163 | 87.1 |
| 5.4.3 | 5.625 | 0.90 | 1.1046 | 89.9 | 0.0075 | 94.0 | 0.0174 | 98.8 |
| 5.5.3 | 2.8125 | 0.90 | 1.2035 | 89.0 | 0.0083 | 100.0 | 0.0184 | 99.6 |

TABLE 5

Selectivity for Removal of dimer Impurities by the KARR Column BTU

| | | | 2,5-DCP | | Ortho-CDPP | |
|---|---|---|---|---|---|---|
| Exp. No. | Aq. KOH wt. % | KOH:2,5-DCP Molar ratio | wt. % (organic) | Recovery % (aqueous) | wt. % (organic) | Removal % (organic) |
| Control | — | — | 10.9115 | — | 0.0363 | — |
| 5.6.1 | 11.25 | 1.00 | 0.0099 | 99.9 | 0.0051 | 14.0 |
| 5.6.2 | 11.25 | 0.95 | 0.0000 | 100.0 | 0.0074 | 20.4 |
| 5.6.3a | 11.25 | 0.90 | 0.0192 | 99.8 | 0.0132 | 36.4 |
| 5.6.3b | 11.25 | 0.90 | 0.1143 | 99.0 | 0.0076 | 20.9 |
| 5.6.4 | 11.25 | 0.80 | 0.3248 | 97.0 | 0.0460 | 100 |
| 5.6.5 | 11.25 | 0.60 | 3.6206 | 66.8 | 0.0382 | 100 |

It was observed that the 2,5-DCP recovery increased by using the KARR BTU extraction column at the same ratio of KOH to 2,5-DCP, compared to the recovery by using separatory funnels. For example, the 2,5-DCP recovery increased from about 91% to about 99% at the molar ratio of KOH to 2,5-DCP being 0.9:1, and the 2,5-DCP recovery increased from about 83% to about 97% at the molar ratio of KOH to 2,5-DCP being 0.8:1, respectively. The ortho-CDPP removal decreased at the molar ratio of KOH to 2,5-DCP being 0.9:1; however, it was substantially removed at the molar ratio of KOH to 2,5-DCP being 0.8:1. The result suggested that the optimal operating condition had the molar ratio of KOH to 2,5-DCP at about 0.8:1 when using the 11.25 wt % KOH solution in the KARR Column BTU.

Example 6: Purification of 2,5-Dichlorophenol by KOH Extraction (KARR Column BTU)

The feed mixture of 2,5-dichloropenol in xylene was prepared as following: a) 1,4-dichlorobenzene was subjected for nitration to obtain 1,4-dichloro-2-nitrobenzene; b) 2,5-dichloroaniline was obtained from reduction of 1,4-dichloro-2-nitrobenzene in the presence of platinum catalyst in acetic acid; c) 2,5-dichlorophenol was produced using the procedures described in WO 2015/095284 with nitrosylsulfuric acid as the diazotization agent in a reaction medium comprising sulfuric acid and acetic acid, followed by hydrolysis and distillation; d) the distillate comprising 2,5-dichlorophenol was extracted to xylene and the resulting extract was washed with water (3 times); and e) the above-prepared 2,5-dichlorophenol/xylene mixture was combined with a recycled material of 2,5-dichlorophenol/xylene mixture (i.e., recycled from the carboxylation reaction) to provide the feed mixture.

The contents of 2,5-dichlorophenol (2,5-DCP), 2,5-dichloro-4-nitrophenol (2,5-DCNP), and acetic acid (AcOH) in the above-prepared feed mixture was analyzed for calculating the KOH charge used in the KARR Column BTU. The purification of 2,5-dichlorophenol was conducted as following: a) feeding the feed mixture to the KARR Column BTU counter-currently with an aqueous KOH solution (0.4 wt. %) at a flow rate and the molar ratio of KOH to the total amount of 2,5-DCNP and AcOH was 2:1; b) collecting the organic phase comprising 2,5-dichlorophenol; c) feeding the collected organic phase to the KARR BTU extraction column counter-currently with an aqueous KOH solution (11.25 wt. %) at a flow rate and the molar ratio of KOH to 2,5-DCP was 0.8:1. The results are presented in Table 6.

TABLE 6

KOH-mediated Two-stage Purification by the KARR Column BTU

| | Feed mixture in Xylene composition | Stage-1 Purification (Removal of 2,5-DCNP) Organic Phase | | | Stage-2 Purification (Removal of CDPP) | | |
|---|---|---|---|---|---|---|---|
| | | | | | Organic | Aqueous Phase | |
| | Wt. %. | Wt. % | Recovery % | Removal % | Wt. % | Recovery % | Removal % |
| 2,5-DCP | 8.7102 | 8.3159 | 95.5 | — | 1.4300 | 82.8 | — |
| 2,5-DCNP | 0.0136 | 0.0011 | 8.3 | 91.7 | ND | 34.4 | 63.6 |
| 3-CP | 0.0030 | 0.0028 | 96.4 | — | 0.0017 | 41.2 | 58.8 |
| 1,4-DCB | 0.0713 | 0.0679 | 95.1 | — | 0.0708 | — | 100 |
| Meta-CDPP | 0.0244 | 0.0231 | 94.6 | — | 0.0208 | — | 90.4 |

After the first extraction (i.e., the stage-1 purification), more than 90% of 2,5-DCNP was successfully removed from the organic extract comprising 2,5-DCP. After the second extraction (i.e., the stage-2 purification), the 2,5-DCP and/or a salt thereof was recovered in the aqueous phase in about 83%. The 3-monochlorophenol (3-CP) and/or a salt thereof was partially removed in about 59% from the aqueous phase comprising 2,5-DCP and/or a salt thereof. Other species, for example, 1,4-dichlorobenzene (1,4-DCB) and meta-CDPP were substantially removed from the aqueous phase comprising 2,5-DCP and/or a salt thereof. The KOH-mediated purification process by the KARR Column BTU demonstrated a high selection to obtain enriched 2,5-DCP by removing unwanted chlorophenol species during the two-stage extraction process.

Example 7: Purification of 2,5-Dichlorophenol by KOH Extraction (SCHEIBEL Column)

A: The Feed Mixture of 2,5-Chloropenol in Xylene Containing $CO_2$ (Stage-1 and Stage-2 Purification)

The feed mixture of 2,5-chloropenol in xylene was prepared as described in Example 4. A portion of the feed mixture (in about 70%) was sparged with $CO_2$ gas overnight before and during the testing. The $CO_2$-sparged feed mixture was mixed with the non-sparged portion of the feed mixture in an approximately 7:3 ratio in the feed line. The composition of the feed mixture is presented in Table 7.

TABLE 7

Feed Mixture Composition-3 in Xylene

| Component | Wt. % |
|---|---|
| 2,5-Dichlorophenol (2,5-DCP) | 11.6516 |
| 3-chlorophenol (3-CP) | 0.0367 |
| 2,5-dichloro-4-nitrophenol (2,5-DCNP) | 0.1485 |
| 1,4-dichlorobenzene (1,4-DCB) | 0.0573 |
| 1,2,4-trichlorobenzene (1,2,4-TCB) | 0.0122 |
| Meta-(chloro-(2,5dichlorophenoxy)phenol) (Meta-CDPP) | 0.0692 |
| Ortho-(chloro-(2,5dichlorophenoxy)phenol) (Ortho-CDPP) | 0.0163 |
| Water | 0.1032 |
| Acetic acid | 0.0061 |
| Xylene | 87.8989 |
| $CO_2$[a] | 0.0147 |

[a]$CO_2$ concentration is estimated based on the total inorganic carbon level in one of aqueous extraction samples, method expecting large errors.

The stage-1 purification of 2,5-dichlorophenol to remove the 2,5-DCNP was conducted as following: a) heating the mixed feed mixture to 40° C. before being sent to the column for extraction; a) feeding the feed mixture to the SCHEIBEL extraction column counter-currently with an aqueous KOH solution (1 wt. %). Parameters, for example, feed rate of the KOH solution, KOH solution concentration, and number of stages were tested to achieve the best conditions for 2,5-DCP recovery and 2,5-DCNP removal in the organic phase. Table 8 lists the parameters for each experiment and corresponding results of 2,5-DCP recovery and 2,5-DCNP removal in the organic phase.

All experiments achieved excellent material balance comparing the initial total feed rate of the feed mixture and recovered materials in both organic and aqueous phases (not shown in Table 8). Experiment 7.1.6 showed that the operating conditions, listed in Table 8, allowed to remove the majority of 2,5-DCNP (e.g., in 88.3%) while maintaining the 2,5-DCP loss to be less than about 0.5%. In addition, the 2,5-DCNP removal in the organic phase exhibited a linear response related to molar ratio of KOH to the total of AcOH, 2,5-DCNP, and $CO_2$, where increased molar ratio provided better removal of 2,5-DCNP.

The organic phase extract from one of the stage-1 purification experiments was used as the feed mixture for the stage-2 purification to remove the meta- and ortho-CDPP. The composition of this feed mixture is presented in Table 9.

TABLE 9

Feed Mixture Composition-4 in Xylene

| Component | Wt. % |
|---|---|
| 2,5-Dichlorophenol (2,5-DCP) | 11.0000 |
| 3-chlorophenol (3-CP) | 0.0343 |
| 2,5-dichloro-4-nitrophenol (2,5-DCNP) | 0.0382 |
| 1,4-dichlorobenzene (1,4-DCB) | 0.0527 |
| 1,2,4-trichlorobenzene (1,2,4-TCB) | 0.0114 |
| Meta-(chloro-(2,5dichlorophenoxy)phenol) (Meta-CDPP) | 0.0167 |
| Ortho-(chloro-(2,5dichlorophenoxy)phenol) (Ortho-CDPP) | 0.0150 |
| Xylene | 88.8317 |

The KOH concentration for the extraction was 11.25 wt % and the molar ratio of KOH to 2,5-DCP varied from about 1:1 to about 0.6:1. The results for 2,5-DCP recovery (i.e., as 2,5-DCP and/or the K salt thereof) in the aqueous phase and removal of both meta- and ortho-CDPPs are presented in Table 10.

TABLE 8

Stage-1 Purification by the SCHEIBEL Column

Feed Rate of the Feed Mixture:
total at 408.48 g/min; AcOH at 0.00040 mol/min; 2,5-DCNP at 0.00292 mol/min;
$CO_2$ at 0.00095 mol/min; 2,5-DCP at 0.29199 mol/min
Extraction Column: Temperature at 40° C.; Agitation at 500 RPM

| Exp. No. | Column Stages | 1 wt. % KOH feed rate g/min | 1 wt. % KOH feed rate Mol/min | KOH: (AcOH + DCNP + $CO_2$) Molar Ratio | Organic Phase 2,5-DCP Recovery % | Organic Phase 2,5-DCNP Removal % | Aq. Phase pH |
|---|---|---|---|---|---|---|---|
| 7.1.1 | 30 | 24 | 0.0043 | 1.0 | 99.9 | 40.3 | 7.3 |
| 7.1.2 | 30 | 41.5 | 0.0074 | 1.7 | 99.9 | 65.6 | 7.3 |
| 7.1.3 | 30 | 41.5 | 0.0074 | 1.7 | 99.9 | 72.7 | 7.4 |
| 7.1.4 | 30 | 50 | 0.0089 | 2.1 | 99.9 | 81.3 | 7.4 |
| 7.1.5 | 20 | 50 | 0.0089 | 2.1 | 99.9 | 76.1 | 7.3 |
| 7.1.6 | 30 | 60 | 0.0107 | 2.5 | 99.8 | 88.3 | 7.4 |

TABLE 10

Stage-2 Purification by the SCHEIBEL Column

Feed Rate of the feed Mixture:
total at 410 g/min; 2,5-DCP at 0.277 mol/min;
Meta-DCPP at 0.000236 mol/min; and Ortho-DCPP at 0.000212 mol/min
Extraction Column: 40 stages of column;
Temperature at 40° C. and then 50° C.; Agitation at 450 RPM

| | 11.25 wt. % KOH feed rate | | | Aqueous Phase | | | |
|---|---|---|---|---|---|---|---|
| Exp. No. | g/min | Mol/min | KOH:2,5-DCP Molar Ratio | 2,5-DCP Recovery % | Meta-CDPP Removal % | Ortho-CDPP Removal % | pH |
| 7.2.1 | 154 | 0.309 | 1.12 | 99.9 | 22.7 | 44.5 | 10.3 |
| 7.2.2 | 140 | 0.281 | 1.01 | 98.9 | 73.3 | 85.8 | 10.4 |
| 7.2.3 | 84 | 0.168 | 0.61 | 57.9 | 89.7 | 100 | 10.4 |

The above experiments achieved excellent material balance of 2,5-DCP (i.e., as 2,5-DCP and/or the K salt thereof) comparing the initial total feed rate of the feed mixture and recovered materials in both organic and aqueous phases (not shown in Table 10). Experiment 5.2.2 showed that the operating conditions, listed in Table 10, allowed to remove the majority of dimeric impurities (e.g., in 73.3% removal for meta-CDPP and in 85.8% removal for ortho-CDPP) while maintaining the 2,5-DCP loss to be less than about 2%. Based on these experimental results, the optimal molar ratio of KOH to 2,5-DCP for the stage-2 purification was at about 1.01.

B: The Feed Mixture of 2,5-Dichlorophenol in Xylene without $CO_2$ (Stage-2 Purification)

The feed mixture of 2,5-dichlorophenol in xylene was freshly prepared. The composition of the feed mixture is presented in Table 11.

TABLE 11

Feed Mixture Composition-5 in Xylene

| Component | Wt. % |
|---|---|
| 2,5-Dichlorophenol (2,5-DCP) | 11.4152 |
| 3-chlorophenol (3-CP) | 0.0345 |
| 2,5-dichloro-4-nitrophenol (2,5-DCNP) | 0.0047 |
| 1,4-dichlorobenzene (1,4-DCB) | 0.0515 |
| 1,2,4-trichlorobenzene (1,2,4-TCB) | 0.0106 |
| Meta-(chloro-(2,5dichlorophenoxy)phenol) (Meta-CDPP) | 0.0159 |
| Ortho-(chloro-(2,5dichlorophenoxy)phenol) (Ortho-CDPP) | 0.0146 |
| Xylene | 88.4530 |

The KOH concentration for the extraction was 11.25 wt % and the molar ratio of KOH to 2,5-DCP varied from about 1:1 to about 0.7:1. The results for 2,5-DCP recovery (i.e., as 2,5-DCP and/or the K salt thereof) in the aqueous phase and removal of both meta- and ortho-CDPPs are presented in Table 12.

TABLE 12

Stage-2 Purification by the SCHEIBEL Column (without $CO_2$)

Feed Rate of the feed Mixture:
total at 410 g/min; 2,5-DCP at 0.287 mol/min;
Meta-DCPP at 0.000225 mol/min; and Ortho-DCPP at 0.000207 mol/min
Extraction Column: 40 stages of column;
Temperature at 40° C. and then 50° C.; Agitation at 450 RPM

| | 11.25 wt. % KOH feed rate | | | Aqueous Phase | | | |
|---|---|---|---|---|---|---|---|
| Exp. No. | g/min | Mol/min | KOH:2,5-DCP Molar Ratio | 2,5-DCP Recovery % | Meta-CDPP Removal % | Ortho-CDPP Removal % | pH |
| 7.3.1 | 140 | 0.281 | 0.98 | 99.9 | 4.6 | 6.6 | 11.7 |
| 7.3.2 | 133 | 0.267 | 0.93 | 99.9 | 4.7 | 7.5 | 10.8 |
| 7.3.3 | 126 | 0.253 | 0.88 | 99.9 | 10.2 | 13.0 | 10.6 |
| 7.3.4 | 119 | 0.239 | 0.83 | 99.9 | 40.7 | 82.7 | 10.6 |
| 7.3.5 | 112 | 0.225 | 0.78 | 84.8 | 98.4 | 97.1 | 10.6 |
| 7.3.6 | 105 | 0.211 | 0.73 | 77.8 | 95.7 | 98.9 | 10.6 |

Similarly, the above experiments also achieved excellent material balance of 2,5-DCP (i.e., as 2,5-DCP and/or the K salt thereof) comparing the initial total feed rate of the feed mixture and recovered materials in both organic and aqueous phases (not shown in Table 12). Experiment 7.3.4 achieved the best removal of dimeric impurities (e.g., in 40.7% removal for meta-CDPP and in 82.7% removal for ortho-CDPP) while maintaining the 2,5-DCP loss to be less than about 0.5%. Based on these experimental results, the optimal molar ratio of KOH to 2,5-DCP for the stage-2 purification was at about 0.83, which was in about 0.2 lower than previous experiment (i.e., Experiment 7.2.2). The remaining $CO_2$ in the organic raffinate from the stage-1 purification may contribute to the higher optimal molar ratio of KOH to 2,5-DCP, where additional KOH was required to neutralize the remaining $CO_2$.

In addition, the agitation at 500 RPM was also evaluated and found to lead incipient flooding under these conditions.

Example 8: General Procedure for Isolation of 3,6-Dichlorosalicylic Acid by Extraction (KARR Column BTU)

The glass shell of the KARR column BTU was modified to add a nozzle at the mid-point of the column for the addition of a slurry feed mixture in xylene (e.g., solids suspended in xylene).

For the pilot study, the slurry feed mixture was fed to the middle of the column; fresh xylene was fed to the bottom of the column; and de-ionized (DI) water was fed to the top of the column. In general, the slurry feed mixture comprised 3,6-dichlorosalicylic acid, 2,5-dichlorophenol, and/or the K salt thereof. After extraction, the 2,5-dichlorophenol was recovered in the xylene leaving the top of the column; and the 3,6-dichlorosalicylic acid and/or the K salt thereof (e.g., solids) stayed as a slurry in water in the bottom of the column.

The equipment set-up is shown in FIG. 4. There were several aspects for the equipment setup. The DI water inlet was located at the top of the column just above the top plate; and the xylene inlet was located at the bottom of the column just below the bottom plate. FMI pumps were used for metering the xylene and DI water feeds into the column. Flow rates were determined by periodic time volumetric measurements. The DI water and xylene were fed from dropping funnels via the FMI pumps and top/bottom inlets counter-currently into column. The slurry feed mixture was placed in a separatory funnel and fed into the middle of the column via a funnel through a tube (¾" ID) that connected the mid-point nozzle of the column and the funnel. The separatory funnel was agitated prior to each addition. The additions were made by opening the valve at the bottom of the funnel and allowing a small amount of slurry to enter the column. For all experimental runs, the heavy aqueous phase was discharged into an aqueous receiver through a ball valve at the bottom of the column. The light organic phase was allowed to overflow from the column into an organic receiver.

The extraction experiment was conducted by following procedures: a) the column was initially filled with DI water to set the interface at the top of the column; b) when the column was full, both FMI pumps were turned on and set to the desired flow rates. The column agitation speed was initially set at 100 stroke per minute (SPM) to observe the phase behavior; c) the interface was established in the upper disengaging chamber, and then controlled by the discharging rate at the bottom of the column (i.e. requiring to set the discharge valve); d) the column agitation speed was increased until the dispersion of xylene into the water phase was acceptable; e) the slurry feed mixture was intermittently fed to the column as described above; f) after approximately 30 minutes at a given condition, the light organic and heavy aqueous phases were sampled for analysis.

Different experiment runs were conducted by varying the xylene and/or water inlet rates. All experiments were performed at ambient temperature.

Example 9: Isolation of 3,6-Dichlorosalicylic Acid by Extraction (Test-1 on KARR Column BTU)

Example 8 was repeated with a slurry feed mixture for feasibility of extraction/isolation of 3,6-dichlorosalicylic acid and/or the K salt thereof (e.g. as solids). A slurry feed mixture was prepared the day before by following: a) mixing xylene (1775 g), 2,5-dichlorophenol (106 g), and solids (379 g) comprising 3,6-dichlorosalicylic acid and/or the K salt thereof; b) agitating the mixture well; c) allowing to sit overnight. The slurry feed mixture was agitated again before sampling and being transferring to the seperatory funnel for addition to the column. The initial water flow was set at 40 mL/min and the initial xylene flow was set at 20 mL/min. The column agitation speed was increased from 100 SPM to 225 SPM to get a good dispersion of xylene. Once the slurry feed mixture was added to the column, the agitation was reduced to the desired speed. Both water and xylene flow rates were varied for each experimental run. The operation conditions for four experimental runs are presented in Table 13-A.

TABLE 13-A

| | System Operation Conditions | | | | |
|---|---|---|---|---|---|
| Exp. No. | Xylene Flow Rate (mL/min) | Water Flow Rate (mL/min) | Xylene:Water | Column Agitation Speed (SPM) | Temperature (° C.) |
| 9.1 | 20 | 40 | 1:2 | 180 | 27 |
| 9.2 | 10 | 40 | 1:4 | 180 | 27 |
| 9.3 | 5 | 40 | 1:8 | 180 | 27-28 |
| 9.4 | 30 | 30 | 1:1 | 160 | 29 |

In Experiment 9.1, the slurry feed mixture entered the column and displayed in two phases. The heavy aqueous phase was observed to have small solid flakes and the light organic phase appeared to be emulsion. In the agitation zone, the small solid flakes were mostly broken up into fine solids or partially dissolving in the aqueous phase, while the emulsion-like droplets were also broken up in the organic phase. The solids, enriched with 3,6-dichlorosalicylic acid and/or the K salt thereof, were observed to reach the bottom of column infrequently. However, the top of the column had significant coalescence of the dispersed phase on the column internals. It was believed that the inappropriate dispersion of xylene into the water phase was caused by the xylene flow rate being too high.

In Experiment 9.2, the xylene flow rate was reduced to 10 mL/min. The improved dispersion of xylene into the water phase addressed the coalescence of the dispersed phase at the top of the column. The solids, enriched with 3,6-dichlorosalicylic acid and/or the K salt thereof, were observed to reach the bottom of column more frequently.

In Experiment 9.3, the xylene flow rate was further reduced to 5 mL/min. While the dispersion of xylene into water phase continued to be acceptable, more solids were observed to accumulate in the bottom of column. Near the end of run, the slurry feed tube was observed to have some plugging issues, occurred at the interface of the slurry and the continuous water phase.

In Experiment 9.4, the flow rates of xylene and water were both set at 30 mL/min. The agitation speed was reduced to 160 SPM to address the emulsion issues occurred in the bottom disengaging chamber. With the xylene entering the column with the slurry at the much higher flow rate, the interface of xylene and water was found to be difficult to control.

At the end of each run, two samples were taken from both organic and aqueous phases for analysis. Table 13-B shows the extraction efficacy of 2,5-dichlorophenol, 3,6-dichlorosalicylic acid, and/or the K salt thereof for each run.

TABLE 13-B

Extraction efficacy of the First Test

| Exp. No. | Phase | 3,6-DCSA (wt. %) | 2,5-DCP (wt. %) | 3,6-DCSA:2,5-DCP | pH |
|---|---|---|---|---|---|
| Feed Mixture | slurry | 4.78 | 3.82 | 56:44 | — |
| 9.1 | Aqueous | 0.35 | 0.13 | 73:27 | 8.83 |
| 9.2 | | 0.63 | 0.39 | 62:38 | 9.16 |
| 9.3 | | 0.13 | 0.07 | 65:35 | 8.21 |
| 9.4 | | 1.88 | 0.07 | 96:4 | 9.21 |
| 9.1 | Organic | 0.02 | 1.53 | 1:99 | — |
| 9.2 | | 0.03 | 2.81 | 1:99 | — |
| 9.3 | | 0.02 | 1.31 | 1:99 | — |
| 9.4 | | 0.02 | 1.89 | 1:99 | — |

The first test on the KARR Column BTU system demonstrated the hydraulic feasibility for performing the extraction process to isolate 3,6-dichlorosalicylic acid and/or the K salt thereof, and to recover 2,5-dichlorophenol and/or the K salt thereof. There were no issues to have a continuous operation when solids are present in the bottom of the column.

The organic phase at the top of column from each run was substantially free of 3,6-dichlorosalicylic acid and/or the K salt thereof (e.g., <320 ppm). The ratio of 3,5-DCSA to 2,5-DCP in the aqueous phase increased as the ratio of xylene to water increased with exception of Experiment 9.2.

Example 10: Isolation of 3,6-Dichlorosalicylic Acid by Extraction (Test-2 on KARR Column BTU)

Example 8 was repeated with a slurry feed mixture for confirmation of extraction/isolation of 3,6-dichlorosalicylic acid and/or the K salt thereof (e.g., as solids). The second test was to confirm and/or make any necessary adjustments when the slurry feed mixture was prepared using the solids that were further processed by a xylene azeotropic process (i.e., to remove water). A slurry feed mixture was prepared the day before by following: a) mixing xylene (2300 g), 2,5-dichlorophenol (100 g), and solids (610 g) comprising 3,6-dichlorosalicylic acid, 2,5-dichlorophenol, and/or the K salt thereof; b) agitating the mixture well; c) allowing to sit overnight; d) adding additional xylene (2300 g) due to the thickness of the mixture. The slurry feed mixture was agitated again before sampling and being added to the column. The additions were made by scooping the slurry onto a metal spatula and placing it into the feed tube.

The initial water flow was set at 40 mL/min and the initial xylene flow was set at 20 mL/min. The column agitation speed was increased from 100 SPM to 160 SPM to get a good dispersion of xylene. The water flow was increased to 55 mL/min and the xylene flow was reduced to 5 mL/min. Once the dispersion was stable, the slurry feed mixture was started to enter the column. Water and xylene flow rates and the agitation speed were varied for each experimental run. The operation conditions for six experimental runs are presented in Table 14-A.

TABLE 14-A

System Operation Conditions

| Exp. No. | Xylene Flow Rate (mL/min) | Water Flow Rate (mL/min) | Xylene:Water | Column Agitation Speed (SPM) | Temperature (° C.) |
|---|---|---|---|---|---|
| 10.1 | 5 | 55 | 1:11 | 160 | 30 |
| 10.2 | 5 | 55 | 1:11 | 180 | 31 |
| 10.3 | 10 | 50 | 1:5 | 180 | 31 |
| 10.4 | 20 | 40 | 1:2 | 180, 160, and 140 | 32 |
| 10.5 | 30 | 30 | 1:1 | 140 | 32-33 |
| 10.6 | 40 | 20 | 2:1 | 140 | 30-31 |

In Experiment 10.1, the water flow was set at 55 mL/min; the xylene flow was set at 5 mL/min; and the column agitation speed was set at 160 SPM. The slurry feed mixture entered the column as emulsion droplets. Solids were carried up in the column by the dispersed xylene phase. As the column plates broke up the droplets, the solids dissolved into either organic or aqueous phase.

In Experiment 10.2, the column agitation speed was increased to 180 SPM while the flow rates of water and xylene were kept constant at 55 mL/min and 5 mL/min; respectively. The increased agitation speed improved the dispersion of the slurry feed in the top half of the column.

In Experiment 10.3, the water flow rate was decreased to 50 mL/min; the xylene flow rate was increased to 10 mL/min; and the column agitation speed was kept constant at 180 SPM. The organic phase appeared to be cloudier compared to previous two runs.

In Experiment 10.4, the water flow rate was decreased to 40 mL/min; the xylene flow rate was increased to 20 mL/min; and the column agitation speed was kept constant at 180 SPM initially. The column began to flood at the bottom so the agitation was subsequently reduced to 160 SPM and further to 140 SPM.

In Experiment 10.5, the flow rates of water and xylene were both set at 30 mL/min while the column agitation speed was kept constant at 140 SPM.

In Experiment 10.6, the water flow rate was decreased to 20 mL/min; the xylene flow rate was increased to 40 mL/min; and the column agitation speed was kept constant at 140 SPM. Most of the slurry feed mixture moved up in the column, and solids dissolved in both organic and aqueous phases.

At the end of each run, two samples were taken from both organic and aqueous phases for analysis. Table 14-B shows the extraction efficacy of 2,5-dichlorophenol, 3,6-dichlorosalicylic acid, and/or the K salt thereof for each run.

TABLE 14-B

Extraction efficacy of the Second Test

| Exp. No. | Phase | 3,6-DCSA (wt. %) | 2,5-DCP (wt. %) | 3,6-DCSA:2,5-DCP | pH |
|---|---|---|---|---|---|
| Feed Mixture | slurry | | | | — |
| 10.1 | Aqueous | 0.62 | 0.41 | 60:40 | 9.13 |
| 10.2 | | 0.62 | 0.39 | 61:39 | 9.13 |
| 10.3 | | 0.46 | 0.20 | 70:30 | 9.21 |
| 10.4 | | 0.55 | 0.30 | 65:35 | 9.54 |
| 10.5 | | 0.63 | 0.33 | 66:34 | 9.72 |
| 10.6 | | 0.98 | 0.48 | 67:33 | 10.12 |
| 10.1 | Organic | 0.005 | 1.89 | 0.3:99.7 | — |
| 10.2 | | 0.004 | 1.98 | 0.2:99.8 | — |
| 10.3 | | 0.004 | 1.67 | 0.2:99.8 | — |
| 10.4 | | 0.004 | 0.63 | 0.6:99.4 | — |
| 10.5 | | 0.003 | 0.80 | 0.4:99.6 | — |
| 10.6 | | 0.003 | 0.55 | 0.5:99.5 | — |

The second test on the KARR Column BTU system assured the hydraulic feasibility for performing the extraction process to isolate 3,6-dichlorosalicylic acid and/or the K salt thereof, and to recover 2,5-dichlorophenol and/or the K salt thereof. There were no solids built up in the bottom of the column that prevented continuous operation.

The organic phase at the top of column from each run was substantially free of 3,6-dichlorosalicylic acid and/or the K salt thereof (e.g., <50 ppm). When the column agitation was kept constant, the ratio of 3,5-DCSA to 2,5-DCP in the aqueous phase increased as the ratio of xylene to water increased, as represented from Exp. 10.2 to Exp. 10.3 (agitation at 180 SPM) and from Exp. 10.4 to 10.6 (agitation at 140 SPM). When the column agitation was kept constant (e.g., at 180 SPM), the ratio of 3,5-DCSA to 2,5-DCP in the aqueous phase increased as the ratio of xylene to water increased from 1:11 to 1:5, as represented in Experiments 10.2 and 10.3. Similar trend was observed in Experiments 10.4 to 10.6 (i.e., the ratio of xylene to water was from 1:2, 1:1 to 2:1) when the agitation was at 140 SPM. When the ratio of xylene to water was kept constant (e.g., at 1:11), the ratio of 3,5-DCSA to 2,5-DCP in the aqueous phase increased as the column agitation increased from 160 to 180, as represented in Experiments 10.1 and 10.2.

Example 11: General Procedure-1 for Isolation of 3,6-Dichlorosalicylic Acid by Extraction (KARR Column)

For the pilot plant test, the KARR Column, described in Example 2, was used. Variable plate spacing was used in the column. Starting from the bottom of the column, the plate stacking order was: 2.5-foot height of standard 2-inch spacing, 1-foot height of 3-inch spacing, 1-foot height of 4-inch spacing, 1-foot height of 3-inch spacing, and 4.5-foot height of standard 2-inch spacing. A manifold system of the glass column had five inlets available to select locations of the slurry feed inlet, water inlet, and xylene inlet. The five inlets from the bottom of the column were the bottom inlet below the bottom agitated stage (0-foot inlet), 2-foot, 4-foot, and 8-foot inlets, and the top inlet above the top agitated stage (10-foot inlet).

Two separate streams, as of an organic slurry feed mixture and an aqueous slurry feed mixture, were made accordingly. These two streams were pumped and metered separately, and were combined prior to entering the column to form the slurry feed mixture. The organic and aqueous slurry feed mixtures were prepared in stainless steel drums the day prior to the testing. The compositions of these two feed mixtures are listed in Table 15-A and 15-B, respectively.

TABLE 15-A

Composition of Organic Slurry Feed Mixture

| Component | Weight (g) | Calculated Concentration wt. % | ppm |
|---|---|---|---|
| xylene | 142242.03 | 92.22 | — |
| 2,5-dichlorophenol (2,5-DCP) | 11748.04 | 7.62 | — |
| 5-chloro-2-(2,4-dichlorophenoxy)-phenol (Triclosan) | 33.71 | 0.02 | 219 |
| 3-dichlorophenol (3-CP) | 32.00 | 0.02 | 207 |
| 2,5-dichloro-4-nitrophenol (2,5-DCNP) | 4.15 | 0.00 | 27 |
| 1,4-dichlorobenzene (1,4-DCB) | 11.30 | 0.01 | 73 |
| 4-chlorosalicylic acid (4-CSA) | 110.31 | 0.07 | 715 |
| acetic acid (AcOH) | 54.67 | 0.04 | 354 |
| potassium carbonate ($K_2CO_3$) | 4.70 | 0.00 | 30 |

TABLE 15-B

Composition of Aqueous Slurry Feed Mixture

| Component | Weight (g) | Calculated Concentration (wt. %) |
|---|---|---|
| water | 159687.19 | 89.17 |
| 2,5-dichlorophenol (2,5-DCP) | 2939.28 | 1.64 |
| 3,6-dichlorosalicylic acid (3,6-DCSA) | 7461.59 | 4.17 |
| potassium hydroxide (KOH) | 8990.20 | 5.02 |

The equipment set-up is shown in FIG. 5. There were several aspects for the equipment setup. The water was fed directly from a 5-gallon glass carboy. The xylene was fed directly from its drum. The aqueous slurry feed mixture was continuously mixed with a drum mixer during operation to ensure a homogeneous feed supply. All test experiments were performed at an elevated temperature with a target of approximately 70° C. in the agitation zone. The organic and aqueous slurry feed mixtures were heated by placing the drums in a drum oven overnight. During the operation, an electric band heater was placed on the aqueous feed drum to maintain the temperature. Heat exchangers were used to pre-heat the slurry feed mixture, xylene and water prior to entry in the column. Electrical heating tape was wrapped around the column to maintain the target temperature within the agitated zone. The corresponding temperatures, for example, T1 to T8, were recorded. FMI pumps were used for metering the slurry feed mixtures, xylene and water through mass flow meters and into the column. The 4-foot inlet from the bottom of the column was chosen for entering the slurry feed mixture into the column; the top inlet above the top agitated stage (10-foot inlet) was chosen as the water inlet; and the bottom inlet below the bottom agitated stage (0-foot inlet) was chosen as the xylene inlet. A FMI pump was used to discharge the heavy aqueous phase from the bottom of the column and manually control the interface in the upper disengaging chamber. The light organic phase was allowed to overflow from the column into the receiver. The aqueous and organic effluent flow rates were determined by periodic timed volumetric measurements.

The extraction experiment was conducted by following procedures: a) the column was initially filled with DI water to set the interface at the top of the column; b) when the column was full, the xylene flow was begun at the specified rate at an initial agitation of 50 SPM to observe phase behavior; c) the interface was established in the upper disengaging chamber, and then controlled by the discharging rate at the bottom of the column (i.e. requiring to set the discharge valve); d) the aqueous and organic feed pumps were turned on and set to the desired flow rates; e) after one column turnover (column volume divided by the combined aqueous and organic feed rates), the agitation was increased until set at the desired test speed; 0 for the first run, a total of five (5) column turnovers were performed before sampling the organic and aqueous effluent phases. Prior to sampling, organic and aqueous effluent rates were manually measured and recorded; g) for subsequent runs, after varying the parameters of each experiment, a total of three (3) turnovers were performed before sampling.

Different experimental runs were conducted by varying the aqueous and organic slurry, water and xylene inlet rates and the column agitation speed.

Example 12: Isolation of 3,6-Dichlorosalicylic Acid by Extraction (Test-1/Day-1 on KARR Column)

Example 11 was repeated with a slurry feed mixture for feasibility of extraction/isolation of 3,6-dichlorosalicylic acid and/or the K salt thereof (e.g. as solids) in a KARR column. The column was started up with the aqueous phase continuously at a scale-up capacity of 800 gph/ft$^2$ (flow rate/area of column diameter), and 85% by volume of the throughput was the combined organic and aqueous slurry feed mixtures. The aqueous and organic slurry feed mixtures, prepared in Example 11, were fed to the column in a ratio of 2.32 to 1 by weight. The fresh water and xylene were fed to the column in a 1:2 ratio by volume. The resulting feed rates were 156 g/min of aqueous slurry, 67 g/min of organic slurry, 14 g/min of water, and 24 g/min of xylene.

The feed rates of water, aqueous slurry, xylene, organic slurry, or the agitation speed varied for each experimental run. The operation conditions for four experimental runs are presented in Table 16-A.

TABLE 16-A

System Operation Conditions

| Exp. No. | scale-up capacity (gph/ft$^2$) | Slurry Feed Mixture | | | Water (g/min) | Xylene (g/min) | Agitation (SPM) | Temperature at T6 (° C.) |
| --- | --- | --- | --- | --- | --- | --- | --- | --- |
| | | Combined (vol %) | Aqueous (g/mL) | Organic (g/mL) | | | | |
| 12.1 | 800 | 85 | 156 | 67 | 14 | 24 | 120 | 72 |
| 12.2 | 800 | 85 | 156 | 67 | 14 | 24 | 140 | 74 |
| 12.3 | 1000 | 85 | 195 | 84 | 17 | 30 | 140 | 82 |
| 12.4 | 1000 | 85 | 195 | 84 | 34 | 30 | 140 | 71 |

In Experiment 12.1, the column agitation was set at 120 SPM. After five column turnovers, the organic and aqueous effluent streams were sampled. This was to determine if five turnovers were truly representative of steady state, since most of the flow was from the slurry feed mixture entering the midsection of the column and only a small portion of flow from water or xylene entering the top or bottom of the column. Operation of the column was continued for another three turnovers and the effluent streams were sampled again.

In Experiment 12.2, the column agitation was increased to 140 SPM. After three turnovers, the effluent streams were sampled.

Even with the increase of agitation, the column was not fully loaded. In Experiment 12.3, the scale-up capacity was increased to 1000 gph/ft$^2$, and corresponding increased flow rates of feed mixture, water and xylene were listed in Table 16-A. The agitation remained at 140 SPM. These rates increased the dispersed phase loading in the upper transition region where the plate spacing transited from 3-inch to 2-inch spacing. After three turnovers, the effluent streams were sampled.

In Experiment 12.4, the fresh water feed to the top of the column was doubled to 34 g/min while all other flows were maintained unchanged. After three turnovers, the effluent streams were sampled.

Table 16-B shows the extraction efficacy of 2,5-dichlorophenol, 3,6-dichlorosalicylic acid, and/or the K salt thereof for each run. Other impurities, for example, 4-chlorosalicylic acid (4-CSA), 5-chloro-2-(2,4-dichlorophenoxy)phenol (Triclosan), and 3-chlorophenol (3-CP) were measured as well in both organic and aqueous effluent streams.

TABLE 16-B

Extraction efficacy of Test-1/Day-1 on KARR Column

| Exp. No. | 3,6-DCSA (wt. %) | 2,5-DCP (wt. %) | 4-CSA (ppm) | 3-CP (ppm) | Triclosan (ppm) | 3,6-DCSA Partition (%)[a] | 2,5-DCP Partition (%)[a] |
|---|---|---|---|---|---|---|---|
| Aqueous | | | | | | | |
| Feed Mixture | 4.13 | 1.63 | — | <100 | <300 | — | — |
| 12.1a | 3.78 | 0.74 | — | <100 | <286 | 99.9 | 9.7 |
| 12.1b | 3.74 | 0.78 | — | <100 | <286 | 99.9 | 10.2 |
| 12.2 | 3.70 | 0.69 | — | <100 | <277 | 99.9 | 9.1 |
| 12.3 | 3.69 | 0.75 | — | <100 | <286 | 99.9 | 9.9 |
| 12.4 | 3.43 | 0.66 | — | <100 | <278 | 99.9 | 9.0 |
| Organic | | | | | | | |
| Feed Mixture | <28 | 7.89 | 697 | 182 | 229 | — | — |
| 12.1a | <14 | 6.89 | <11 | 124 | 169 | <0.1 | 90.3 |
| 12.1b | <14 | 6.90 | <11 | 121 | 170 | <0.1 | 89.8 |
| 12.2 | <14 | 6.88 | <11 | 123 | 170 | <0.1 | 90.9 |
| 12.3 | <14 | 6.79 | <11 | 124 | 169 | <0.1 | 90.1 |
| 12.4 | <14 | 6.64 | <11 | 122 | 113 | <0.1 | 91.0 |

[a]3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

Overall, there was no significant difference in the results from all of the test runs on Day-1. The study demonstrated the feasibility for performing the extraction via continuous processing in a 1-inch diameter KARR Column. The partition of 3,6-DCSA and/or the K salt thereof in the aqueous effluent was achieved in >99.5%; and the partition of 2,5-DCP and/or the K salt thereof in the aqueous effluent was reduced to be <10%.

Example 13: Isolation of 3,6-Dichlorosalicylic Acid by Extraction (Test-1/Day-2 on KARR Column)

Example 11 was repeated with a slurry feed mixture for feasibility of extraction/isolation of 3,6-dichlorosalicylic acid and/or the K salt thereof (e.g., as solids) in a KARR column. The column was started up with the aqueous phase continuously at a scale-up capacity of 1000 gph/ft$^2$ (flow rate/area of column diameter), and 85% by volume of the throughput was the combined organic and aqueous slurry feed mixtures. The aqueous and organic slurry feed mixtures, prepared in Example 11, were fed to the column in a ratio of 2.32 to 1 by weight. The fresh water and xylene were fed to the column in a 1:2 ratio by volume. The resulting feed rates were 195 g/min of aqueous slurry, 84 g/min of organic slurry, 17 g/min of water, and 30 g/min of xylene. The column agitation was set at 140 SPM.

The feed rates of water, aqueous slurry, xylene, organic slurry, or the agitation speed varied for each experimental run. In Experiment 13.4, HCl was added to the water feed entering the top of the column. The operation conditions for four experimental runs are presented in Table 17-A.

In Experiment 13.1, the operation conditions were the same as the ones in Experiment 12.3.

In Experiment 13.2, the scale-up capacity was increased to 1200 gph/ft$^2$, and corresponding increased flow rates of feed mixture, water and xylene were listed in Table 17-A. The agitation remained at 140 SPM.

In Experiment 13.3, the column agitation was increased to 180 SPM while maintaining other conditions the same.

In Experiment 13.4, 37% HCl was mixed with water to produce an acidic water feed that had HCl content of 0.76%. The scale-up capacity was decreased back to 1000 gph/ft$^2$. The intention was to sample the column after five turnovers and then again at the same conditions after an additional three turnovers. The acid addition caused some gas formation in the column that created instability with the interface control; therefore, extra time was used to get the column stable. The effluent streams were sampled with running time longer than the first five turnovers and sampled again after an additional three turnovers. The pH of the aqueous effluent was measured as of 8.9.

During the run with the acid addition, the column looked very different from prior runs. During prior runs without acid, the column had a light color as of a slight yellow tint at the top. The yellow color became more pronounced around the slurry feed point, and gradually became darker in the bottom part of the column. The aqueous effluent had an amber color. During the run with acid addition, the top three feet of the column remained the light color but the next two feet had an increasingly darker purple color that then transitioned into a dark yellow color just above the slurry inlet.

TABLE 17-A

System Operation Conditions

| Exp. No. | scale-up capacity (gph/ft$^2$) | Slurry Feed Mixture | | | Water (g/min) | Xylene (g/min) | Agitation (SPM) | Temperature at T6 (° C.) |
|---|---|---|---|---|---|---|---|---|
| | | Combined (vol %) | Aqueous (g/mL) | Organic (g/mL) | | | | |
| 13.1 | 1000 | 85 | 195 | 84 | 17 | 30 | 140 | 67 |
| 13.2 | 1200 | 85 | 234 | 101 | 21 | 36 | 140 | 67 |
| 13.3 | 1200 | 85 | 234 | 101 | 21 | 36 | 180 | 68 |
| 13.4 | 1000 | 85 | 195 | 84 | 17[a] | 30 | 140 | 71, 70 |

[a]37% HCl was mixed with water to produce an acidic water feed containing 0.76% HCl.

At the end of each run, the effluent streams were sampled. Table 17-B shows the extraction efficacy of 2,5-dichlorophenol, 3,6-dichlorosalicylic acid, and/or the K salt thereof for each run. Other impurities, for example, 4-chlorosalicylic acid (4-CSA), 5-chloro-2-(2,4-dichlorophenoxy)phenol (Triclosan), and 3-chlorophenol (3-CP) were measured as well in both organic and aqueous effluent streams.

to accommodate the acid feed location. The remaining inlets were remained the same as following: the 4-foot inlet from the bottom of the column was chosen for entering the slurry feed mixture into the column; the top inlet above the top agitated stage (10-foot inlet) was chosen as the water inlet; and the bottom inlet below the bottom agitated stage (0-foot inlet) was chosen as the xylene inlet.

TABLE 17-B

Extraction efficacy of Test-1/Day-2 on KARR Column

| Exp. No. | 3,6-DCSA (wt. %) | 2,5-DCP (wt. %) | 4-CSA (ppm) | 3-CP (ppm) | Triclosan (ppm) | 3,6-DCSA Partition (%)$^a$ | 2,5-DCP Partition (%)$^a$ | pH |
|---|---|---|---|---|---|---|---|---|
| Aqueous | | | | | | | | |
| Feed Mixture | 4.20 | 1.66 | — | <100 | <300 | — | — | 8.7 |
| 13.1 | 3.75 | 0.71 | — | <100 | <275 | 99.9 | 9.4 | — |
| 13.2 | 3.80 | 0.72 | — | <100 | <279 | 99.9 | 9.5 | — |
| 13.3 | 3.71 | 0.59 | — | <100 | <274 | 99.9 | 9.2 | — |
| 13.4a | 3.72 | 0.74 | — | <100 | <275 | 96.4 | 9.7 | 8.9 |
| 13.4b | 3.72 | 0.73 | — | <100 | <275 | 95.5 | 9.3 | 8.9 |
| Organic | | | | | | | | |
| Feed Mixture | <28 | 7.45 | 610 | 186 | 336 | — | — | — |
| 13.1 | <14 | 6.86 | <11 | 124 | 170 | <0.1 | 90.6 | — |
| 13.2 | <14 | 6.87 | <11 | 124 | 167 | <0.1 | 90.5 | — |
| 13.3 | <14 | 7.00 | <11 | 126 | 167 | <0.1 | 90.8 | — |
| 13.4a | 1396 | 6.91 | 82.5 | — | 166 | 3.6 | 90.3 | — |
| 13.4b | 1739 | 7.16 | 107 | — | 164 | 4.5 | 90.7 | — |

$^a$3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

The study confirmed the feasibility for performing the extraction via continuous processing in a 1-inch diameter KARR Column. Without acid feed, the partition of 3,6-DCSA and/or the K salt thereof in the aqueous effluent was achieved in >99.0%; and the partition of 2,5-DCP and/or the K salt thereof in the aqueous effluent was reduced to be <10%. With 0.76% HCl in water as the water feed entering from the top of the column, there was approximately 4 to 5% of 3,6-DCSA partitioned in the organic effluent.

Example 14: Isolation of 3,6-Dichlorosalicylic Acid by Extraction (Test-1/Day-3 on KARR Column)

Example 11 was repeated with a slurry feed mixture for feasibility of extraction/isolation of 3,6-dichlorosalicylic acid and/or the K salt thereof (e.g., as solids) in a KARR column with a modification of the location for the acid addition. The acid addition was moved to a location directly opposite to the slurry feed location at the 4-foot height from the bottom of the column. As a result, the T6 was removed The column was started up with the aqueous phase continuously at a scale-up capacity of 1000 gph/ft$^2$ (flow rate/area of column diameter), and 85% by volume of the throughput was the combined organic and aqueous slurry feed mixtures. The aqueous and organic slurry feed mixtures, prepared in Example 11, were fed to the column in a ratio of 2.32 to 1 by weight. The fresh water and xylene were fed to the column in a 1:2 ratio by volume. The resulting feed rates were 195 g/min of aqueous slurry, 84 g/min of organic slurry, 17 g/min of water, and 30 g/min of xylene. The column agitation was set at 140 SPM. The column was run for two turnovers before starting the acidic water feed.

The HCl concentration of the acidic water feed, the feed rates of the acidic water, water, aqueous slurry, xylene, organic slurry, the ratio of aqueous slurry to organic slurry, or the agitation speed varied for each experimental run. Temperature at T7 was listed since T6 was removed. The operation conditions for four experimental runs are presented in Table 18-A.

TABLE 18-A

System Operation Conditions

| Exp. No. | scale-up capacity (gph/ft$^2$) | HCl content (%) | Aq. HCl (g/min) | Slurry Feed Mixture | | | Water (g/min) | Xylene (g/min) | Agitation (SPM) | T7 (° C.) |
| | | | | Combined (vol %) | Aqueous (g/mL) | Organic (g/mL) | | | | |
|---|---|---|---|---|---|---|---|---|---|---|
| 14.1 | 1000 | 0.76 | 17 | 81 | 195 | 84 | 17 | 30 | 140 | 68 |
| 14.2 | 1000 | 1.52 | 17 | 81 | 195 | 84 | 17 | 30 | 140 | 70 |
| 14.3 | 1000 | 1.52 | 8 | 83 | 146 | 126 | 17 | 30 | 140 | 70 |
| 14.4 | 1200 | 1.52 | 10 | 83 | 176 | 151 | 21 | 36 | 120 | 67 |

In Experiment 14.1, the acidic water feed containing 0.76% HCl was fed to the 4-foot inlet of the column at 17 g/min. After the start of the acid feed, the column was operated for five turnovers and then sampled. The aqueous effluent had pH of 8.7.

In Experiment 14.2, the HCl concentration of the acidic water feed was increased to 1.52%, and all feed rates were maintained unchanged, as listed in Table 18-A. The agitation remained at 140 SPM. The aqueous effluent had pH of 8.5.

In Experiment 14.3, the ratio of aqueous slurry to organic slurry was decreased to 1.16 to 1 by weight. The corresponding flow rates of aq. HCl, feed mixture, water and xylene are listed in Table 18-A. The agitation remained at 140 SPM. The aqueous effluent had pH of 8.6.

In Experiment 14.4, the scale-up capacity was increased to 1200 gph/ft2 while keeping the same ratio (1.16 to 1 by weight) of aqueous slurry to organic slurry. The corresponding flow rates of aq. HCl, feed mixture, water and xylene are listed in Table 18-A. The agitation was decreased to 120 SPM. The aqueous effluent had pH of 8.6.

During this study with the acid addition, the rag layer formed at the interface in the column, and grew to a much larger size than previous studies. It was suggested that it may be caused by the salt formation with the acid addition.

At the end of each run, the effluent streams were sampled. Table 18-B shows the extraction efficacy of 2,5-dichlorophenol, 3,6-dichlorosalicylic acid, and/or the K salt thereof for each run. Other impurities, for example, 4-chlorosalicylic acid (4-CSA), 5-chloro-2-(2,4-dichlorophenoxy)phenol (Triclosan), and 3-chlorophenol (3-CP) were measured as well in both organic and aqueous effluent streams.

entering from the location directly opposite to the slurry feed location at the 4-foot height from the bottom of the column.

Example 15: Isolation of 3,6-Dichlorosalicylic Acid by Extraction (Test-1/Day-4 on KARR Column)

Example 11 was repeated with a slurry feed mixture for feasibility of extraction/isolation of 3,6-dichlorosalicylic acid and/or the K salt thereof (e.g., as solids) in a KARR column with the modified location for the acid addition described in Example 14. This test was to determine the effect of different amounts of acid fed to the column.

The column was started up with the aqueous phase continuously at a scale-up capacity of 1000 gph/ft$^2$ (flow rate/area of column diameter), and 85% by volume of the throughput was the combined organic and aqueous slurry feed mixtures. The aqueous and organic slurry feed mixtures, prepared in Example 11, were fed to the column in a ratio of 2.32 to 1 by weight. The fresh water and xylene were fed to the column in a 1:2 ratio by volume. The resulting feed rates were 195 g/min of aqueous slurry, 84 g/min of organic slurry, 17 g/min of water, and 30 g/min of xylene. The column agitation was set at 140 SPM. The column was run for two turnovers before starting the acidic water feed. The HCl content in the acidic water was 4.57% and maintained constant.

TABLE 18-B

Extraction efficacy of Test-1/Day-3 on KARR Column

| Exp. No. | 3,6-DCSA (wt. %) | 2,5-DCP (wt. %) | 4-CSA (ppm) | 3-CP (ppm) | Triclosan (ppm) | 3,6-DCSA Partition (%)$^a$ | 2,5-DCP Partition (%)$^a$ | pH |
|---|---|---|---|---|---|---|---|---|
| Aqueous | | | | | | | | |
| Feed Mixture | 4.13 | 1.63 | <124 | <30 | <95 | — | — | 8.7 |
| 14.1 | 3.46 | 0.60 | <291 | <70 | <220 | 99.9 | 8.0 | 8.7 |
| 14.2 | 4.06 | 0.55 | <290 | <70 | <220 | 99.9 | 7.3 | 8.5 |
| 14.3 | 3.53 | 0.44 | 480 | <70 | <220 | 99.9 | 6.0 | 8.6 |
| 14.4 | 3.60 | 0.49 | 457 | <70 | <220 | 99.9 | 6.6 | 8.6 |
| Organic | | | | | | | | |
| Feed Mixture | <30 | 7.35 | 645 | 187 | 228 | — | — | — |
| 14.1 | <30 | 6.89 | <23 | 125 | 165 | <0.1 | 92.0 | — |
| 14.2 | <30 | 7.03 | <23 | 127 | 166 | <0.1 | 92.7 | — |
| 14.3 | <30 | 6.86 | <23 | 144 | 179 | <0.1 | 94.0 | — |
| 14.4 | <30 | 6.90 | <23 | 145 | 181 | <0.1 | 93.4 | — |

$^a$3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

The study again demonstrated the feasibility for performing the extraction via continuous processing with an additional acidic water feed in a 1-inch diameter KARR Column. The partition of 3,6-DCSA and/or the K salt thereof in the aqueous effluent was achieved in >99.5%; and the partition of 2,5-DCP and/or the K salt thereof in the aqueous effluent was reduced to be <8%, when the 0.76% HCl in water was The HCl concentration of the acidic water feed, the feed rates of the acidic water, water, aqueous slurry, xylene, organic slurry, the ratio of aqueous slurry to organic slurry, or the agitation speed varied for each experimental run. Temperature at T7 was listed since T6 was removed. The operation conditions for four experimental runs are presented in Table 19-A.

TABLE 19-A

| | | | System Operation Conditions | | | | | | |
|---|---|---|---|---|---|---|---|---|---|
| | scale-up | | Slurry Feed Mixture | | | | | | |
| Exp. No. | capacity (gph/ft$^2$) | Aq. HCl (g/min) | Combined (vol %) | Aqueous (g/mL) | Organic (g/mL) | Water (g/min) | Xylene (g/min) | Agitation (SPM) | T7 (° C.) |
| 15.1 | 1000 | 17 | 81 | 195 | 84 | 17 | 30 | 140 | 66 |
| 15.2a | 1000 | 34 | 77 | 195 | 84 | 17 | 30 | 140 | 66 |
| 15.2b | 1000 | 34 | 77 | 195 | 84 | 17 | 30 | 140 | 67 |
| 15.3 | 1000 | 26 | 79 | 195 | 84 | 17 | 30 | 140 | 68 |
| 15.4 | 1000 | 11 | 82 | 195 | 84 | 17 | 30 | 140 | 69 |

In Experiment 15.1, the acidic water feed containing 4.57% HCl was fed to the 4-foot inlet of the column at 17 g/min. After the start of the acid feed, the column was operated for five turnovers and then sampled. The aqueous effluent had pH of 8.1. It was observed that the dispersed phase had different mixings compared to previous runs (e.g., Example 12, 13, and 14). The dispersed phase above the slurry feed inlet had much larger droplet sizes and was less well dispersed; and the dispersed phase below the slurry feed inlet had fine droplets and a very good mixing.

In Experiment 15.2, the acidic water feed rate was increased to 34 g/min, and all other parameters were maintained unchanged, as listed in Table 19-A. After three turnovers, the aqueous effluent had pH of 4.1. After sampling, the column was allowed to run an additional three turnovers, and the aqueous effluent had pH of 4.0.

In Experiment 15.3, the acidic water feed rate was decreased to 26 g/min, and all other parameters were maintained unchanged, as listed in Table 19-A. The aqueous effluent had pH of 7.7.

In Experiment 15.4, the acidic water feed rate was decreased further to 11 g/min, and all other parameters were maintained unchanged, as listed in Table 19-A. The aqueous effluent had pH of 8.4.

During this study with more acid addition, the rag layer at the interface in the column was observed to less than previous studies (Example 14).

At the end of each run, the effluent streams were sampled. Table 19-B shows the extraction efficacy of 2,5-dichlorophenol, 3,6-dichlorosalicylic acid, and/or the K salt thereof for each run. Other impurities, for example, 4-chlorosalicylic acid (4-CSA), 5-chloro-2-(2,4-dichlorophenoxy)phenol (Triclosan), and 3-chlorophenol (3-CP) were measured as well in both organic and aqueous effluent streams.

TABLE 19-B

| | | | Extraction efficacy of Test-1/Day-4 on KARR Column | | | | | |
|---|---|---|---|---|---|---|---|---|
| Exp. No. | 3,6-DCSA (wt. %) | 2,5-DCP (wt. %) | 4-CSA (ppm) | 3-CP (ppm) | Triclosan (ppm) | 3,6-DCSA Partition (%)$^a$ | 2,5-DCP Partition (%)$^a$ | pH |
| | | | | Aqueous | | | | |
| Feed Mixture | 4.13 | 1.63 | <100 | <26 | <80 | — | — | 8.7 |
| 15.1 | 0.65 | 0.26 | 214 | 27 | <38 | 89.2 | 3.4 | 8.1 |
| 15.2a | 1.81 | 0.10 | 142 | <12 | <38 | 82.8 | 1.3 | 4.1 |
| 15.2b | 1.55 | 0.10 | 138 | <12 | <38 | 81.7 | 1.3 | 4.0 |
| 15.3 | 1.27 | 0.18 | 166 | <12 | <38 | 84.1 | 2.3 | 7.7 |
| 15.4 | 0.54 | <12 ppm | 234 | <12 | <38 | 92.5 | 0 | 8.4 |
| | | | | Organic | | | | |
| Feed Mixture | <30 | 7.39 | 650 | 188 | 227 | — | — | — |
| 15.1 | 788 | 7.44 | 76.6 | 126 | 164 | 10.8 | 96.6 | — |
| 15.2a | 3760 | 7.66 | 207 | 129 | 163 | 17.2 | 98.7 | — |
| 15.2b | 3480 | 7.68 | 181 | 126 | 162 | 18.3 | 98.7 | — |
| 15.3 | 2400 | 7.51 | 151 | 127 | 162 | 15.9 | 97.7 | — |
| 15.4 | 439 | 7.20 | 53.8 | 126 | 161 | 7.5 | 100 | — |

$^a$3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

This study demonstrated that the higher the acid addition, the lower the pH of the aqueous effluent, the lower partition of 3,6-DCSA and/or the K salt thereof in the aqueous effluent, and the lower loss of 2,5-DCP and/or the K salt thereof in the aqueous effluent. There are significant amounts of 3,6-DCSA and/or the K salt thereof in the organic effluent, when a higher content of HCl in water as the acidic water feed was entering to the column.

Example 16: General Procedure-2 for Isolation of 3,6-Dichlorosalicylic Acid by Extraction (KARR Column)

For the pilot plant test, the KARR Column, described in Example 2, was used. Variable plate spacing was used in the column. The slurry inlet was located at the midpoint of the column where a 6-inch spacing was centered. Below the slurry feed inlet, the plate stacking order was: two plates with 3-inch spacing and remaining with standard 2-inch spacing. Above the slurry feed inlet, the plate stacking order was: two plates with 4-inch spacing, two plates with 3-inch spacing, and remaining with standard 2-inch spacing.

The slurry feed mixture was prepared in stainless steel reactor vessel on the same day prior to the testing. The compositions of a representative feed mixture are listed in Table 20.

TABLE 20

Composition of a Slurry Feed Mixture

| Component | Weight (g) | Calculated Concentration (wt. %) |
|---|---|---|
| water | 5035 | 21.70 |
| xylene | 9752 | 43.96 |
| 40% 2,5-dichlorophenol (2,5-DCP) in xylene | 15150 | 14.14 |
| 3,6-dichlorosalicylic acid (3,6-DCSA) | 5171 | 12.06 |
| 45% potassium hydroxide (KOH) in water | 7756 | 8.14 |

The equipment set-up is shown in FIG. 6. There were several aspects for the equipment setup. The slurry mixture feed entered the column through the midpoint; water entered from the top inlet (10-foot inlet); xylene entered from the bottom inlet (0-foot inlet). All test experiments were performed at an elevated temperature with a target of approximately 75° C. in the agitation zone. The slurry feed mixtures were heated by a hot-oil jacket surrounding the reactor vessel in which the mixture was prepared. Heat exchangers were used to pre-heat xylene and water prior to entry in the column. Electrical heating tape was wrapped around the column to maintain the target temperature within the agitated zone and some sections of the column were insulated. The corresponding temperatures, for example, T1 to T10, were recorded. FMI pumps were used for metering xylene and water through mass flow meters and into the column. The slurry feed was fed to the column either by a gear pump or by a FMI pump; and the flow rate was not metered. A FMI pump was used to discharge the heavy aqueous phase from the bottom of the column and manually control the interface in the upper disengaging chamber. The light organic phase was allowed to overflow from the column into the receiver. The aqueous and organic effluent flow rates were determined by periodic timed volumetric measurements.

The extraction experiment was conducted by following procedures: a) the column was initially filled with DI water to set the interface at the top of the column; b) when the column was full, the xylene flow was begun at the specified rate at an initial agitation of 60 SPM to observe phase behavior; c) the interface was established in the upper disengaging chamber, and then controlled by the discharging rate at the bottom of the column (i.e. requiring to set the discharge valve); d) the slurry feed pump was turned on and set to the desired flow rates; e) timed outflow measurements were taken to determine the slurry feed rate; f) the xylene and water feed flow rates were adjusted based on the measured slurry feed rate; g) after one column turnover (column volume divided by the combined aqueous and organic feed rates), the agitation was increased until set at the desired test speed; h) for the first run, a total of five (5) column turnovers were performed before sampling the organic and aqueous effluent phases. Prior to sampling, organic and aqueous effluent rates were manually measured and recorded; i) for subsequent runs, after varying the parameters of each experiment, a total of three (3) turnovers were performed before sampling.

Different experimental runs were conducted by varying the slurry, water and xylene inlet rates and the column agitation speed.

Example 17: Isolation of 3,6-Dichlorosalicylic Acid by Extraction (Test-2/Day-1 on KARR Column)

Example 16 was repeated with a slurry feed mixture for feasibility of extraction/isolation of 3,6-dichlorosalicylic acid and/or the K salt thereof (e.g. as solids) in a KARR column. This test was to determine parameters for handling a slurry feed mixture with a minimum water content.

The slurry feed mixtures in the reactor vessel, prepared in Example 16, was continuously agitated at a temperature of 80° C., and was fed with a gear pump with a continuous recirculating back to the reactor vessel. The gear pump was controlled with a variable speed controller to set the feed rate. The feed rate of the slurry was initially measured. The column was started up with an initial scale-up capacity of 740 gph/ft$^2$ (flow rate/area of column diameter) for the top half of the column. The corresponding feed rates were 135 g/min of the slurry (i.e., measured), 160 g/min of water, and 14.5 g/min of xylene. When outflow rates of the aqueous and organic effluents were measured, the slurry feed rate was calculated to be much lower than the measured value; therefore, the slurry feed rate was reported by calculation based on the measured outflow rates of the aqueous and organic effluents. The column agitation was initially set at 100 SPM.

The feed rates of the slurry, water, xylene, the top half column capacity, or the agitation speed varied for each experimental run. Temperature at T4 (at the middle of the column) was listed. The operation conditions for five experimental runs are presented in Table 21-A.

TABLE 21-A

System Operation Conditions

| Exp. No. | Top column capacity (gph/ft$^2$) | Slurry Feed Mixture (g/min) | Water (g/min) | Xylene (g/min) | Agitation (SPM) | T7 (° C.) |
|---|---|---|---|---|---|---|
| 17.1 | 633 | 35 | 178 | 16 | 100 | 76 |
| 17.2 | 653 | 101 | 150 | 12 | 100 | 77 |
| 17.3 | 629 | 87 | 150 | 12 | 120 | 75 |
| 17.4 | 1404 | 174 | 354 | 21 | 80 | 75 |
| 17.5 | 1053 | 193 | 225 | 18 | 80 | 75 |

In Experiment 17.1, the slurry feed rate was increased and initially measured. The subsequent flow rates of water and xylene were adjusted accordingly. However, the calculated slurry mixture feed rate was only 35 g/min, resulting in much higher ratios of water to the slurry feed and xylene to the slurry feed.

For the following experiments, the slurry feed pump was adjusted and outflow rates of the aqueous and organic effluents were used to determine the slurry feed rate prior to the start of each run. The calculated slurry feed rate was used to set the water and xylene feed rates at the correct ratio.

In Experiment 17.2, the slurry feed rate was measured to be 115 g/min at the beginning of the run. The subsequent flow rates of water and xylene feed rates were adjusted accordingly. However, the calculated slurry feed rate by outflows during the run was 101 g/min. As a result, the water and xylene feed rates were slightly higher than designed for this slurry feed rate but much closer than the ones in Exp.

17.1. The scale-up capacity for this run for the top half of the column was 653 gph/ft², below the designed initial conditions.

In Experiment 17.3, all feed rates of the slurry mixture, water, and xylene was remained unchanged. The column agitation was increased to 120 SPM. The calculated slurry feed rate by outflows during the run was 87 g/min, lower than the value in Exp. 17.2.

In Experiment 17.4, the water flow rate was increased to about 250 g/min prior to increasing the slurry feed rate to assure all solids being dissolved in the outflows. The slurry feed rate was then increased to 200 g/min based on the initial outflow measurements. The xylene feed rate was set to 21 g/min based on these two rates. The column agitation was initially set at 100 SPM. There were some solids that were not dissolving so the agitation was reduced to 80 SPM and the water flow rate was increased to 354 g/min. The calculated slurry feed rate by outflows during the run was 174 g/min. The scale-up capacity in the top of column was calculated to be 1404 gph/ft² due to using significant excess water.

In Experiment 17.5, the water and xylene flow rates were lowered so the ratios of water to the slurry feed and xylene to the slurry feed were closer to the designed one. The calculated slurry feed rate by outflows during the run was 193 g/min. The corresponding scale-up capacity in the top of column was calculated to be 1053 gph/ft².

At the end of each run, the effluent streams were sampled and analyzed. Table 21-B shows the extraction efficacy of 2,5-dichlorophenol, 3,6-dichlorosalicylic acid, and/or the K salt thereof for each run.

TABLE 21-B

Extraction efficacy of Test-2/Day-1 on KARR Column

| Exp. No. | Phase | 3,6-DCSA (wt. %) | 2,5-DCP (wt. %) | 3,6-DCSA Partition (%)[a] | 2,5-DCP Partition (%)[a] |
|---|---|---|---|---|---|
| Feed Mixture | slurry | 10.27 | 13.29 | — | — |
| 17.1 | Aqueous | 2.27 | 1.66 | >99.9 | 17.8 |
| 17.2 |  | 6.46 | 4.32 | >99.9 | 25.9 |
| 17.3 |  | 5.63 | 3.77 | >99.9 | 23.9 |
| 17.4 |  | 4.44 | 3.14 | >99.9 | 22.0 |
| 17.5 |  | 5.17 | 3.68 | >99.9 | 25.1 |
| 17.1 | Organic | <0.0003 | 7.64 | 0 | 82.2 |
| 17.2 |  | 0 | 12.37 | 0 | 74.1 |
| 17.3 |  | 0 | 11.99 | 0 | 76.1 |
| 17.4 |  | 0.0006 | 11.15 | 0 | 78.0 |
| 17.5 |  | 0 | 10.99 | 0 | 74.9 |

[a]3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

Throughout the entire study, the slurry feed rate was inconsistent and difficult to control. As a result, it made it difficult to maintain the desired ratios of water and xylene to the slurry feed. However, the partition of 3,6-DCSA and/or the K salt thereof in the aqueous effluent was still achieved in >99.9%. The 3,6-DCSA and/or the K salt thereof in the organic effluent was under 10 ppm.

Under conditions of these five experiments, it was noted that the solids in the slurry dropped down in the column upon entry. As the solids broke up with agitation and dissolved, xylene was released upward in the column.

Example 18: Isolation of 3,6-Dichlorosalicylic Acid by Extraction (Test-2/Day-2 on KARR Column)

Example 16 was repeated with a slurry feed mixture for feasibility of extraction/isolation of 3,6-dichlorosalicylic acid and/or the K salt thereof (e.g. as solids) in a KARR column. This test was to determine parameters for handling a slurry feed mixture with a minimum water content.

An additional FMI pump (as a calibrate pump) was installed at the discharge of the gear pump that was used previously (in Example 17) to send the slurry feed mixtures in the reactor vessel to the column. The gear pump was set to continuously recirculate the slurry feed from the FMI pump back to the reactor vessel. The column was started up with an initial calculated slurry feed rate of 170 g/min and it was used to set the water and xylene feed rates at the correct ratio. The column agitation was initially set at 100 SPM.

The feed rates of the slurry, water, xylene, the top half column capacity, or the agitation speed varied for each experimental run. Temperature at T4 (at the middle of the column) was listed. The operation conditions for five experimental runs are presented in Table 22-A.

TABLE 22-A

System Operation Conditions

| Exp. No. | Top column capacity (gph/ft²) | Slurry Feed Mixture (g/min) | Water (g/min) | Xylene (g/min) | Agitation (SPM) | T7 (° C.) |
|---|---|---|---|---|---|---|
| 18.1 | 925 | 158 | 202 | 18 | 100 | 81 |
| 18.2 | 1295 | 235 | 275 | 25 | 80 | 82 |
| 18.3 | 1123 | 197 | 242 | 22 | 100 | 82 |
| 18.4 | 1107 | 188 | 242 | 22 | 100 | 75 |

In Experiment 18.1, the calculated slurry feed rate during the run was 158 g/min.

In Experiment 18.2, the calculated slurry feed rate was increased to 230 g/min and subsequent flow rates of water and xylene feed rates were adjusted accordingly. The column began to flood immediately above the slurry inlet with the phases reversing, so the column agitation was reduced to 80 SPM. The calculated slurry feed rate was 235 g/min during the run.

In Experiment 18.3, the calculated slurry feed rate was decreased to 197 g/min and subsequent flow rates of water and xylene feed rates were adjusted accordingly. The column agitation was returned back to 100 SPM.

In Experiment 18.4, the slurry feed inlet was moved one foot higher in the column. As a result, the slurry feed inlet was now in a section of four-inch plate spacing with more open spacing below the feed. All flow rates were maintained approximately the same as the ones in Exp. 18.3, and the column agitation was kept at 100 SPM. With more open spacing below the feed, the solids appeared to move marginally different being slightly further down in the column before dissolving. No difference was observed in the column above the feed point.

At the end of each run, the effluent streams were sampled and analyzed. Table 22-B shows the extraction efficacy of 2,5-dichlorophenol, 3,6-dichlorosalicylic acid, and/or the K salt thereof for each run.

TABLE 22-B

Extraction efficacy of Test-2/Day-2 on KARR Column

| Exp. No. | Phase | 3,6-DCSA (wt. %) | 2,5-DCP (wt. %) | 3,6-DCSA Partition (%)[a] | 2,5-DCP Partition (%)[a] |
|---|---|---|---|---|---|
| Feed Mixture | slurry | 10.27 | 13.29 | — | — |
| 18.1 | Aqueous | 6.66 | 3.92 | >99.9 | 23.1 |
| 18.2 | | 7.16 | 4.28 | >99.9 | 25.0 |
| 18.3 | | 6.74 | 4.05 | >99.9 | 23.9 |
| 18.4 | | 7.35 | 4.15 | >99.9 | 23.3 |
| 18.1 | Organic | 0 | 13.05 | 0 | 76.9 |
| 18.2 | | 0 | 12.81 | 0 | 75.0 |
| 18.3 | | 0 | 12.92 | 0 | 76.1 |
| 18.4 | | 0 | 13.69 | 0 | 76.7 |

[a] 3,6-DCSA partition in each phase was calculated based on the total amount of 3,6-DCSA in both aqueous and organic effluents; 2,5-DCP partition in each phase was calculated based on the total amount of 2,5-DCP in both aqueous and organic effluents.

With changes made in the slurry feed configuration, the slurry feed rate was consistently controlled. Therefore, the ratios of water to the slurry feed and xylene to the slurry feed could be maintained much closer to those desired. The partition of 3,6-DCSA and/or the K salt thereof in the aqueous effluent was achieved in >99.9%; and the partition of 2,5-DCP and/or the K salt thereof in the aqueous effluent was reduced to be <25%. The 3,6-DCSA and/or the K salt thereof in the organic effluent was nearly not detectable.

The study clearly demonstrated the feasibility for performing the extraction via continuous processing in a KARR Column. As long as a sufficient amount of water was used and the temperature maintained above 75° C., it was observed that the solids were able to well dissolve in the water phase before moving to the bottom of the column. The recovery of 3,6-DCSA and/or the K salt thereof in over 99.5% was feasible.

Example 19: Dehydration of 2,5-Dichlorophenol Salt Feed Mixture

Figure 7:
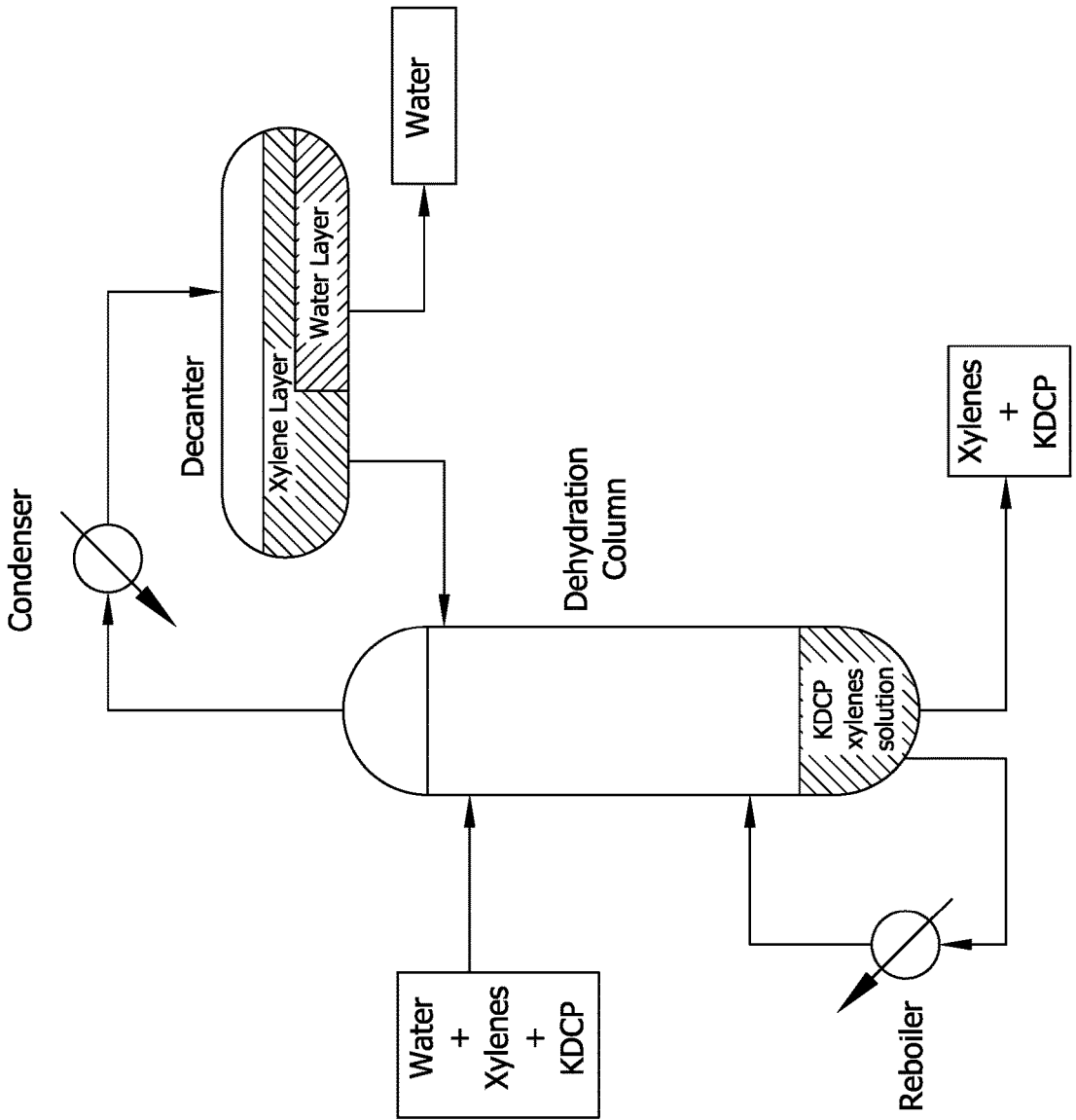
FIG. 7 depicts a dehydration column and associated equipment suitable for use in the process described in Example 19.

Following is a method for dehydration of a 2,5-DCP salt-containing feed mixture as shown in FIG. 7. The feed mixture contains water, xylene, and the potassium salt of 2,5-DCP. Feed the mixture to the column at a stage near the top. Heat the solution to a boil and produce a vapor phase that exits the top of the column and is sent to the condenser. Collect the condensate from the condenser in a decanter where the condensate forms two liquid layers: a heavier water-rich layer and lighter xylene-rich layer. Recover the xylene-rich layer and return to the column at a point between the feed location of the feed mixture and the top of the column. Collect the bottoms fraction of the column which is enriched in xylene and potassium 2,5-DCP.

Example 20: Dehydration of 2.5-Dichlorophenol Salt Feed Mixture

A distillation system as shown in FIG. 10 was set up to dehydrate a potassium 2,5-DCP salt in water solution to produce the potassium salt of 2,5-DCP in xylene solution. As shown in FIG. 10, the distillation system comprised a condenser, a decanter, a distillation column containing more than 10 perforated trays, and a stillpot with external heating mantle. To begin distillation, 500 grams of xylene was charged to the stillpot and heated to boil. Xylene vapor rose through the perforated trays inside the distillation column and was liquefied in the condenser and refluxed back to the distillation column from the decanter. After the system reached steady state, the potassium salt of 2,5-DCP in water solution was pumped into the distillation column at the flow rate of 1 mL/min. Water was collected in the decanter and removed periodically. Feed of the potassium salt of 2,5-DCP in water was stopped after 2 hours. The solution in the stillpot was analyzed and determined to contain approximately 200 ppm water and approximately 19% potassium salt of 2,5-DCP by weight in xylene.

Example 21: Dehydration of 2,5-Dichlorophenol Salt Feed Mixture

The distillation system described in Example 20 was used to dehydrate another potassium 2,5-DCP sat in water solution. All conditions described in Example 20 were followed except in this additional experiment feed of the potassium salt of 2,5-DCP salt in water was stopped after 5 hours.

The solution in the stillpot was analyzed and determined to contain approximately 350 ppm water and approximately 49% potassium salt of 2,5-DCP by weight in xylene.

EMBODIMENTS

For further illustration, additional non-limiting embodiments of the present invention are set forth below.

Embodiment A is a process for dehydrating a chlorophenol salt feed mixture, the process comprising:
providing a feed mixture comprising a chlorophenol salt, water, and an organic solvent;
distilling the feed mixture within a distillation zone, thereby forming an overheads fraction comprising water and a portion of the organic solvent and a bottoms fraction comprising the chlorophenol salt and a portion of the organic solvent, the bottoms fraction being enriched in chlorophenol salt as compared to the overheads fraction;
condensing the overheads fraction to form a recycle stream comprising recovered organic solvent and water;
removing water from the recycle stream; and
feeding the recycle stream comprising recovered organic solvent to the distillation zone.

Embodiment A1 is the process of embodiment A wherein the distillation zone comprises a column comprising one or more intermediate stages to which the feed mixture is fed, the distillation zone further comprising a rectifying zone comprising one or more rectifying stages above the one or more intermediate stages, and a stripping zone comprising one or more stripping stages below the one or more intermediate stages.

Embodiment A2 is the process of embodiment A1 wherein the recycle stream comprising organic solvent is fed to the rectifying zone.

Embodiment A3 is the process of any of embodiments A to A2 wherein the overheads fraction is removed from the distillation zone as the recycle stream is fed to the rectifying zone.

Embodiment A4 is the process of any of embodiments A to A3 wherein the chlorophenol salt comprises the potassium salt of 2,5-DCP, the sodium salt of 2,5-DCP, or a combination thereof.

Embodiment A5 is the process of any of embodiments A to A4 wherein the organic solvent has a normal boiling point greater than 100 C°.

Embodiment A6 is the process of any of embodiments A to A5 wherein the organic solvent is selected from the group consisting of xylene, toluene, benzene, and combinations thereof.

Embodiment A7 is the process of embodiment A6 wherein the organic solvent comprises xylene.

Embodiment A8 is the process of any of embodiments A to A7 wherein the mass ratio of organic solvent to chlorophenol salt in the feed mixture is from about 0.2:1 to about 3:1, from about 0.5:1 to about 2.5:1, or from about 1:1 to about 2:1.

Embodiment A9 is the process of any of embodiments A to A8 wherein the mass ratio of water to chlorophenol salt in the feed mixture is from about 0.2:1 to about 2:1, from about 0.2:1 to about 1:1, or about 0.5:1.

Embodiment A10 is the process of any of embodiments A to A9 wherein an intermediate feed mixture comprising the chlorophenol salt and water is combined with the organic solvent to form the feed mixture.

Embodiment A11 is the process of embodiment A10 wherein the organic solvent is present within the distillation zone when combined with the intermediate feed mixture.

Embodiment A12 is the process of embodiment A11 wherein the temperature of the organic solvent within the distillation zone is at least about 60° C., at least about 70° C., at least about 80° C., or at least about 90° C.

Embodiment A13 is the process of any of embodiments A10 to A12 wherein water is removed from the intermediate feed mixture prior to being combined with the organic solvent.

Embodiment A14 is the process of embodiment A13 wherein water is removed from the intermediate feed mixture by flash evaporation.

Embodiment A15 is the process of any of embodiments A10 to A14 wherein the temperature of the intermediate feed mixture combined with the organic solvent is at least about 30° C., at least about 60° C., at least about 90° C., at least about 120° C., or at least about 150° C.

Embodiment A16 is the process of any of embodiments A10 to A15 wherein the temperature of the intermediate feed mixture combined with the organic solvent is from about 30° C. to about 200° C., from about 60° C. to about 200° C., from about 90° C. to about 200° C., from about 120° C. to about 200° C., or from about 150° C. to about 200° C.

Embodiment A17 is the process of any of embodiments A to A16 wherein the temperature within the distillation zone ranges from about 70° C. to about 150° C., from about 80° C. to about 150° C., from about 90° C. to about 150° C., from about 100° C. to about 200° C., from about 110° C. to about 200° C., or from about 120° C. to about 200° C.

Embodiment A18 is the process of any of embodiments A to A18 wherein the overheads fraction comprises a minimum boiling azeotrope comprising the organic solvent and water, the overheads fraction having a boiling point less than the boiling point of any combination of its constituents.

Embodiment A19 is the process of any of embodiments A to A19 wherein water is removed from the recycle stream by a liquid-liquid separation method selected from the group consisting of decanting, extraction, mixing/settling, centrifugation, and combinations thereof.

Embodiment A20 is the process of any of embodiments A to A19 further comprising recovering the bottoms fraction, wherein the bottoms fraction contains less than about 0.1 wt % water, less than about 0.05 wt % water, less than about 0.02 wt % water, less than about 0.01 wt % water, less than about 0.005 wt % water, or less than about 0.001 wt % water.

Embodiment A21 is the process of any of embodiments A to A20 wherein the bottoms fraction contains at least about 10 wt %, at least about 15 wt %, at least about 20 wt %, at least about 25 wt %, at least about 30 wt %, at least about 35 wt %, or at least about 40 wt % chlorophenol salt.

Embodiment A22 is the process of any of embodiments A to A21 wherein the bottoms fraction contains at least about 45 wt %, at least about 50 wt %, at least about 55 wt %, or at least about 60 wt % of the organic solvent.

Embodiment A23 is the process of any of embodiments A to A22, further comprising recovering a chlorophenol salt from the bottoms fraction and wherein the chlorophenol salt is the potassium salt of 2,5-DCP.

Embodiment A24 is the process of embodiment A23 wherein the potassium salt of 2,5-DCP is converted to dicamba.

Embodiment A25 is the process of embodiment A23, further comprising carboxylating the salt of 2,5-DCP in the recovered bottoms fraction removed from the distillation zone to form 3,6-dichlorosalicylic acid or a salt thereof.

Embodiment A26 is the process of embodiment A25, further comprising methylating 3,6-dichlorosalicylic acid or a salt thereof with a methylating agent to form 3,6-dichloro-2-methoxybenzoic acid or salt thereof and/or methyl 3,6-dichloro-2-methyoxybenzoate.

Embodiment A27 is the process of embodiment A26, further comprising saponifying methyl 3,6-dichloro-2-methyoxybenzoate with a base to form a salt of 3,6-dichloro-2-methoxybenzoic acid.

Embodiment A28 is the process of any of embodiments A to A27 further comprising contacting a crude product stream comprising 2,5-dichlorophenol (2,5-DCP) and organic impurities comprising phenolic impurities with an aqueous base in a neutralization/extraction zone to at least partially deprotonate the 2,5-DCP and phenolic impurities and form an intermediate feed mixture comprising the salt of 2,5-DCP and phenolic impurities and water and an organic fraction comprising organic impurities transferred from the crude product stream.

Embodiment A29 is the process of embodiment A28 wherein the phenolic impurities present in the crude product stream are selected from 2-chlorophenol (2-CP), 2,4-dichlorophenol (2,4-DCP), 3-chlorophenol (3-CP), 4-chlorophenol (4-CP), and combinations thereof.

Embodiment A30 is the process of embodiment A28 or A29 wherein the organic impurities comprise one or more impurities selected from the group consisting of 3,4-dichlorophenol (3,4-DCP), 2,5-dichloronitrobenzene (2,5-DCNB), 3,6-dichloro-1,5-dinitrobenzene (3,6-DC-1,5-DNB), 2,5-dichloro-4-nitrophenol (2,5-DC-4-NP), 1,4-dichloro-2-(2,4-dichlorophenoxy)benzene (2,5-2,4-TCDPE), 2-chloro-5-(2,5-dichlorophenoxy)phenol (CDPP), and combinations thereof, which are removed from the crude product stream by distillation and/or liquid-liquid extraction prior to contacting the aqueous base.

Embodiment A31 is the process of any of embodiments A28 to A30 wherein the aqueous base is a hydroxide of an alkali metal or alkaline earth metal.

Embodiment A32 is the process of any of embodiments A28 to A31 wherein the intermediate feed mixture constitutes at least a portion of the feed mixture.

Embodiment B is a process for preparation and recovery of 3,6-dichlorosalicylic acid (3,6-DCSA) and/or a salt thereof, the process comprising:

carboxylating 2,5-dichlorophenol (2,5-DCP) and/or a salt thereof in an organic reaction medium comprising an organic solvent, thereby forming a carboxylation product slurry comprising the organic solvent, 3,6-DCSA and/or one or more salts thereof, unreacted 2,5-DCP and/or a salt thereof, and one or more impurities;

feeding the carboxylation product slurry to a fractional liquid-liquid extraction (FLLE) zone;

feeding an organic solvent to the FLLE zone;

feeding an aqueous medium to the FLLE zone;

contacting the carboxylation product slurry with the organic solvent and the aqueous medium in the FLLE zone, wherein at least a portion of the unreacted 2,5-DCP and/or a salt thereof and the one or more impurities are transferred to an organic phase comprising the organic solvent and at least a portion of the 3,6-DCSA or a salt thereof is transferred to an aqueous phase;

recovering an aqueous phase extract comprising one or more salts of 3,6-DCSA from the FLLE zone, wherein the weight ratio of salts of 3,6-DCSA to 2,5-DCP in the aqueous phase extract is greater than the weight ratio of salts of 3,6-DCSA to 2,5-DCP in the carboxylation feed mixture;

recovering an organic phase extract comprising 2,5-DCP, the organic solvent and one or more impurities from the FLLE zone; and neutralizing the salts of 3,6-DCSA in the aqueous phase extract to form a product mixture comprising 3,6-DCSA.

Embodiment B1 is the process of embodiment B, wherein the FLLE zone comprises at least one vertical column having a feed location for the carboxylation product slurry, a stripping section, and a rectifying section, wherein the stripping section is the portion of the column situated beneath the feed location and the rectifying section is the portion of the column situated above the feed location.

Embodiment B2 is the process embodiment B1, wherein the aqueous phase extract is recovered from the stripping section of the FLLE zone, and the organic phase extract is recovered from the rectifying section of the FLLE extraction zone.

Embodiment B3 is the process of any of embodiments B to B2 wherein the carboxylation product slurry comprises the organic carboxylation reaction medium, unreacted 2,5-DCP and/or a salt thereof, and product solids comprising one or more salts of 3,6-DCSA.

Embodiment B4 is the process of any of embodiments B to B3 wherein the carboxylation product slurry has a water content of less than about 1 wt %, less than about 0.7 wt %, less than about 0.5 wt %, less than about 0.2 wt %, less than about 0.1 wt %, less than about 0.05 wt %, less than about 0.02 wt %, or less than about 0.01 wt %.

Embodiment B5 is the process of any of embodiments B to B4 wherein the carboxylation product slurry has a solids content of at least about 20 wt %, at least about 30 wt %, at least about 40 wt %, at least about 50 wt %, at least about 60 wt %, at least about 70 wt %, or at least about 80 wt %.

Embodiment B6 is the process of any of embodiments B to B5 wherein the organic solvent constitutes at least about 20 wt %, at least about 30 wt %, at least about 40 wt %, or at least about 50 wt % of the carboxylation product slurry.

Embodiment B7 is the process of any of embodiments B to B6 wherein the carboxylation product mixture is agitated prior to and/or during contact with the organic solvent and aqueous medium in the FLLE zone.

Embodiment B8 is the process of any of embodiments B to B7 wherein the FLLE extraction zone is agitated during contact of the carboxylation product slurry, organic solvent, and aqueous medium therein.

Embodiment B9 is the process of any of embodiments B to B8 wherein the ratio of the mass flow rates for the aqueous medium to the carboxylation product slurry fed to the FLLE extraction zone is at least about 1:1, at least about 3:1, at least about 5:1, at least about 7:1, at least about 9:1, or at least about 11:1.

Embodiment B10 is the process of any of embodiments B to B9 wherein ratio of the mass flow rates for the aqueous medium to the carboxylation product slurry fed to the FLLE extraction zone is from about 1:1 to about 15:1, from about 3:1 to about 12:1, from about 5:1 to about 12:1.

Embodiment B11 is the process of any of embodiments B to B10 wherein the ratio of the mass flow rates for the organic solvent to the carboxylation product slurry fed to the FLLE extraction is less than about 1:1, less than about 0.9:1, less than about 0.8:1, less than about 0.7:1, less than about 0.6:1, less than about 0.5:1, less than about 0.4:1, less than about 0.3:1, less than about 0.2:1, less than about 0.1:1, or less than about 0.05:1.

Embodiment B12 is the process of any of embodiments B to B11 wherein the ratio of the mass flow rates for the organic solvent to the carboxylation product slurry fed to the FLLE extraction zone is from about 0.05:1 to about 1:1, from about 0.1:1 to about 0.8:1, or from about 0.2:1 to about 0.5:1.

Embodiment B13 is the process of any of embodiments B to B12 wherein the organic solvent and aqueous medium are introduced into the FLLE zone and contacted therein to form an FLLE zone having the organic solvent dispersed throughout the aqueous medium, the carboxylation product slurry being introduced into the FLLE zone having the organic solvent dispersed throughout the aqueous medium.

Embodiment B14 is the process of any of embodiments B1 to B13 wherein the stripping section and rectifying section each comprise a plurality of stages.

Embodiment B15 is the process of embodiment B14 wherein the organic solvent is introduced into an intermediate stage of the stripping section such that there is at least one stage between the intermediate stripping stage and the feed location and at least one stage of the stripping section between the intermediate stripping stage and the bottom of the column.

Embodiment B16 is the process of embodiment B14 or B15 wherein the aqueous medium is introduced into an intermediate stage of the rectifying section such that there is at least one stage between the intermediate rectifying stage and the feed location and at least one stage of the rectifying section between the intermediate rectifying stage and the top of the column.

Embodiment B17 is the process of claim any of embodiments B14 to B16 wherein there is at least one stage of the stripping section between the bottom of the column and the feed location of the organic solvent.

Embodiment B18 is the process of embodiment B14 or B17 wherein there is at least one stage of the rectifying section between the top of the column and the feed location of the aqueous medium.

Embodiment B19 is the process of any of embodiments B to B18 wherein temperature of the carboxylation product mixture within the FLLE zone is at least about 25° C. or from about 25° C. to about 100° C.

Embodiment B20 is the process of any of embodiments B to B19 wherein at least about 90 wt %, at least about 95 wt %, or at least about 99 wt % of the 3,6-DCSA and/or a salt thereof present in the carboxylation product slurry introduced into the FLLE zone is present in the aqueous phase extract.

Embodiment B21 is the process of any of embodiments B to B20 wherein at least about 30 wt %, at least about 40 wt %, at least about 50 wt %, at least about 60 wt %, at least about 70 wt %, at least about 80 wt %, or at least about 90 wt % of the 2,5-DCP present in the carboxylation product slurry introduced into the FLLE zone is present in the organic phase extract.

Embodiment B22 is the process of any of embodiments B to B21 wherein the aqueous medium further comprises an acid.

Embodiment B23 is the process of embodiment B22 wherein the acid is selected from the group consisting of hydrochloric acid, sulfuric acid, acetic acid, and combinations thereof.

Embodiment B24 is the process of any of embodiments B to B23 wherein an acidic stream is introduced into the FLLE zone at a location between the inlet for the aqueous medium and the organic solvent.

Embodiment B25 is the process of embodiment B24 wherein the acidic stream is introduced at a point between the feed location and the inlet for the aqueous medium.

Embodiment B26 is the process of embodiment B24 wherein the acidic medium is introduced at a point between the feed location and the inlet for the organic solvent.

Embodiment B27 is the process of any of embodiments B to B26 wherein the aqueous phase extract comprises one or more salts of 3,6-DCSA as solids distributed throughout the aqueous medium of the aqueous phase extract.

Embodiment B28 is the process of embodiment B27 wherein the aqueous phase extract has a pH of from about 4 to about 9, from about 5 to about 9, or from about 7 to about 9.

Embodiment B29 is the process of any of embodiments B to B28, the process further comprising feeding the aqueous phase extract to a mixing vessel, wherein an acid is introduced into the mixing vessel;

mixing the aqueous phase extract with the acid, thereby acidifying the one or more salts of 3,6-DCSA and the one or more salts of 2,5-DCP to form an aqueous mixture comprising water, 3,6-DCSA solids, and 2,5-DCP in the aqueous phase;

heating the aqueous mixture, thereby forming a vapor phase comprising 2,5-DCP over the acidified aqueous phase;

recovering the vapor phase from the mixing vessel, wherein the vapor phase is enriched in 2,5-DCP relative to the aqueous mixture; and recovering a product slurry from the mixing vessel comprising 3,6-DCSA solids, wherein the product slurry is enriched in 3,6-DCSA relative to the aqueous mixture.

Embodiment B30 is the process of embodiment B29, the process further comprising removing water from the product slurry, thereby forming a 3,6-DCSA solids product, the 3,6-DCSA solids product containing no more than about 0.9 wt %, no more than about 0.8 wt %, no more than about 0.7 wt %, no more than about 0.6 wt %, no more than about 0.5 wt %, no more than about 0.4 wt %, no more than about 0.3 wt %, no more than about 0.2 wt %, or no more than about 0.1 wt %, 2,5-DCP and/or a salt thereof.

Embodiment B31 is the process of embodiment B29 or B30, the process further comprising:

recovering and condensing the vapor phase comprising 2,5-DCP to form a liquid stream comprising 2,5-DCP and/or a salt thereof.

Embodiment B32 is the process of embodiment B31 wherein the liquid stream comprising 2,5-DCP and/or a salt thereof is combined with the aqueous medium introduced into the FLLE zone.

Embodiment B33 is the process of embodiment B31 further comprising recovering 2,5-DCP and/or a salt thereof from the liquid stream, and carboxylating the recovered 2,5-DCP and/or a salt thereof in an organic reaction medium comprising an organic solvent, thereby forming a product mixture in the organic solvent comprising 3,6-DCSA and/or a salt thereof.

Embodiment B34 is the process of embodiment B31, further comprising distilling the liquid stream comprising 2,5-DCP to provide 2,5-DCP feed stream having a reduced water content than the liquid stream.

Embodiment B35 is the process of embodiment B31, wherein the liquid stream comprising 2,5-DCP is combined with organic phase extract recovered from the FLLE zone.

Embodiment B36 is the process of any of embodiments B29 to B35 wherein the organic phase extract further comprises one or more dimers of 2,5-DCP, the process further comprising separation of 2,5-DCP from the one or more impuritites and the one or more dimers of 2,5-DCP.

Embodiment C is a process for recovery of 2,5-dichlorophenol (2,5-DCP) and/or a salt thereof, the process comprising:

carboxylating 2,5-DCP and/or a salt thereof in an organic reaction medium comprising an organic solvent, thereby forming a product mixture in the organic solvent comprising 3,6-dichlorosalicylic acid and one or more salts thereof, unreacted 2,5-DCP, one or more salts of 2,5-DCP, and one or more dimers of 2,5-DCP;

feeding the product mixture to an extraction zone;

feeding an organic solvent to the extraction zone;

feeding an aqueous medium to the extraction zone;

contacting the product mixture with the organic solvent and the aqueous medium in the extraction zone, wherein at least a portion of the unreacted 2,5-DCP and dimers of 2,5-DCP are transferred to an organic phase comprising the organic solvent and one or more salts of 2,5-DCP are transferred to an aqueous phase, wherein the aqueous phase is enriched in 3,6-dichlorosalicylic acid and salts of 2,5-DCP relative to the product mixture and the organic phase is enriched in unreacted 2,5-DCP as compared to the product mixture;

removing an organic extract comprising the organic phase from the extraction zone; recovering 2,5-dichlorophenol from the organic phase, wherein:

recovered 2,5-DCP is fed to an extraction zone for recovery of impurities therefrom and/or fed to a carboxylation reactor for production of 3,6-dichlorosalicylic acid.

Embodiment C1 is the process of embodiment C wherein the organic solvent of the organic reaction medium and the organic solvent fed to the extraction zone are the same.

Embodiment C2 is the process of embodiment C or C1 wherein the extraction zone comprises a column, a centrifuge, a mixer/settler, or a decanter.

Embodiment C3 is the process of any of embodiments C to C2, wherein the extraction zone comprises a column having a rectifying section and a stripping section; and wherein:

the organic solvent is fed to the stripping section of the extraction zone;

the aqueous medium is fed to the rectifying section of the extraction zone; and the product mixture is contacted with the organic solvent and the aqueous medium in the extraction zone, thereby forming the aqueous phase and the organic phase.

Embodiment C4 is the process of any of embodiments C1 to C3, further comprising introducing an acid into the product mixture prior to its feeding into the extraction zone, wherein introduction of the acid enhances recovery of unreacted 2,5-DCP in the organic phase.

Embodiment C5 is the process of any of embodiments C1 to C4, further comprising removing one or more impurities from the 2,5-DCP prior to carboxylation, wherein the one or more impurities comprise 2,4-DCP and the one or more impurities are removed by a process comprising feeding the 2,5-DCP into a fractional liquid-liquid extraction (FLLE) zone comprising a rectifying section and a stripping section.

Embodiment C6 is the process of any of embodiments A to C5, wherein the recovered 2,5-DCP is purified by a process comprising contact with an aqueous liquid medium and contact with an alkali metal hydroxide.

Embodiment D is a process for removing impurities from a feed mixture comprising 2,5-dichlorophenol (2,5-DCP) and/or a salt thereof, the process comprising:

heating the 2,5-DCP feed mixture to a temperature of at least about 25° C., the 2,5-DCP feed mixture comprising an organic solvent, 2,5-DCP, 2,5-dichloro-4-nitrophenol (2,5-DCNP), and a plurality of chlorophenol dimers;

feeding the 2,5-DCP feed mixture into a first extraction zone;

contacting the feed mixture within the first extraction zone with a first aqueous solution comprising a base, thereby forming a first organic phase extract comprising the organic solvent, 2,5-DCP and the plurality of chlorophenol dimers and forming a first aqueous phase extract comprising 2,5-DCNP and/or salts thereof, the first aqueous phase extract being enriched in 2,5-DCNP and/or salts thereof as compared to the first organic phase extract and the 2,5-DCP feed mixture;

feeding the first organic phase extract into a second extraction zone and contacting the first organic phase extract with a second aqueous solution comprising a base, thereby forming a second organic phase extract comprising the chlorophenol dimers and forming a second aqueous phase extract comprising 2,5-DCP and/or salts thereof, the second organic phase extract enriched in the chlorophenol dimers as compared to the first organic phase extract and the second aqueous phase extract enriched in 2,5-DCP as compared to the first organic phase extract.

Embodiment D1 is the process of embodiment D, wherein the plurality of chlorophenol dimers comprise meta-(chloro-(2,5dichlorophenoxy)phenol) (Meta-CDPP) and ortho-(chloro-(2,5dichlorophenoxy)phenol) (Ortho-CDPP) and the second organic phase extract contains at least about 50 wt %, at least about 60 wt %, or at least about 70 wt % of the dimers present in the first organic phase extract.

Embodiment D2 is the process of embodiment D or D1 wherein the second aqueous phase extract contains at least about 90 wt %, at least about 95 wt %, or at least about 99 wt % of the 2,5-DCP present in the first organic phase extract.

Embodiment D3 is the process of any of embodiments D to D2 wherein the pH of the second aqueous phase extract is at least about 7.1, at least about 8, at least about 9, at least about 10, at least about 11, or from about 7.1 to about 13, from about 8 to about 12, from about 10 to about 12, or about 11.

Embodiment D4 is the process of any of embodiments D to D3 wherein the second aqueous solution comprises the base in a molar ratio to 2,5-DCP present in the first organic phase extract of at least about 0.5:1, at least about 0.6:1, at least about 0.7:1, at least about 0.8:1, at least about 0.9:1, at least about 1.0:1, or at least about 1.1:1, from about 0.5:1 to about 1.5:1, from about 0.7:1 to about 0.1.1:1, from about 0.7:1 to about 1.0:1, or from about 0.7:1 to about 0.9:1.

Embodiment D5 is the process of any of embodiments claims D to D4 wherein the concentration of base in the second aqueous solution is from about 1 wt % to about 45 wt %, from about 5 wt % to about 40 wt %, from about 5 wt % to about 30 wt %, from about 5 wt % to about 20 wt %, from about 7 wt % to about 15 wt %, from about 7 wt % to about 12 wt %, or from about 10 wt % to about 12 wt %.

Embodiment D6 is the process of any of embodiments D to D5 wherein the first extraction zone comprises at least 10 stages, at least 15 stages, at least 20 stages, or at least 25 stages.

Embodiment D7 is the process of any of embodiments D to D6 wherein the base of the first aqueous solution comprises an alkali or alkaline earth hydroxide, carbonate, or bicarbonate.

Embodiment D8 is the process of any of embodiments D to D7 wherein the base constitutes less than about 2 wt %, less than about 1 wt %, less than about 0.5 wt %, less than about 0.2 wt %, or less than about 0.1 wt % of the first aqueous solution.

Embodiment D9 is the process of any of embodiments D to D8 wherein the base constitutes from about 0.01 wt % to about 2 wt %, from about 0.05 to about 1 wt %, or from about 0.1 to about 1 wt % of the first aqueous solution.

Embodiment D10 is the process of any of embodiments D to D9 wherein the molar ratio of base to 2,5-DCNP present in the feed mixture is from about 0.5:1 to about 5:1, from about 0.5:1 to about 3:1, from about 0.5:1 to about 2:1, or from about 0.5:1 to about 1.5:1.

Embodiment D11 is the process of any of embodiments D to D10, wherein the first organic phase extract contains at least about 90%, at least about 95%, or at least about 99% of the 2,5-DCP present in the feed mixture.

Embodiment D12 is the process of any of embodiments D to D11, wherein the first aqueous phase extract contains at least about 90%, at least about 95%, or at least about 99% of the 2,5-DCNP present in the feed mixture.

Embodiment D13 is the process of any of embodiments D to D12, wherein the pH of the first aqueous phase extract is less than about 8, less than about 7, or less than about 6.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

What is claimed is:

1. A process for dehydrating a chlorophenol salt feed mixture, the process comprising:
providing a feed mixture comprising a chlorophenol salt, water, and an organic solvent;
distilling the feed mixture within a distillation zone, thereby forming an overheads fraction comprising water and a portion of the organic solvent and a bottoms fraction comprising the chlorophenol salt and a portion of the organic solvent, the bottoms fraction being enriched in chlorophenol salt as compared to the overheads fraction;
condensing the overheads fraction to form a recycle stream comprising recovered organic solvent and water;
removing water from the recycle stream; and
feeding the recycle stream comprising recovered organic solvent to the distillation zone, wherein the distillation zone comprises a column comprising one or more intermediate stages to which the feed mixture is fed, the distillation zone further comprising a rectifying zone comprising one or more rectifying stages above the one or more intermediate stages, and a stripping zone comprising one or more stripping stages below the one or more intermediate stages, and wherein the distillation zone is operated such that the overheads fraction is removed from the distillation zone while the recycle stream is fed to the rectifying zone.

2. The process of claim 1 wherein the overheads fraction comprises a minimum boiling azeotrope comprising the organic solvent and water, the overheads fraction having a boiling point less than the boiling point of any combination of its constituents.

3. The process of claim 1 wherein water is removed from the recycle stream by a liquid-liquid separation method selected from the group consisting of decanting, extraction, mixing/settling, centrifugation, and combinations thereof.

4. The process of claim 1, further comprising recovering a chlorophenol salt from the bottoms fraction and wherein the chlorophenol salt is the potassium salt of 2,5-DCP, the process further comprising carboxylating the salt of 2,5-DCP in the recovered bottoms fraction removed from the distillation zone to form a carboxylation product slurry comprising 3,6-dichlorosalicylic acid or a salt thereof.

5. The process of claim 4, further comprising methylating 3,6-dichlorosalicylic acid or a salt thereof with a methylating agent to form 3,6-dichloro-2-methoxybenzoic acid or salt thereof and/or methyl 3,6-dichloro-2-methyoxybenzoate.

6. The process of claim 5, further comprising saponifying methyl 3,6-dichloro-2-methyoxybenzoate with a base to form a salt of 3,6-dichloro-2-methoxybenzoic acid.

7. The process of claim 1, wherein the chlorophenol salt is 2,5-DCP, the process further comprising:
carboxylating 2,5-DCP and/or a salt thereof in an organic reaction medium comprising an organic solvent, thereby forming a product mixture in the organic solvent comprising 3,6-dichlorosalicylic acid and one or more salts thereof, unreacted 2,5-DCP, one or more salts of 2,5-DCP, and one or more dimers of 2,5-DCP;
feeding the product mixture to an extraction zone;
feeding an organic solvent to the extraction zone;
feeding an aqueous medium to the extraction zone;
contacting the product mixture with the organic solvent and the aqueous medium in the extraction zone, wherein at least a portion of the unreacted 2,5-DCP and dimers of 2,5-DCP are transferred to an organic phase comprising the organic solvent and one or more salts of 2,5-DCP are transferred to an aqueous phase, wherein the aqueous phase is enriched in 3,6-dichlorosalicylic acid and salts of 2,5-DCP relative to the product mixture and the organic phase is enriched in unreacted 2,5-DCP as compared to the product mixture;
removing an organic extract comprising the organic phase from the extraction zone;
recovering 2,5-dichlorophenol from the organic phase, wherein:
recovered 2,5-DCP is fed to an extraction zone for recovery of impurities therefrom and/or fed to a carboxylation reactor for production of 3,6-dichlorosalicylic acid.

8. The process of claim 1, wherein the chlorophenol salt is 2,5-dichlorophenol (2,5-DCP) and/or a salt thereof, the process further comprising:
providing a feed mixture comprising 2,5-DCP and/or a salt thereof;
heating the 2,5-DCP feed mixture to a temperature of at least about 25° C., the 2,5-DCP feed mixture comprising an organic solvent, 2,5-DCP, 2,5-dichloro-4-nitrophenol (2,5-DCNP), and a plurality of chlorophenol dimers;
feeding the 2,5-DCP feed mixture into a first extraction zone;
contacting the feed mixture within the first extraction zone with a first aqueous solution comprising a base, thereby forming a first organic phase extract comprising the organic solvent, 2,5-DCP and the plurality of chlorophenol dimers and forming a first aqueous phase extract comprising 2,5-DCNP and/or salts thereof, the first aqueous phase extract being enriched in 2,5-DCNP and/or salts thereof as compared to the first organic phase extract and the 2,5-DCP feed mixture;
feeding the first organic phase extract into a second extraction zone and contacting the first organic phase extract with a second aqueous solution comprising a base, thereby forming a second organic phase extract comprising the chlorophenol dimers and forming a second aqueous phase extract comprising 2,5-DCP and/or salts thereof, the second organic phase extract enriched in the chlorophenol dimers as compared to the first organic phase extract and the second aqueous phase extract enriched in 2,5-DCP as compared to the first organic phase extract.

9. The process of claim 1 wherein the chlorophenol salt comprises the potassium salt of 2,5-DCP, the sodium salt of 2,5-DCP, or a combination thereof.

10. The process of claim 1 wherein the organic solvent has a normal boiling point greater than 100° C.

11. The process of claim 1 wherein the feed mixture is provided by introducing the organic solvent into the distillation zone and then combining an intermediate feed mixture of the chlorophenol salt and water with the organic solvent within the distillation zone.

12. The process of claim 1 wherein the mass ratio of organic solvent to chlorophenol salt in the feed mixture is from about 0.2:1 to about 3:1.

13. The process of claim 1 wherein the mass ratio of water to chlorophenol salt in the feed mixture is from about 0.2:1 to about 2:1.

14. The process of claim 1 wherein the distillation is operated at a pressure below atmospheric pressure.

15. The process of claim 1 wherein the bottoms fraction contains less than about 0.1 wt. % water.

16. The process of claim 1 wherein the bottoms fraction contains at least about 10 wt % chlorophenol salt.

17. The process of claim 1 wherein the bottoms fraction contains at least about 45 wt % of the organic solvent.

18. The process of claim 4, wherein the carboxylation product slurry further comprises unreacted 2,5-DCP and/or a salt thereof, and one or more impurities;
the process further comprising:
feeding the carboxylation product slurry to a fractional liquid-liquid extraction (FLLE) zone;
feeding an organic solvent to the FLLE zone;
feeding an aqueous medium to the FLLE zone;
contacting the carboxylation product slurry with the organic solvent and the aqueous medium in the FLLE zone, wherein at least a portion of the unreacted 2,5-DCP and/or a salt thereof and the one or more impurities are transferred to an organic phase comprising the organic solvent and at least a portion of the 3,6-DCSA or a salt thereof is transferred to an aqueous phase;

recovering an aqueous phase extract comprising one or more salts of 3,6-DCSA from the FLLE zone, wherein the weight ratio of salts of 3,6-DCSA to 2,5-DCP in the aqueous phase extract is greater than the weight ratio of salts of 3,6-DCSA to 2,5-DCP in the carboxylation feed mixture;

recovering an organic phase extract comprising 2,5-DCP, the organic solvent and one or more impurities from the FLLE zone; and neutralizing the salts of 3,6-DCSA in the aqueous phase extract to form a product mixture comprising 3,6-DCSA.

19. The process of claim 18, wherein the FLLE zone comprises at least one vertical column having a feed location for the carboxylation product slurry, a stripping section, and a rectifying section, wherein the stripping section is the portion of the column situated beneath the feed location and the rectifying section is the portion of the column situated above the feed location, wherein the aqueous phase extract is recovered from the stripping section of the FLLE zone, and the organic phase extract is recovered from the rectifying section of the FLLE extraction zone.

20. The process of claim 18 wherein the carboxylation product slurry comprises the organic carboxylation reaction medium, unreacted 2,5-DCP and/or a salt thereof, and product solids comprising one or more salts of 3,6-DCSA.

21. The process of claim 18 wherein the aqueous medium further comprises an acid.

22. The process of claim 18 wherein the aqueous phase extract comprises one or more salts of 3,6-DCSA as solids distributed throughout the aqueous medium of the aqueous phase extract.

23. The process of claim 22 wherein the aqueous phase extract has a pH of from about 4 to about 9.

24. The process of claim 18, the process further comprising feeding the aqueous phase extract to a mixing vessel, wherein an acid is introduced into the mixing vessel;

mixing the aqueous phase extract with the acid, thereby acidifying the one or more salts of 3,6-DCSA and the one or more salts of 2,5-DCP to form an aqueous mixture comprising water, 3,6-DCSA solids, and 2,5-DCP in the aqueous phase;

heating the aqueous mixture, thereby forming a vapor phase comprising 2,5-DCP over the acidified aqueous phase;

recovering the vapor phase from the mixing vessel, wherein the vapor phase is enriched in 2,5-DCP relative to the aqueous mixture; and recovering a product slurry from the mixing vessel comprising 3,6-DCSA solids, wherein the product slurry is enriched in 3,6-DCSA relative to the aqueous mixture.

25. The process of claim 8 wherein the second aqueous solution comprises the base in a molar ratio to 2,5-DCP present in the first organic phase extract of at least about 0.5:1.

26. The process of claim 8 wherein the concentration of base in the second aqueous solution is from about 1 wt % to about 45 wt %.

27. The process of claim 8 wherein the base constitutes less than about 2 wt % of the first aqueous solution.

28. The process of claim 8 wherein the molar ratio of base to 2,5-DCNP present in the feed mixture is from about 0.5:1 to about 5:1.

29. The process of claim 10 wherein the organic solvent is selected from the group consisting of xylene, toluene, benzene, and combinations thereof.

30. The process of claim 11 wherein the organic solvent is heated within the distillation zone to a temperature of at least about 60° C.

31. The process of claim 11 wherein the temperature of the intermediate feed mixture is at least about 30° C.

\* \* \* \* \*